(12) United States Patent
Miyamoto et al.

(10) Patent No.: US 11,007,269 B2
(45) Date of Patent: *May 18, 2021

(54) P53 DEGRADATION INDUCING MOLECULE AND PHARMACEUTICAL COMPOSITION

(71) Applicant: Tokyo University of Science Foundation, Tokyo (JP)

(72) Inventors: Etsuko Miyamoto, Tokyo (JP); Masaaki Ozawa, Tokyo (JP)

(73) Assignee: Tokyo University of Science Foundation, Tokyo (JP)

(*) Notice: Subject to any disclaimer, the term of this patent is extended or adjusted under 35 U.S.C. 154(b) by 94 days.

This patent is subject to a terminal disclaimer.

(21) Appl. No.: 16/349,708

(22) PCT Filed: Nov. 13, 2017

(86) PCT No.: PCT/JP2017/040781
§ 371 (c)(1),
(2) Date: May 14, 2019

(87) PCT Pub. No.: WO2018/092725
PCT Pub. Date: May 24, 2018

(65) Prior Publication Data
US 2019/0314508 A1 Oct. 17, 2019

(30) Foreign Application Priority Data
Nov. 15, 2016 (JP) .............................. JP2016-222681

(51) Int. Cl.
| A61K 47/54 | (2017.01) |
| A61P 7/04 | (2006.01) |
| A61P 35/00 | (2006.01) |
| A61K 31/167 | (2006.01) |

(52) U.S. Cl.
CPC ............ *A61K 47/54* (2017.08); *A61K 31/167* (2013.01); *A61P 7/04* (2018.01); *A61P 35/00* (2018.01)

(58) Field of Classification Search
CPC .... A61K 31/167; A61K 47/54; A61K 47/545; A61K 47/55; A61K 47/64; A61K 45/00; A61K 47/51; A61P 25/00; A61P 3/10; A61P 43/00; A61P 7/04; A61P 9/00; C07C 233/60; C07C 237/22; C07D 403/12; C07K 5/06026; C07K 5/0808
See application file for complete search history.

(56) References Cited

U.S. PATENT DOCUMENTS

| 5,882,941 A | 3/1999 | Essignmann et al. |
| 7,208,157 B2 | 4/2007 | Dashaies et al. |
| 2009/0270439 A1 | 10/2009 | Ohyagi |
| 2010/0074908 A1 | 3/2010 | Solomon et al. |
| 2012/0115232 A1 | 5/2012 | Kanemaki et al. |
| 2013/0190340 A1 | 7/2013 | Hedstrom et al. |
| 2016/0264627 A1 | 9/2016 | Henning et al. |
| 2018/0164289 A1 | 6/2018 | Miyamoto et al. |

FOREIGN PATENT DOCUMENTS

| CN | 103153335 A | 6/2013 |
| EP | 3542821 A1 | 9/2019 |
| EP | 3543349 A1 | 9/2019 |
| JP | 2008-081508 | 4/2008 |
| JP | 2008-533986 | 8/2008 |
| JP | 2009149524 | 7/2009 |
| JP | 2013056837 | 3/2013 |
| JP | 2013177444 | 9/2013 |
| WO | WO00/45165 A1 | 8/2000 |
| WO | WO2008/147536 A1 | 12/2008 |
| WO | WO2012/003281 | 1/2012 |
| WO | WO2013/106643 A2 | 7/2013 |
| WO | WO2016204197 | 12/2016 |

OTHER PUBLICATIONS

Pullarkat et al. Hemoglobin (2014) 38(3): 188-195 (Year: 2014).*
Shkedy et al. FEBS Lett. (1994) 348: 126-130 (Year: 1994).*
Office Action issued in the related CN Patent Application No. CN201680048166.8, dated Jul. 22, 2020.
Itoh, Y. et al., "Development of target protein-selective degradation inducer for protein knockdown", Bioorg. Med. Chem., 2011, 19, 3229-3241.
Demizu, Y. et al., "Design and synthesis of estrogen receptor degradation inducer based on a protein knockdown strategy.", Bioorg. Med. Chem. Lett., 2012, 15, 1793-1796.
Hines, J. et al., "Posttranslational protein knockdown coupled to receptor tyrosine kinase activation with phosphoPROTACs.", Proc. Natl. Acad. Sci. U.S.A., 2013, 110( 22), 8942-8947.
2012, entire text, Astellas Foundation for Research on Metabolic Disorders non-official translation( INOBE, Tomonao. Molecular Mechanisms of Protein Degradation by Proteasomes, 44th Annual Research Report.).
Bell, S. et al., p. 53 Contains Large Unstructured Regions in its Native State, J Mol Biol, 2002, vol. 322, pp. 917-27, ISSN 0022-2836, abstract, etc.
Long, M.J. et al., Inhibitor Mediated Protein Degradation, Chem Biol, 2012, vol. 19, p. 629-37, ISSN 1074-5521.
Shi, Y. et al., Boc3Arg-Linked Ligands Induce Degradation by Localizing Target Proteins to the 20S Proteasome, ACS Chem Biol, Oct. 5, 2016, vol. 11, p. 3328-37, ISSN 1554-8937.
I.N.Lavrik et al: "Caspases: pharmacological manipulation of cell death", Journal of Clinical Investigation, vol. 115, No. 10, Oct. 1, 2005 (Oct. 1, 2005), pp. 2665-2672, XP055522159.

(Continued)

*Primary Examiner* — Susan M Hanley
(74) *Attorney, Agent, or Firm* — Pearl Cohen Zedek Latzer Baratz LLP

(57) ABSTRACT

A p53 degradation inducing molecule which can induce degradation of p53 proteins or p53 composites, and a pharmaceutical composition containing said p53 degradation inducing molecule are provided. This p53 degradation inducing molecule is a conjugate of a p53 affinity molecule which has affinity for p53 proteins or p53 composites, and a proteolysis induction tag which has affinity for protease and which does not inhibit proteolysis of proteins by protease.

9 Claims, 9 Drawing Sheets

(56) References Cited

OTHER PUBLICATIONS

J.T. Nguyen: "Direct activation of the apoptosis machinery as a mechanism to target cancer cells", Proceedings of the National Academy of Sciences, vol. 100, No. 13, Jun. 16, 2003 (Jun. 16, 2003), pp. 7533-7538, XP055072593.
Niki Chondrogianni et al: "Proteasome activation delays aging in vitro and in vivo", Free Radical Biology and Medicine, vol. 71, Jun. 1, 2014 (Jun. 1, 2014), pp. 303-320, XP055361652.
Florian Lienert et al: "Synthetic biology in mammalian cells: next generation research tools and therapeutics", Nature Reviews Molecular Cell Biology, vol. 15, No. 2, Jan. 17, 2014 (Jan. 17, 2014), pp. 95-107, XP055206837.
Neklesa, T.K., et al., "Greasy tags for protein removal.", Nature, 2012, 487, 308-309.
Cabrol et al. PLoS ONE (2009) 4(4): e5724, pp. 1-8 (Year: 2009).
Lee et al. Nature (2010) 467: 179-188 (Year: 2010).
Office Action (Restriction requirement) issued in the U.S. Appl. No. 15/736,089, dated Nov. 26, 2019.
Shi et al. abstract from Federation Am. Soc. Exp. Biology Journal (FASEB Journal) (Apr. 1, 2015) vol. 29(1, supplement) (Year:2015).
Office Action issued in the U.S. Appl. No. 15/736,089, dated May 1, 2020.
Kovrigina, E. A. et al., The Ras G Domain Lacks the Intrinsic Propensity to Form Dimers, Biophys J, 2015, vol. 109, pp. 1000-8, ISSN 0006-3495.
Weisi Wang et al.: "Small molecule agents targeting the p53-MDM2 pathway for cancer therapy", Medicinal Research Reviews, vol. 32, No. 6, Nov. 16, 2012 (Nov. 16, 2012), pp. 1159-1196, XP055115939, ISSN; 0198-6325, DOI: 10. 1002/med.20236.
Yoshikazu Johmura et al.: "SCFFbxo22-KDM4A targets methylated p53 for degradation and regulates senescence", Nature Communications, vol. 7, No. 1, Feb. 12, 2016 (Feb. 12, 2016), XP055686014, DOI: 10.1038/ncomms10574.
Extended European Search Report issued in the EP Patent Application No. 17871163.6, dated Apr. 24, 2020.
"Invitation pursuant to Rule 62a(1) EPC and Rule 63(1) EPC" issued in the EP Patent Application No. EP16811671.3, dated Nov. 20, 2018.
Gurung A. B. et al., Significance of Ras Signaling in Cancer and Strategies for its Control. Oncology & Hematology Review, Nov. 23, 2015, vol. 11, No. 2, pp. 147-152.
Sun Q. et al., Discovery of Small Molecules that Bind to K-Ras and Inhibit Sos-Mediated Activation. Angew Chem Int Ed Engl, May 8, 2012, vol. 51, No. 25, pp. 6140-6143.
Office Action issued in the related SG Patent Application No. SG11201904296R, dated Oct. 1, 2020.
Zhi Tan et al.: "Past, Present, and Future of Targeting Ras for Cancer Therapies", Mini Reviews in Medicinal Chemistry, vol. 16, No. 5, Feb. 1, 2016 (Feb. 1, 2016), p. 345-357, XP55731807.
Extended European Search Report issued in the related EP Patent Application No. EP17870778.2, dated Oct. 5, 2020.

* cited by examiner

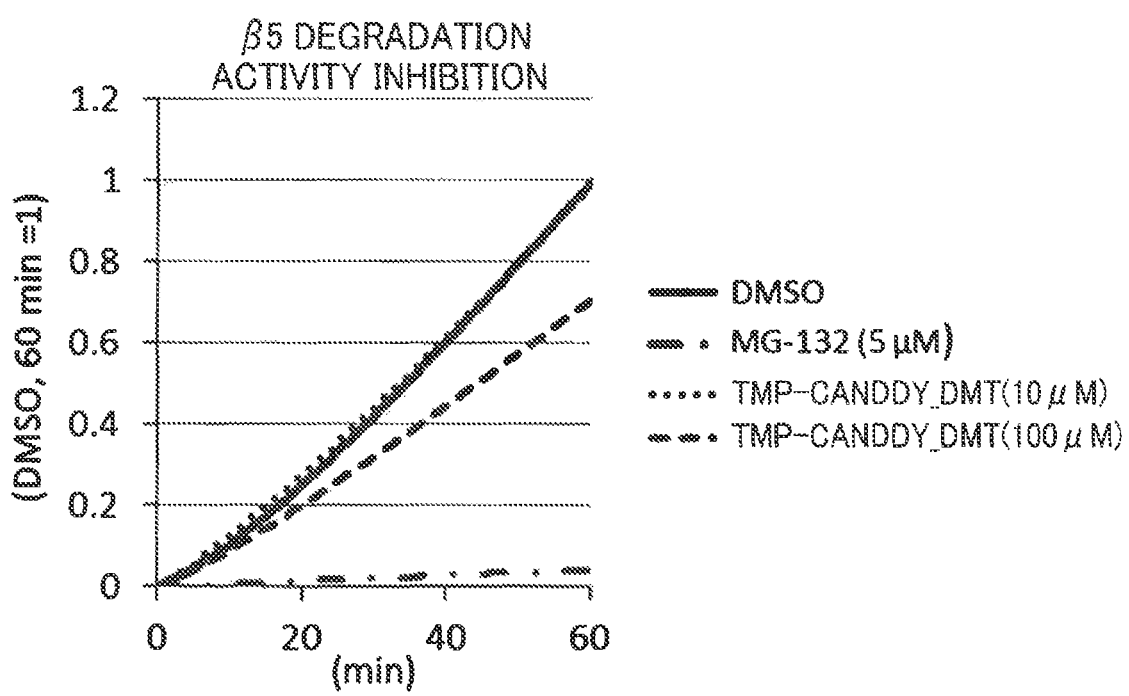

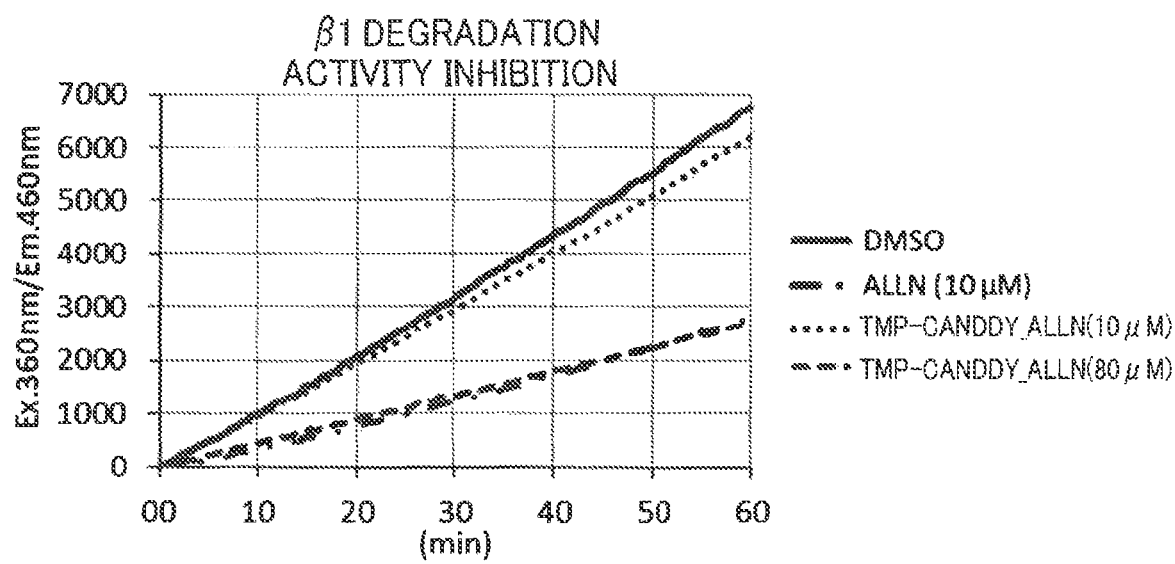
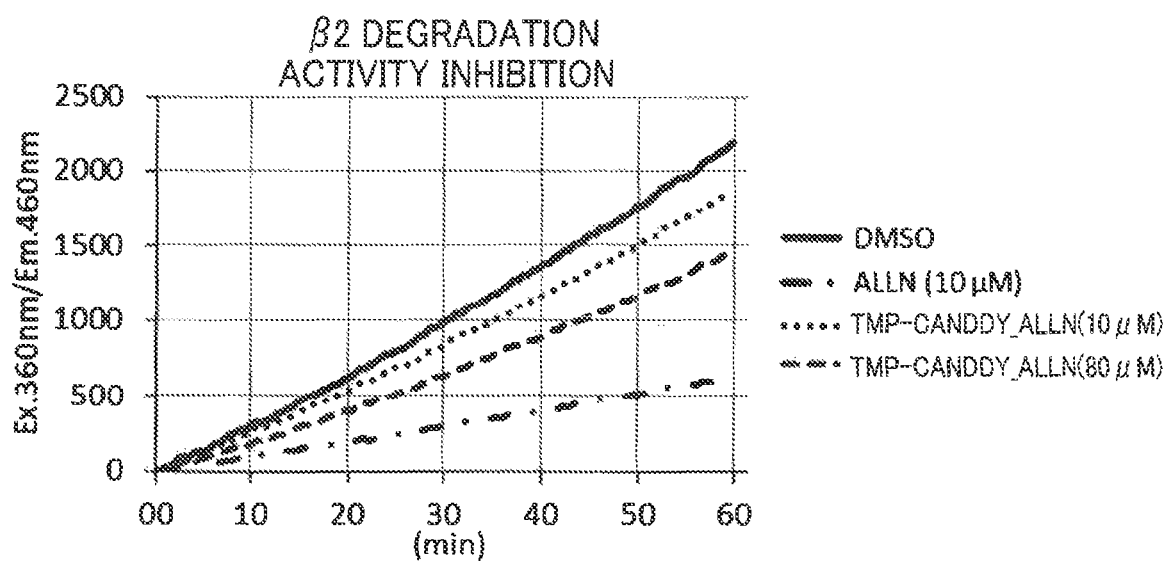

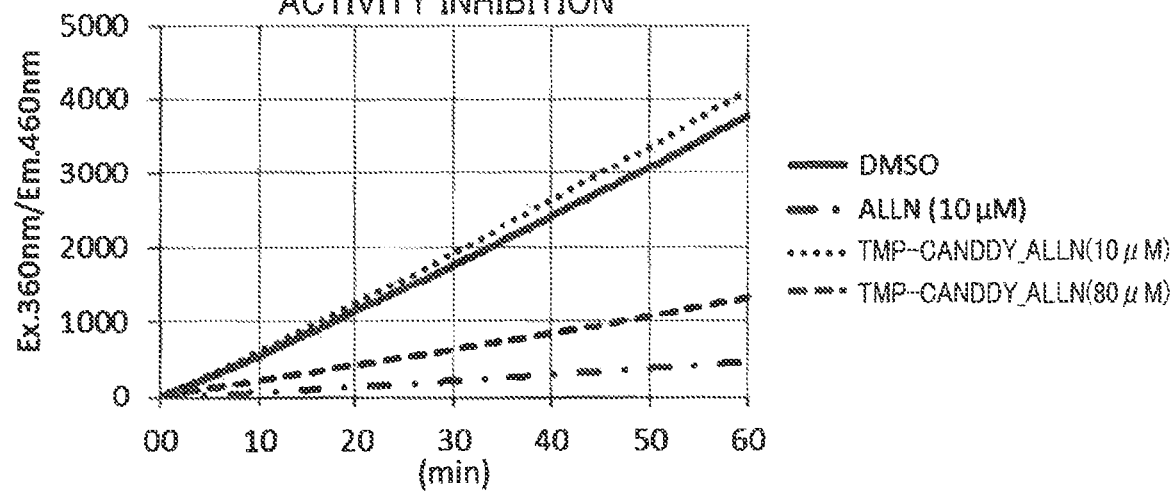

US 11,007,269 B2

P53 DEGRADATION INDUCING MOLECULE AND PHARMACEUTICAL COMPOSITION

CROSS-REFERENCE TO RELATED APPLICATIONS

This application is a National Phase Application of PCT International Application No. PCT/JP2017/040781, International Filing Date Nov. 13, 2017, claiming priority to and benefit of Japanese Patent Application No. 2016-222681, filed Nov. 15, 2016, which are hereby all incorporated by reference in their entireties.

TECHNICAL FIELD

The present disclosure relates to a p53 degradation inducing molecule and a pharmaceutical composition.

BACKGROUND ART

A p53 protein is a protein related to cellular senescence, the stop of the cell cycle, the induction of apoptosis, and the like, and is activated in response to, for example, stress (active oxygen, radiation, and the like) that causes DNA damage.

Conventionally, it is known that in neurological diseases such as Alzheimer's disease and Parkinson's disease, or in ischemic disorders such as cerebral stroke, the expression of the p53 protein is accentuated to induce neuronal cell death. Furthermore, it is known that accentuated expression of the p53 protein promotes the development of cardiac dysfunction by, for example, reducing angiogenesis in the heart. Furthermore, it is known that accentuated expression of the p53 protein decreases the ability to secrete insulin and promotes the onset of diabetes by, for example, reducing mitochondrial function in pancreatic β cells. In addition, in preparation of pluripotent stem cells (for example, iPS cells (induced Pluripotent Stem Cells)) to be used in regenerative medicine, it is known to be necessary to suppress the expression of the p53 gene. Therefore, in treatment of various diseases and in regenerative medicine, methodologies for reducing the amount (expression) of the p53 protein have been considered.

It is thought that activation of the p53 protein elicits suppression of the proliferation of cancerous cells and elicits induction of apoptosis to inhibit cancer. However, in human cancers, the p53 protein is mutated at a proportion of 50% or more, it is known that functions such as suppression of proliferation of cancer cells and induction of apoptosis are reduced. Therefore, in cancer treatment, methodologies for reducing the amount (expression) of the mutant-type p53 protein have been considered.

As a technique for controlling the amount of a target protein at the RNA level, known is the RNAi (RNA interference) technique in which mRNA of the target protein is degraded with siRNA (small interfering RNA).

Furthermore, as a technique for controlling the amount of a target protein at the protein level, known is a technique using a complex of a molecule that binds to the target protein and a molecule that binds to a ubiquitin ligase (E3) (see, for example, Patent Documents 1 to 2, and non-Patent Documents 1 to 3). This technique binds a target protein to a ubiquitin ligase via the complex and specifically ubiquitinates the target protein, leading to degradation by a proteasome. The complex may be referred to as SNIPER (Specific and Nongenetic IAP-dependent Protein ERaser), PROTAC (PROteolysis TArgeting Chimera), etc.

Patent Document 1: Japanese Unexamined Patent Application, Publication No. H2013-056837
Patent Document 2: U.S. Pat. No. 7,208,157, Specification
Non-Patent Document 1: Itoh, Y. et al., "Development of target protein-selective degradation inducer for protein knockdown.", Bioorg. Med. Chem., 2011, 19, 3229-3241
Non-Patent Document 2: Demizu, Y. et al., "Design and synthesis of estrogen receptor degradation inducer based on a protein knockdown strategy.", Bioorg. Med. Chem. Lett., 2012, 15, 1793-1796
Non-Patent Document 3: Hines, J. et al., "Posttranslational protein knockdown coupled to receptor tyrosine kinase activation with phosphoPROTACs.", Proc. Natl. Acad. Sci. U.S.A., 2013, 110(22), 8942-8947

DISCLOSURE OF THE INVENTION

Problems to be Solved by the Invention

However, the RNAi technique suffers from off-target effects, and thus the amount of a target protein is difficult to be controlled in a specific manner. Further, the RNAi technique has been challenged in terms of the delivery of siRNA, and many problems need to be solved for applying to medicine.

On the other hand, the technique using a complex obtained by linking a molecule that binds to a target protein and a molecule that binds to a ubiquitin ligase is easier to be applied to medicine than the RNAi technique. However, the method for ubiquitinating the target protein has the following problems.

(1) There are many types of ubiquitin ligases. The ubiquitin ligases have target specificity. Accordingly, in order to ubiquitinate an individual specific target protein, it is necessary to address the protein individually; for example, it is necessary to design the molecule in accordance with the target protein.

(2) It is difficult to control a ubiquitinated signal. For example, ubiquitination of proteins is known to be associated with signals such as differentiation and carcinogenesis, in addition to degradation of proteins. It is also known that ubiquitination of proteins has tissue specificity and time specificity. Thus, it is presumed that ubiquitination of a target protein may be not a signal for degradation of the target protein but another signal.

(3) Ubiquitin or ubiquitinating enzyme may be defective. For example, there are cases where the ubiquitin or the ubiquitinating enzyme does not function normally (malfunctions) due to mutation or the like, which is often a cause of diseases. Thus, in some cases, it is presumed that ubiquitination of the target protein does not induce degradation of the target protein.

At present, in general, an inhibitor, an activator, and the like are designed as pharmaceutical products. However, a p53 protein is a transcription factor well-known as an undruggable target, and a drug has not yet been created.

In view of the above circumstances, an object of the present disclosure is to provide a p53 degradation inducing molecule capable of inducing degradation of a p53 protein or a p53 complex, and a pharmaceutical composition including the p53 degradation inducing molecule.

Means for Solving the Problems

Specific means for achieving the above object include the following embodiments.

<1> A p53 degradation inducing molecule being a conjugate of a p53 affinity molecule that has an affinity with a p53 protein or a p53 complex, and a protein-degradation inducing tag that has an affinity with a protease and does not inhibit degradation of a protein by the protease; and being capable of inducing degradation of the p53 protein or the p53 complex.

<2> The p53 degradation inducing molecule according to <1>, in which the p53 degradation inducing molecule is capable of inducing degradation of the p53 protein or the p53 complex in a ubiquitin-independent manner.

<3> The p53 degradation inducing molecule according to <1> or <2>, in which the protein-degradation inducing tag has a structure where a protease inhibitory activity of a protease inhibitor is inactivated.

<4> The p53 degradation inducing molecule according to any one of <1> to <3>, in which the protease is a proteasome.

<5> The p53 degradation inducing molecule according to <4>, in which the protein-degradation inducing tag has a structure where a proteasome inhibitory activity of a proteasome inhibitor is inactivated.

<6> The p53 degradation inducing molecule according to <5>, in which the proteasome inhibitory activity is an inhibitory activity against at least one selected from a caspase-like activity, a trypsin-like activity, and a chymotrypsin-like activity.

<7> A pharmaceutical composition including the p53 degradation inducing molecule according to any one of <1> to <6>.

<8> The pharmaceutical composition according to <7>, in which the pharmaceutical composition is used for preventing or treating a p53 protein-mediated disease or condition.

<9> The pharmaceutical composition according to <8>, wherein the p53 protein-mediated disease or condition is a cancer, cellular senescence, a neurological disease, a neuronal cell death, diabetes, or a cardiac dysfunction.

<10> The pharmaceutical composition according to <9>, in which the p53 protein-mediated disease or condition is cellular senescence.

Effects of the Invention

The present disclosure can provide a p53 degradation inducing molecule capable of inducing degradation of a p53 protein or a p53 complex, and a pharmaceutical composition including the p53 degradation inducing molecule.

BRIEF DESCRIPTION OF THE DRAWINGS

FIG. 5C shows inhibitory activity of TMP-CANDDY_DMT, and MG-132 with respect to a catalytic subunit β5 of the proteasome.

FIG. 8A shows inhibitory activity of TMP-CANDDY_ALLN and ALLN with respect to the catalytic subunit β1 of the proteasome.

FIG. 8B shows inhibitory activity of TMP-CANDDY_ALLN and ALLN with respect to the catalytic subunit β2 of the proteasome.

FIG. 8C shows inhibitory activity of TMP-CANDDY_ALLN and ALLN with respect to the catalytic subunit β5 of the proteasome.

PREFERRED MODE FOR CARRYING OUT THE INVENTION

Figure 1:
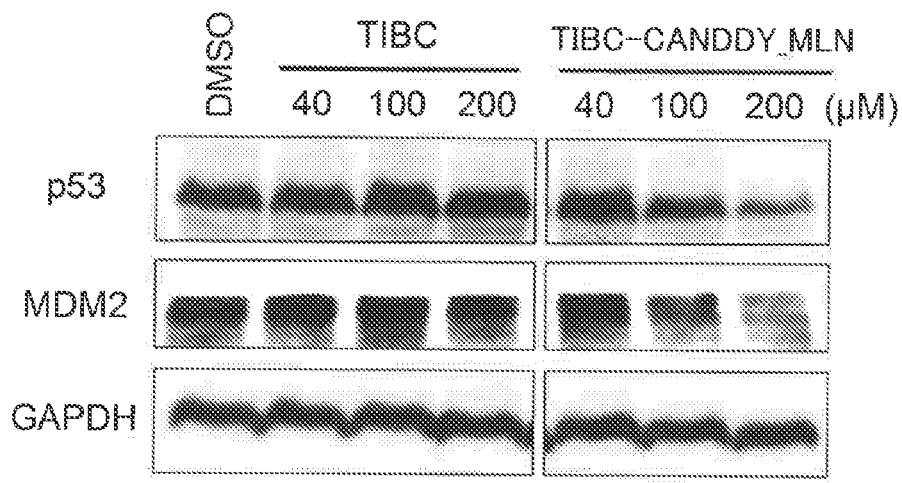
FIG. 1 shows the results of evaluation by Western blot analysis of degradation (knockdown) of an endogenous wild-type p53 protein and MDM2 protein in HCT116 cells to which TIBC-CANDDY_MLN was added.

Below, the embodiments of the present invention will be described in detail. However, the present invention shall not be limited to the following embodiments.

A range of numerical values specified using "-" as used herein refers to a range including values indicated before and after "-" as the minimum value and the maximum value, respectively. Amino acids as used herein are denoted by the single letter notation (for example, "G" for glycine) or the three-letter notation (for example, "Gly" for glycine) as is well known in the art.

<p53 Degradation Inducing Molecule>

A p53 degradation inducing molecule of the present disclosure is a conjugate of a p53 affinity molecule that has an affinity with a p53 protein or a p53 complex, and a protein-degradation inducing tag that has an affinity with a protease and does not inhibit degradation of a protein by the protease; and can induce degradation of the p53 protein or the p53 complex. The p53 degradation inducing molecule of the present disclosure can lead a p53 protein or a p53 complex to degradation (knockdown) by a protease (for example, a proteasome), without ubiquitination of the p53 protein or the p53 complex (in other words, in a ubiquitin-independent manner).

It is noted that a polyubiquitin chain such as a tetraubiquitin chain (Ub$_4$) or a ubiquitin-like domain (UbL) is likely to function as a protein-degradation inducing tag. However, when a polyubiquitin chain or a ubiquitin-like domain is used as a protein-degradation inducing tag, the p53 protein or the p53 complex is indirectly ubiquitinated via the p53 affinity molecule. In the present specification, such an indirect ubiquitination of the p53 protein or the p53 complex is also included in the ubiquitination of the p53 protein or the p53 complex.

(p53 Affinity Molecule)

The p53 affinity molecule constituting the p53 degradation inducing molecule of the present disclosure is a molecule having an affinity with the p53 protein or the p53 complex.

Examples of the p53 complex include a p53/MDM2 complex (a complex of a p53 protein and an MDM2 protein, the same is true hereinafter), a p53/E6 complex, a p53/HDM2 complex, a p53/AICD complex, a p53/RUNX2 complex, a p53/RUNX3 complex, and complexes with well-known molecules known to interact with the p53 protein, without particular limitation.

Here, the molecules having an affinity with p53 complex include a molecule having an affinity with a molecule which forms a complex with a p53 protein (an MDM2 protein and the like), and a molecule having an affinity with the formed complex.

The p53 protein may be a wild-type or a mutant. Examples of the mutants include an R175H mutant (a mutant in which arginine (R) that is an amino acid residue at the 175th position from the N-terminal is changed to histidine (H); the same is true hereinafter), R110L and R248W mutants, a V157F mutant, an S166Y mutant, an L194F mutant, R213Q and M237H mutants, a G245V mutant, a G245S mutant, an R248Q mutant, a R248W mutant, an I254D mutant, an L264L mutant, R273H and P309S mutant, an R273C mutant, an R280K mutant, an R282W mutant, an R273H mutant, S176Y and R248W mutants, a V173A mutant, an R249S mutant, a Y220C mutant, a V272M mutant, a G266Q mutant, a G175E mutant, an S241F mutant, and the like.

Conventionally, in neurological diseases such as Alzheimer's disease and Parkinson's disease, or ischemic disorders such as cerebral stroke, it is known that expression of the p53 protein is increased and neuronal cell death is induced. Furthermore, in diseases such as cardiac dysfunction and diabetes, the expression amount of the p53 protein in cardiac tissue, pancreatic tissue, and the like, is known to be increased. These diseases are known to be ameliorated by administration of inhibitors against the p53 protein. Also, it is indicated that the p53 protein acts as a senescence factor and is involved in arteriosclerosis, metabolic disorder, and the like, caused by lifestyle-related diseases. Furthermore, in preparation of pluripotent stem cells (for example, iPS cells) to be used in regenerative medicine, it is known to be necessary to suppress the expression of the p53 gene.

Preferable examples of the p53 affinity molecule include molecules having affinity with a wild-type (normal-type) p53 protein or a wild-type (normal-type) p53 complex (a complex of a wild-type p53 protein and a molecule having an affinity with the wild-type p53 protein). When the p53 affinity molecule has an affinity with the wild-type p53 protein or the wild-type p53 complex, the wild-type p53 protein or the wild-type p53 complex can be led to degradation (knockdown) by a protease (for example, a proteasome). As a result, it is considered that the p53 degradation inducing molecule including a p53 affinity molecule having an affinity with the wild-type p53 protein or the wild-type p53 complex is useful for prevention or treatment of various diseases such as neurological diseases (including neuronal cell death by cerebral stroke and the like), cardiac dysfunction, and diabetes, and for preparation of the above-described pluripotent stem cells.

Furthermore, it is known that in human cancers, the p53 protein is mutated at high frequency; and that the mutant p53 protein inhibits the action of the wild-type p53 protein, and inhibits suppression of proliferation of cancer cells and induction of apoptosis by the wild-type p53 protein.

Other preferable examples of the p53 affinity molecule include molecules having affinity with a mutant p53 protein or a mutant p53 complex (a complex of a mutant p53 protein and a molecule having an affinity with the mutant p53 protein). When the p53 affinity molecule has an affinity with the mutant p53 protein or the mutant p53 complex, the mutant p53 protein or the mutant p53 complex can be led to degradation (knockdown) by a protease (for example, a proteasome). As a result, it is considered that the p53 degradation inducing molecule including a p53 affinity molecule having an affinity with the mutant p53 protein or the mutant p53 complex is useful for prevention or treatment of various diseases such as cancers.

It is noted that in the above-described method for ubiquitinating the target protein, it is considered that only one of proteins constituting a p53 complex is ubiquitinated, the p53 complex is divided into each protein, and then only the ubiquitinated protein is degraded. On the contrary, the p53 degradation inducing molecule including a p53 affinity molecule having an affinity with the p53 complex is very useful in being capable of degrading the p53 complex itself.

As used herein, the phrase "having an affinity with a p53 protein or a p53 complex" means, for example, the capability of binding to the p53 protein or the p53 complex via a covalent bond, a hydrogen bond, a hydrophobic bond, Van der Waals force, and the like. When the interaction between the other molecules that have been known to interact with the p53 protein or the p53 complex (proteins, peptides, antibodies, DNA, RNA, metabolites, low molecular weight compounds, and the like) and the p53 protein or the p53 complex is influenced by a certain molecule in a concentration dependent manner, it can be determined that the molecule has an affinity with the p53 protein or the p53 complex.

Examples of the p53 affinity molecule include low molecular weight compounds, natural products, peptides, antibodies, and the like. It is noted that in the present disclosure, the antibody includes a fragment including a variable site of the antibody, for example, a Fab fragment or a F(ab') fragment of Ig (immunoglobulin), in addition to anIg having two H-chains and two L-chains. Preferably, the p53 affinity molecule has a molecular weight within the range of, for example, 50 to 5000 for low molecular weight compounds.

A structure of the p53 affinity molecule is not particularly limited as long as it has an affinity with the p53 protein or the p53 complex. As the p53 affinity molecule, for example, a p53 inhibitor or a p53 activator having an affinity with p53 protein, an MDM2 inhibitor having an affinity with a p53/MDM2 complex, PPI (protein-protein interaction) inhibitor of a p53/MDM2 complex, or the like can be used. Furthermore, the p53 affinity molecule can also be obtained by screening from candidate molecules.

Examples of the p53 affinity molecules are shown in the following Tables 1 to 7. However, p53 affinity molecules that can be used for the p53 degradation inducing molecule of the present disclosure are not particularly limited thereto. Existing data bases (Binding DB (www.bindingdb.org/bind/index.jsp), PCI DB (www.tanpaku.org/pci/pci_home.html), ProtChemSl (pcidb.russelllab.org/) and the like) can be consulted for information about p53 affinity molecules if needed.

TABLE 1

| Compound No. | name | Structural formula | Molecular weight | Target | Published paper |
|---|---|---|---|---|---|
| 1 | PRIMA-1^MET (aka. APR-246) | | 199.3 | TP53(R175H) | Oncogene. 2005, 24(21): 3484-3491. Cancer Cell 2009, 15(5): 376-388. J. Clin. Oncol. 2012, 30(29): 3633-3639. Cell Death Dis. 2013, 4: e881. |
| 2 | PRIMA-1 | | 185.2 | TP53(wt) TP53(null) TP53(R110L/R248W) TP53(V157F) TP53(S166Y) TP53(R175H) TP53(L194F) TP53(R213Q/M237H) TP53(G245V) TP53(R248Q) TP53(I254D) TP53(L264L) TP53(R273H/P309S) TP53(R273C) TP53(R280K) TP53(R282W) | Nat. Med. 2002, 8(3): 282-288. Cancer Cell 2009, 15(5): 376-388. |
| 3 | MIRA-1 | | 183.2 | TP53(R175H) TP53(R248Q) TP53(R273H) TP53(R280K) TP53(R282W) TP53(S176Y/R248W) | J. Biol. Chem. 2005, 280(34): 30384-30391. |
| 4 | CP-31398 | | 362.5 | TP53(V173A) TP53(R273H) | Science 1999, 286(5449): 2507-2510. Oncogene 2002, 21(14): 2119-2129. |
| 5 | STIMA-1 | | 172.2 | TP53(R175H) TP53(R273H) | Mol. Oncol. 2008, 2(1): 70-80. |

TABLE 2

| Compound No. | name | Structural formula | Molecular weight | Target | Published paper |
|---|---|---|---|---|---|
| 6 | PhiKan083 | | 238.3 | TP53(Y220C) | Proc. Natl. Acad. Sci. U.S.A. 2008, 105(30): 10360-10365. |

TABLE 2-continued

| Compound No. | name | Structural formula | Molecular weight | Target | Published paper |
|---|---|---|---|---|---|
| 7 | N5C319726 | | 234.3 | TP53(R175H) | *Cancer Cell* 2012, 21(5): 614-25. |
| 8 | WR106 | | 134.2 | TP53(wt) TP53(V272M) | *Mol. Carcinog.* 2002, 33(3): 181-188. *Oncogene* 2005, 24(24): 3964-3975. *J. Biol. Chem.* 2003, 278(14): 11879-87. |
| 9 | Ellipticine | | 246.3 | TP53(R175H) TP53(R249S) TP53(R273H) | *Oncogene* 2003, 22(29): 4478-4487. |
| 10 | PK7088 | | 223.3 | TP53(Y220C) | *Nucleic Acids Res.* 2013,; 41(12): 6034-44. |
| 11 | Stictic acid | | 386.3 | TP53(R175H) TP53(G245S) | *Nat. Commun.* 2013, 4: 1407. |

TABLE 3

| No. | Compound name | Structural formula | Molecular weight | Target | Published paper |
|---|---|---|---|---|---|
| 12 | SCH529074 | 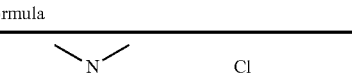 | 563.6 | TP53(wt) TP53(R175H) TP53(L194F) TP53(S241F) TP53(R248W) TP53(R273H) TP53(R273H) | *J. Biol. Chem.* 2010, 285(14): 10198-10212. |

TABLE 3-continued

| No. | Compound name | Structural formula | Molecular weight | Target | Published paper |
|---|---|---|---|---|---|
| 13 | RETRA | | 269.3 | TP53(R248W) TP53(R280K) TP53(G266Q) | *Proc. Natl. Acad. Sci. U.S.A.* 2008, 105(17): 6302-6307. |
| 14 | RITA | | 292.4 | TP53 | *Nat. Med.* 2004, 10(12): 1321-1328. *Nat. Med.* 2005, 11(11): 1135-1136. *PLoS One* 2012, 7(1): e30215. *BMC Cancer* 2014, 14: 437. |
| 15 | Gambogic acid | | 628.8 | TP53(wt) TP53(R175H) TP53(G175E) TP53(R273H) TP53(R280K) TP53(R175H) | *Mol. Cancer Ther.* 2008 Oct; 7(10): 3298-305. *J. Cell Biochem.* 2011 Feb; 112(2): 509-19. |
| 16 | P53R3 | | 592.6 | TP53(R175H) TP53(R248W) TP53(R273H) | *Cell Death Differ.* 2008 Apr; 15(4): 718-29. |
| 17 | RG7112 | | 727.8 | MDM2 | *Cancer Res.* 2013, 73(8): 2587-97. |

TABLE 4

| Compound No. | Compound name | Structural formula | Molecular weight | Target | Published paper |
|---|---|---|---|---|---|
| 18 | RG7388 | | 616.5 | MDM2 | *Oncotarget* 2015, 6(12): 10207-10221. |
| 19 | Ro-2443 | | 401.8 | MDM2 | *Proc. Natl. Acad. Sci. U.S.A.* 2012, 109(29): 11788-93. |
| 20 | Nutlin-3a | | 581.5 | MDM2 | *Science* 2004, 303(5659): 844-848. |
| 21 | SAR405838 (a.k.a. MI-77301) | | 562.5 | MDM2 | *Cancer Res.* 2014 Oct 15; 74(20): 5855-65. |
| 22 | Calcones | | 351.2 | MDM2 | *Biochemistry* 2001 Jan 16; 40(2): 336-44. |

TABLE 5

| Compound No. | name | Structural formula | Molecular weight | Target | Published paper |
|---|---|---|---|---|---|
| 23 | MI-219 | | 552.5 | MDM2 | *Proc. Natl. Acad. Sci. U.S.A.* 2008 Mar 11; 105(10): 3933-8. |
| 24 | MI-713 | | 592.5 | MDM2 | |
| 25 | MI-888 | | 548.5 | MDM2 | *J. Med Chem.* 2013 Jul 11; 56(13): 5553-61. |
| 26 | TDP521252 | | 549.4 | MDM2 | *Mol. Cancer Ther.* 2006 Jan; 5(1): 160-169. |

TABLE 5-continued

| Compound No. | name | Structural formula | Molecular weight | Target | Published paper |
|---|---|---|---|---|---|
| 27 | AM-8553 | | 478.4 | MDM2 | J. Med. Chem. 2012 Jun 14; 55(11): 4936-54. |

TABLE 6

| Compound No. | name | Structural formula | Molecular weight | Target | Published paper |
|---|---|---|---|---|---|
| 28 | Pyrazoles, imidazoles | | 439 | MDM2 | Angew. Chem. Int. Ed. Engl. 2010 Jul 19; 49(31): 5352-6. |
| 29 | Isoindolinone 74a | | 478.9 | MDM2 | J. Med. Chem. 2011 Mar 10; 54(5): 1233-43. |
| 30 | Naturally derived prenylated xanthones | | 296.3 | MDM2 | Biochem. Pharmacol. 2013 May 1; 85(9): 1234-45. |

TABLE 6-continued
| No. | Compound name | Structural formula | Molecular weight | Target | Published paper |
|-----|---------------|--------------------|------------------|--------|-----------------|
| 31 | PXN822 | 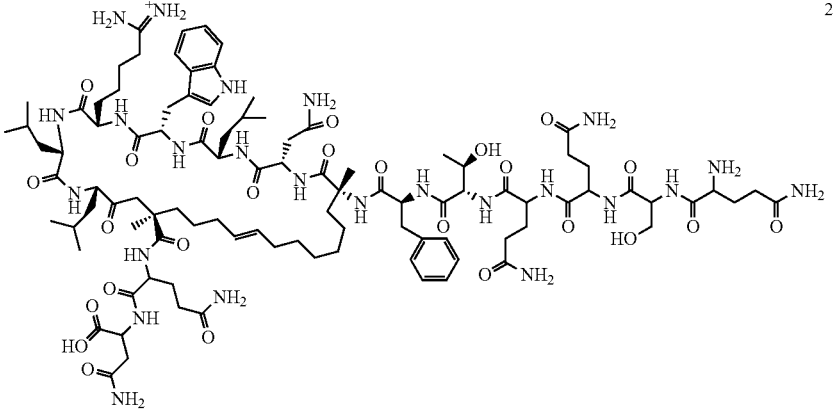 | 668.6 | MDM2 | *Br. J. Pharmacol.* 2012 Jan; 165(2): 328-44. *Int. J. Cancer* 2013 May 15; 132(10): 2248-57. |
| 32 | NSC-279287 | | 597.6 | MDM2 | *J. Med. Chem.* 2004 Aug 12; 47(17): 4163-5. |
TABLE 7
| No. | Compound name | Structural formula | Molecular weight | Target | Published paper |
|-----|---------------|--------------------|------------------|--------|-----------------|
| 33 | SAH-8 (stapled peptides) | 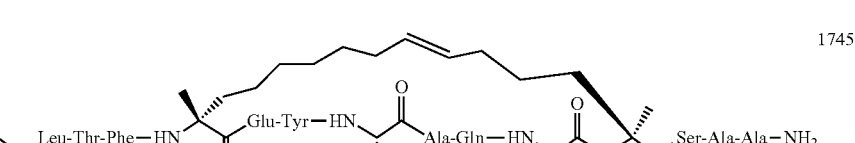 | 2068.4 | MDM2 | *J. Am. Chem. Soc.* 2007 Mar 7; 129(9): 2456-7. *Cancer Cell.* 2010 Nov 16; 18(5): 411-22. |
| 34 | ATSP-7041 (stapled peptides) | | 1745 | MDM2 | *Proc. Natl. Acad. Sci. U.S.A.* 2013 Sep 3; 110(36): E3445-54. |

TABLE 7-continued

| No. | Compound name | Structural formula | Molecular weight | Target | Published paper |
|---|---|---|---|---|---|
| 35 | Spircoligomer (alpha-helix mimic) | [Structural formula shown with Florescein label] | | MDM2 | *PLos One.* 2012; 7(10): e45948. |

(Protein-Degradation Inducing Tag)

The protein-degradation inducing tag constituting the p53 degradation inducing molecule according to the present disclosure is a molecule having an affinity with a protease and that does not inhibit degradation of a protein by the protease. Below, the above protein-degradation inducing tag may also be referred to as a CiKD (Chemical interaction and KnockDown) tag or a CANDDY (Chemical AffiNities and Degradation Dynamics) tag.

There is no particular limitation for the protease, and any molecule having a protease activity can be used. For example, it may be a protease complex such as a proteasome, or may be a protease other than the proteasome. Alternatively, it may be a portion of a proteasome as long as the portion has a protease activity.

Examples of the proteasome include 26S proteasome, an immunoproteasome, and a thymus proteasome.

26S proteasome is composed of 20S proteasome and two units of 19S proteasome, the two units of 19S proteasome being attached to the 20S proteasome. 20S proteasome has a cylindrical structure in which an α-ring consisting of 7 subunits of α1 to α7 and a β-ring consisting of 7 subunits of β1 to β7 are stacked in order of αββα, and β1, β2, and β5 show catalytic activities of a caspase-like activity, a trypsin-like activity, and a chymotrypsin-like activity, respectively.

In the immunoproteasome, the catalytic subunits β1, β2, and β5 are replaced with β1i, μ2i, and μ5i, respectively (Science, 1994, 265, 1234-1237).

In the thymus proteasome, β5t which is expressed specifically in cortical thymic epithelial cells (cTEC) is incorporated along with β1i and β2i (Science, 2007, 316, 1349-1353).

Examples of a protease other than the proteasome include β-secretase, γ-secretase, aminopeptidase, angiotensin-converting enzyme, bromelain, calpine I, calpine II, carboxypeptidase A, carboxypeptidase B, carboxypeptidase P, carboxypeptidase Y, caspase 1, caspase 2, caspase 3, caspase 5, caspase 6, caspase 7, caspase 8, caspase 9, caspase 13, cathepsin B, cathepsin C, cathepsin D, cathepsin G, cathepsin L, chymotrypsin, clostripain, collagenase, complement C1r, complement C1s, complement factor B, complement factor D, dipeptidyl peptidase I, dipeptidyl peptidase II, dipeptidyl peptidase IV, dispase, elastase, endoproteinase Arg-C, endoproteinase Glu-C, endoproteinase Lys-C, ficin, granzyme B, kallikrein, leucine aminopeptidase, matrix metalloprotease, metalloprotease, papain, pepsin, plasmin, procaspase 3, pronase E, proteinase K, renin, thermolysin, thrombin, trypsin, cytosol alanyl aminopeptidase, enkephalinase, neprilysin, and the like.

As used herein, the phrase "having an affinity with a protease" means the capability of binding to a protease, for example, via a covalent bond, a hydrogen bond, a hydrophobic bond, Van der Waals force, and the like. When the thermal stability of a protease changes in the presence of a certain molecule, the molecule can be determined as having an affinity with that protease.

As used herein, the phrase "without inhibiting degradation of a protein by a protease" means that, for example, the protein-degradation inducing tag does not bind to the degradation active site of the protease via a covalent bonding. When a protein is degraded by a protease in the presence of a certain molecule, and the degradation of the protein is inhibited in the presence of a protease inhibitor, the molecule can be considered not to inhibit the degradation of the protein by the protease.

Examples of the protein-degradation inducing tag include low molecular weight compounds, natural products, peptides, antibodies, and the like. The protein-degradation inducing tag preferably has a molecular weight within the range of, for example, 50 to 200000. When the protein-degradation inducing tag is a low molecular weight compound, the molecular weight of the protein-degradation inducing tag is preferably, within the range of, for example, 50 to 5000.

There is no particular limitation for the structure of the protein-degradation inducing tag as long as the protein-degradation inducing tag has an affinity with a protease without inhibiting degradation of a protein by the protease. The protein-degradation inducing tag can be obtained by, for example, screening from the candidate molecules. Furthermore, the protein-degradation inducing tag can be produced by inactivating the protease inhibitory activity (for example, proteasome inhibitory activity) of protease inhibitor (for example, a proteasome inhibitor).

In a certain embodiment, for example, the protein-degradation inducing tag may have, a structure represented by the following formula (I). It is demonstrated that the compound represented by the following formula (I) has an affinity with a protease, and does not inhibit the degradation of protein by the protease (see, for example, the below-mentioned Reference Examples 1 to 4).

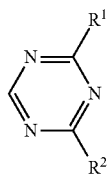
(1)

In the formula (I), $R^1$ and $R^2$ each independently represent a hydrocarbon group having 1 to 20 carbon atoms, an alkoxy group having 1 to 20 carbon atoms, an aryloxy group having 6 to 20 carbon atoms, a hydroxy group, a carboxy group, an amino group, or a halogeno group.

Examples of the hydrocarbon group include an alkyl group, an alkenyl group, an aryl group, combinations thereof, and the like. Specific examples include an alkyl group having 1 to 20 carbon atoms such as a methyl group and an ethyl group; an alkenyl group having 2 to 20 carbon atoms such as a vinyl group and an allyl group; an aryl group having 6 to 20 carbon atoms such as a phenyl group and a naphthyl group; an arylalkyl group having 7 to 20 carbon atoms such as a benzyl group and a phenethyl group; an alkylaryl group having 7 to 20 carbon atoms such as a tolyl group and a xylyl group; and the like. Examples of the halogeno group include a fluoro group, a chloro group, a bromo group, and the like.

In another embodiment, the protein-degradation inducing tag may have a structure in which the proteasome inhibitory activity of a proteasome inhibitor is inactivated. More specifically, at least one inhibitory activity selected from a caspase-like activity, a trypsin-like activity, and a chymotrypsin-like activity can be mentioned as the proteasome inhibitory activity.

The term "structure in which a proteasome inhibitory activity is inactivated" as used herein encompasses a structure in which a proteasome inhibitory activity is attenuated in addition to a structure in which a proteasome inhibitory activity is completely eliminated. In a certain embodiment, the protein-degradation inducing tag has a 50% inhibition concentration ($IC_{50}$) against at least one selected from a caspase-like activity, a trypsin-like activity, and a chymotrypsin-like activity which is 2 times or more of the 50% inhibition concentration ($IC_{50}$) of the original proteasome inhibitor.

As the proteasome inhibitor, any compound having a proteasome inhibitory activity can be used. A proteasome inhibitor is a compound which has an affinity with a proteasome (a protease complex), and inhibits degradation of a protein by a proteasome. Therefore, a protein-degradation inducing tag may be obtained by replacing the active site of a proteasome inhibitor with another structural moiety to inactivate the proteasome inhibitory activity. Proteasome inhibitors are being studied as anticancer agents, and there are many compounds that have been approved as pharmaceutical products, or are under clinical trials. Moreover, many of proteasome inhibitors have relatively small molecular weights and low hydrophobicity, and are less problematic in terms of cell membrane permeability, cytotoxicity, and the like. For these reasons, synthesizing a protein-degradation inducing tag based on a proteasome inhibitor is quite reasonable and efficient.

Examples of the proteasome inhibitor are shown in the following Tables 8 and 9. The proteasome inhibitors shown in Tables 8 and 9 are each a 20S proteasome inhibitor having an affinity with the active center part of 20S proteasome. Furthermore, the proteasome inhibitors shown in Tables 8 and 9 naturally have affinity with 26S proteasome. However, a proteasome inhibitor which can be used for producing a protein-degradation inducing tag shall not be limited to these examples.

TABLE 8

| No. | Generic name/ Product name | Structural formula (Circles indicate active sites) | Molecular weight |
|---|---|---|---|
| 1 | Bortezomib | | 384.24 |
| 2 | ALLN (MG-101, Calpain inhibitor I | | 383.53 |

TABLE 8-continued

| No. | Generic name/ Product name | Structural formula (Circles indicate active sites) | Molecular weight |
|---|---|---|---|
| 3 | MLN9708 (Ixazomib) | | 517.12 |
| 4 | MLN2238 | | 361.03 |
| 5 | CEP-18770 | | 413.28 |
| 6 | ONO-7058 (Oprozomib) | | 532.61 |
| 7 | MG-132 | | 475.63 |

TABLE 9

| No. | Generic name/ Product name | Structural formula (Circles indicate active sites) | Molecular weight |
|---|---|---|---|
| 8 | Carfilzomib | | 719.92 |
| 9 | BSc-2118 | | 533.66 |
| 10 | PSI | | 604.75 |
| 11 | Epoxomicin | | 554.73 |
| 12 | ONX-0914 | | 580.68 |

TABLE 9-continued

| Generic name/<br>No. Product name | Structural formula<br>(Circles indicate active sites) | Molecular<br>weight |
|---|---|---|
| 13 $^{125}$I-NIP-L$_3$VS | | 720.64 |
| 14 NPI-0052<br>(Marizomib) | | 313.78 |

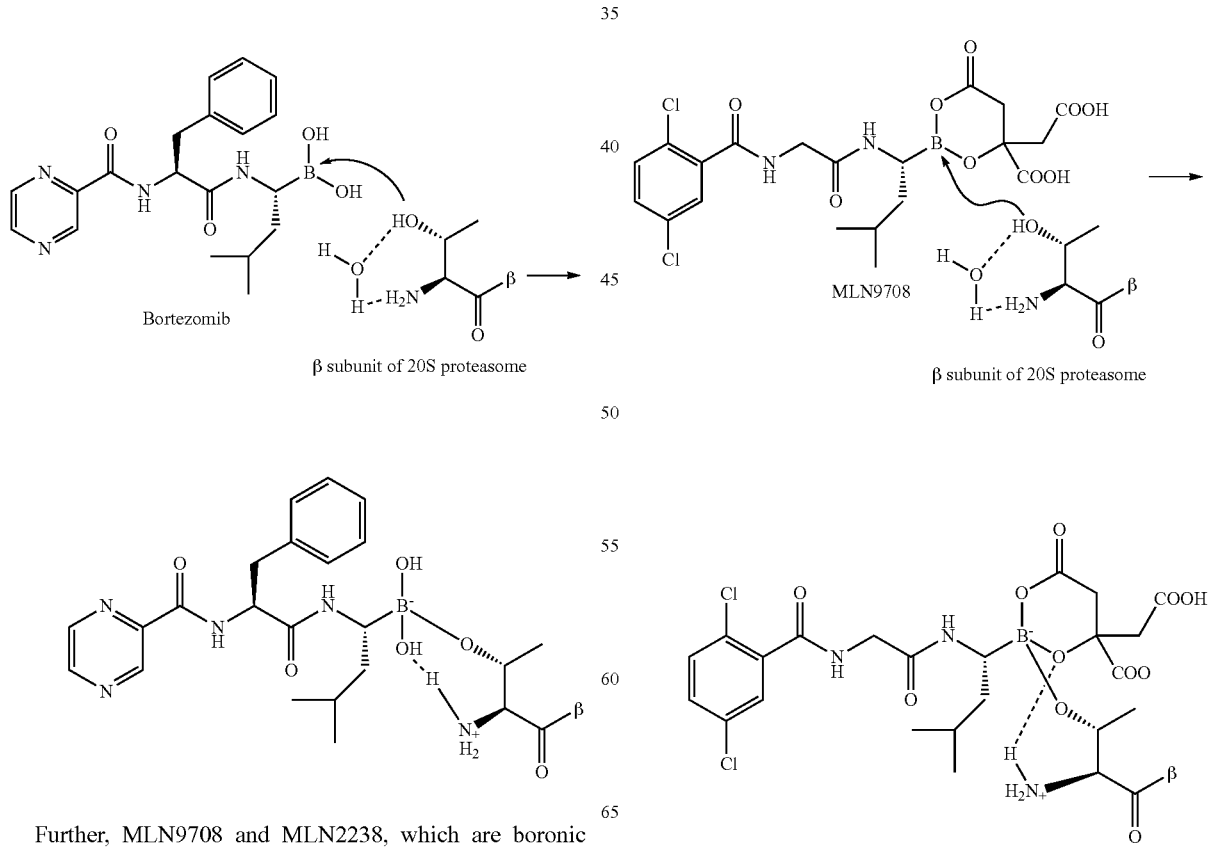

For example, bortezomib as a boronic acid-based proteasome inhibitor is known to inhibit a proteasome activity when the boronyl group as an active site covalently binds to the degradation active site of 20S proteasome as shown in the following scheme (Kisselev, A. F. et al., Chemistry & Biology, 2012, 19, 99-115).

proteasome activity when the boronic acid ester moiety or the boronyl group as an active site covalently binds to the degradation active site of 20S proteasome as shown in the following scheme (Kisselev, A. F. et al., Chemistry & Biology, 2012, 19, 99-115).

Further, MLN9708 and MLN2238, which are boronic acid-based proteasome inhibitors, are known to inhibit a

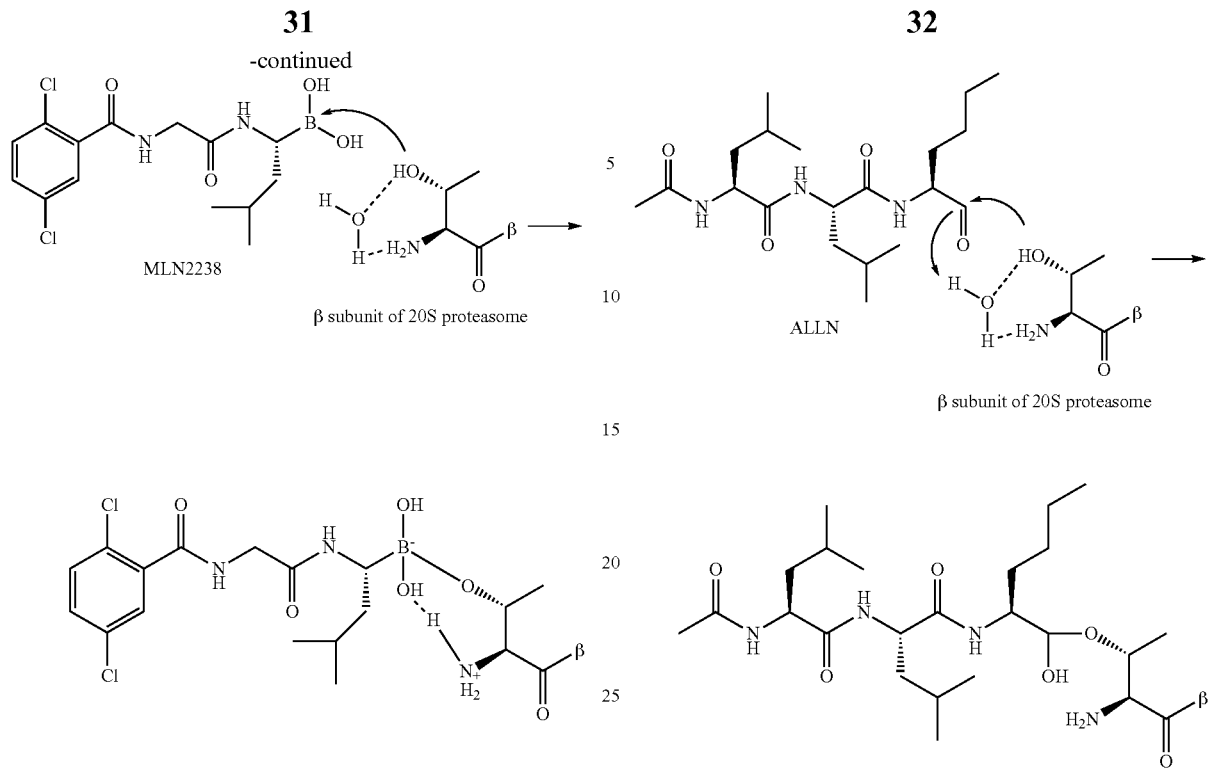

Therefore, a protein-degradation inducing tag may be obtained by replacing the boronyl group or the boronic acid ester moiety as the active sites of bortezomib, MLN9708, and MLN2238 with another structural moiety (a carboxy group, an alkyl group, an aryl group, an amino group, a hydroxy group, and the like) to inactivate the proteasome inhibitory activity.

It is noted that even for other boronic acid-based proteasome inhibitors such as CEP-18770, a protein-degradation inducing tag can be obtained by replacing the active site with another structural moiety (a carboxy group, an alkyl group, an aryl group, an amino group, a hydroxy group, and the like).

Further, ALLN, which is an aldehyde-based proteasome inhibitor, is known to inhibit a proteasome activity when the formyl group as an active site covalently binds to the degradation activity site of 20S proteasome as shown in the following scheme (Kisselev, A. F. et al., Chemistry & Biology, 2012, 19, 99-115).

Therefore, a protein-degradation inducing tag can be obtained by replacing the formyl group as the active site of ALLN with another structural moiety (a carboxy group, an alkyl group, an aryl group, an amino group, a hydroxy group, and the like) to inactivate the proteasome inhibitory activity.

It is noted that even for other aldehyde-based proteasome inhibitors such as MG-132, BSc-2118, and PSI, a protein-degradation inducing tag can be obtained by replacing the formyl group as an active site with another structural moiety (a carboxy group, an alkyl group, an aryl group, an amino group, a hydroxy group, and the like).

Examples of the protein-degradation inducing tag having a structure in which the proteasome inhibitory activity of a proteasome inhibitor is inactivated are shown in the following Tables 10 and 11. Examples of the monovalent group represented by R in the tables include a carboxy group, an alkyl group having 1 to 20 carbon atoms, an aryl group having 6 to 20 atoms, an amino group, a hydroxy group, and the like.

TABLE 10

| No. | Structural formula | |
|---|---|---|
| 1 | (structure shown) | (In the formula, R represents a monovalent group except for $\begin{array}{c}OH\\|\\B-OH\end{array}$.) |

TABLE 10-continued

| No. | Structural formula | |
|---|---|---|
| 2 | 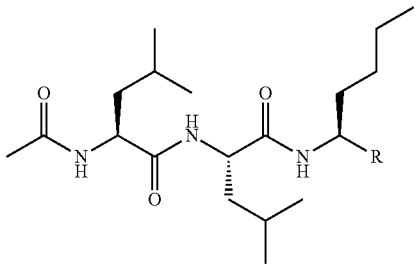 | (In the formula, R represents a monovalent group except for —CHO.) |
| 3 | 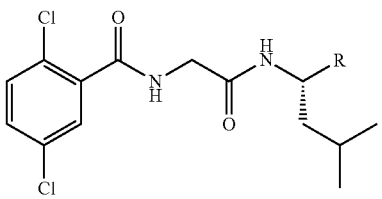 | (In the formula, R represents a monovalent group except for  and 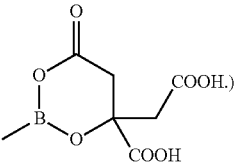.) |
| 4 | 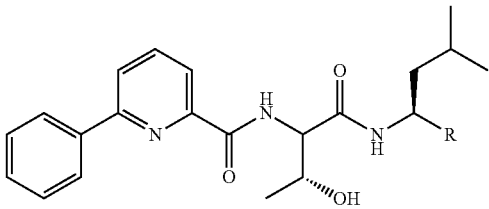 | (In the formula, R represents a monovalent group except for .) |
| 5 | 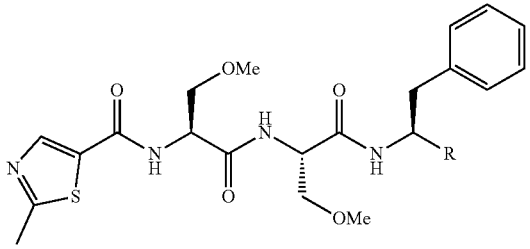 | (In the formula, R represents a monovalent group except for 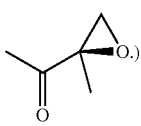.) |
| 6 | 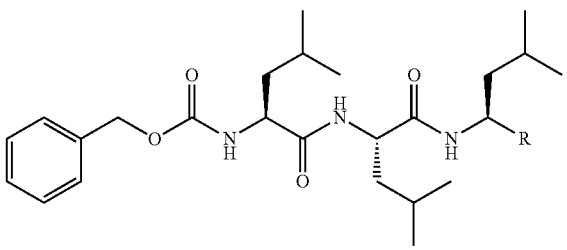 | (In the formula, R represents a monovalent group except for —CHO.) |
| 7 | 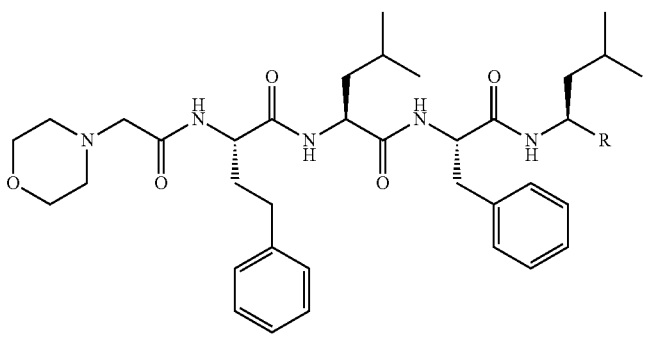 | (In the formula, R represents a monovalent group except for 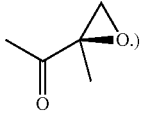.) |

TABLE 11

| No. | Structural formula | |
|---|---|---|
| 8 | [structure] | (In the formula, R represents a monovalent group except for —CHO.) |
| 9 | [structure] | (In the formula, R represents a monovalent group except for —CHO.) |
| 10 | [structure] | (In the formula, R represents a monovalent group except for [epoxyketone structure].) |
| 11 | [structure] | (In the formula, R represents a monovalent group except for [epoxyketone structure].) |
| 12 | [structure] | (In the formula, R represents a monovalent group except for [vinyl sulfone structure].) |
| 13 | [structure] | (In the formula, R represents a monovalent group.) |

TABLE 11-continued

| No. | Structural formula | |
|---|---|---|
| 14 | [Structure: bicyclic compound with HO, R, O, HN, and cyclohexenyl substituents] | (In the formula, R represents a monovalent group.) |

Other examples of the proteasome inhibitor are shown in the following Tables 12 to 17. Even for these proteasome inhibitors, a protein-degradation inducing tag can be obtained by inactivating the proteasome inhibitory activity in a similar way as described above.

TABLE 12

20S proteasome inhibitor

| No. | Generic name/ Product name | Structural formula | Molecular weight |
|---|---|---|---|
| 15 | Aspirin | [Structure: aspirin with COOH and acetate group on benzene ring] | 180.15 |
| 16 | Hydroxyurea inhibitor | [Structure: adamantyl-O-phenyl-alkyne with hydroxyurea group] | 354.54 |
| 17 | PI-1840 | [Structure: propylphenoxy-acetamide with isopropyl, oxadiazole, and pyridine groups] | 394.47 |
| 18 | PI-0831 | [Structure: pyridyl-sulfonamide-phenyl-amino-chloronaphthoquinone] | 439.87 |

TABLE 12-continued

| | | 20S proteasome inhibitor | |
|---|---|---|---|
| No. | Generic name/ Product name | Structural formula | Molecular weight |
| 19 | Cerastol | | 450.61 |

TABLE 13

| | | 20S proteasome inhibitor | |
|---|---|---|---|
| No. | Generic name/ Product name | Structural formula | Molecular weight |
| 20 | CVT-659 | | 571.66 |
| 21 | Capped dipeptide 2 | | 645.15 |

TABLE 13-continued 20S proteasome inhibitor

| No. | Generic name/ Product name | Structural formula | Molecular weight |
|---|---|---|---|
| 22 | TMC95A | | 677.71 |
| 23 | Capped dipeptide 1 | | 699.80 |

TABLE 14

20S proteasome inhibitor

| No. | Generic name/ Product name | Structural formula | Molecular weight |
|---|---|---|---|
| 24 | Ritonavir | | 720.94 |

TABLE 14-continued
| | | 20S proteasome inhibitor | |
|---|---|---|---|
| No. | Generic name/ Product name | Structural formula | Molecular weight |
| 25 | Scytonemide A | 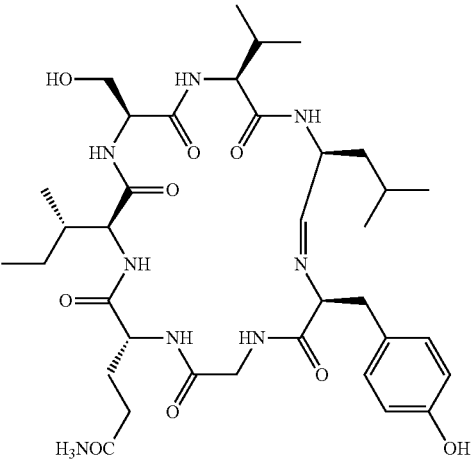 | 744.89 |
| 26 | Argyrin A | 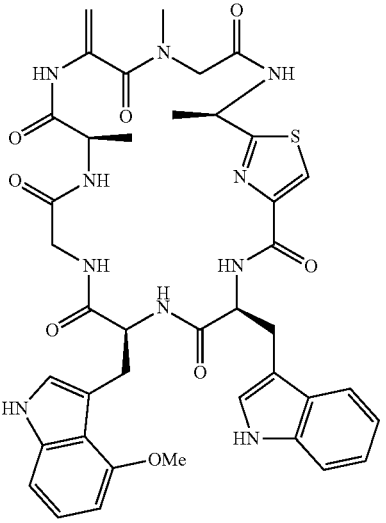 [SMILES: C=C1NC(=O)[C@@H](C)NC(=O)CNC(=O)[C@H](Cc2c[nH]c3cccc(OC)c23)NC(=O)[C@H](Cc2c[nH]c3ccccc23)NC(=O)c2csc(n2)[C@@H](C)NC(=O)CN(C)C1=O] | 824.91 |
| 27 | Benzylstatine peptide 1 | 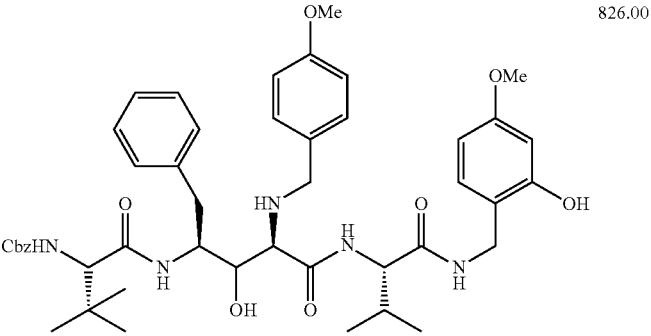 | 826.00 |

TABLE 15

| | | 19S proteasome inhibitor | |
|---|---|---|---|
| No. | Generic name/ Product name | Structural formula | Molecular weight |
| 1 | RIP-1 (Rpt4 inhibitor) | 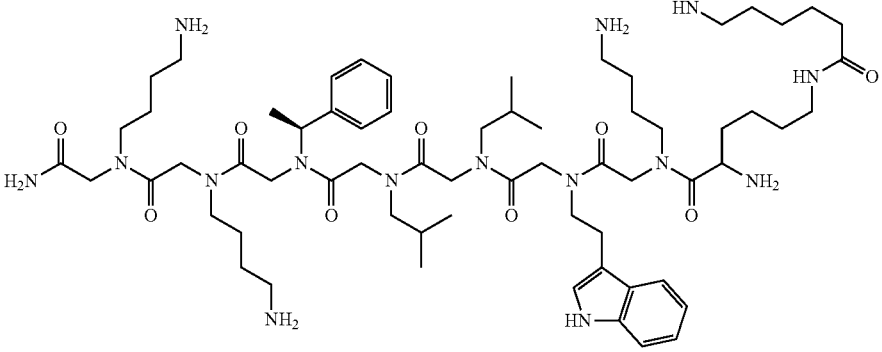 | 1348.76 |

TABLE 16

| | | Inhibitor for a constituent factor other than 20S/19S | | |
|---|---|---|---|---|
| No. | Generic name/ Product name | Structural formula | Molecular weight | Others |
| 1 | JBIR-22 | 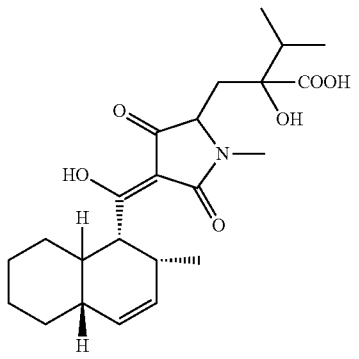 [SMILES: CC(C)C(O)(CC1C(=O)/C(=C(\O)[C@H]2C3CCCC[C@H]3C=C[C@H]2C)C(=O)N1C)C(=O)O] | 419.52 | PAC-3 (molecule assembly factor) inhibition) |

TABLE 17

| | | 20S immunoproteasome inhibitor | | |
|---|---|---|---|---|
| No. | Generic name/ Product name | Structural formula | Molecular weight | Others |
| 1 | PR-957 | 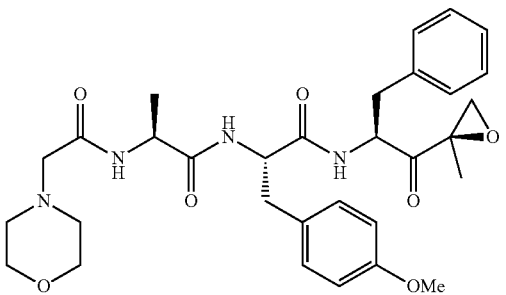 [SMILES: COc1ccc(C[C@H](NC(=O)[C@H](C)NC(=O)CN2CCOCC2)C(=O)N[C@@H](Cc2ccccc2)C(=O)[C@@]2(C)CO2)cc1] | 580.68 | β5i is inhibited |

TABLE 17-continued 20S immunoproteasome inhibitor

| No. | Generic name/ Product name | Structural formula | Molecular weight | Others |
|---|---|---|---|---|
| 2 | IPSI-001 | | 362.47 | β2i is inhibited |
| 3 | LMP2-sp-ek | | 484.75 | β2i is inhibited |

In another embodiment, the protein-degradation inducing tag may have a structure in which the protease inhibitory activity of a protease inhibitor (except for the proteasome inhibitors described above) is inactivated.

The term "structure in which a protease inhibitory activity is inactivated" as used herein encompasses a structure in which the protease inhibitory activity is attenuated in addition to a structure in which the protease inhibitory activity is completely eliminated. In a certain embodiment, the protein-degradation inducing tag has a 50% inhibition concentration ($IC_{50}$) against a protease as an inhibition target of a protease inhibitor which is 2 times or more of the 50% inhibition concentration ($IC_{50}$) of the original protease inhibitor.

As a protease inhibitor, any compound having a protease inhibitory activity can be used. The protease inhibitor is a compound having an affinity with a protease and inhibiting degradation of a protein by the protease. Therefore, a protein-degradation inducing tag can be obtained by replacing the active site of a protease inhibitor with another structural moiety to inactivate the protease inhibitory activity.

Examples of the protease inhibitor are shown in the following Tables 18 to 85. Protein-degradation inducing tags can be obtained by replacing the active sites of these protease inhibitors with other structural moieties to inactivate the protease inhibitory activities. However, a protease inhibitor which can be used for producing protein-degradation inducing tags shall not be limited to these examples. Existing data bases (for example, "MEROPS-the peptidase database" (merops.sanger.ac.uk/index.shtml) and the like) can be consulted for information about proteases and protease inhibitors if needed.

TABLE 18

β-secretase inhibitor

| No. | Name | Structural formula | Molecular weight | Protease to be inhibited |
|---|---|---|---|---|
| 1 | OM99-2 | | 892.99 | |

TABLE 19

γ-secretase inhibitor

| No. | Name | Structural formula | Molecular weight | Protease to be inhibited |
|-----|------|--------------------|------------------|--------------------------|
| 1 | γ-Secretase inhibitor | 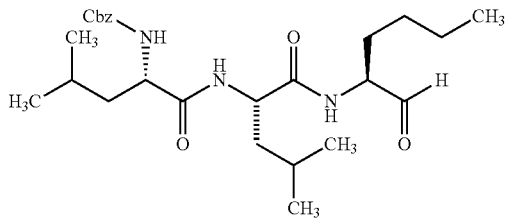 [SMILES: CCCC[C@@H](C=O)NC(=O)[C@H](CC(C)C)NC(=O)[C@H](CC(C)C)NC(=O)OCc1ccccc1] | 705.83 | |
| 2 | L-685,458 | 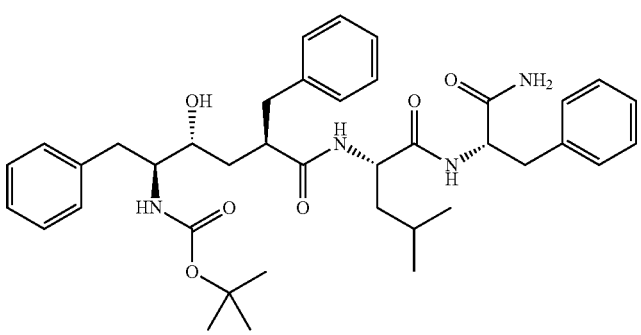 [SMILES: CC(C)C[C@H](NC(=O)[C@H](Cc1ccccc1)C[C@@H](O)[C@H](Cc1ccccc1)NC(=O)OC(C)(C)C)C(=O)N[C@@H](Cc1ccccc1)C(N)=O] | 672.85 | |

TABLE 20

Aminopeptidase inhibitor

| No. | Name | Structural formula | Molecular weight | Protease to be inhibited |
|-----|------|--------------------|------------------|--------------------------|
| 1 | Cysteamine | 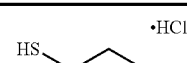 | 113.61 | |
| 2 | Bestatin | 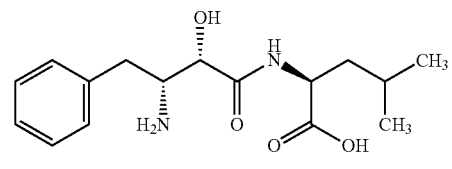 | 344.83 | Aminopeptidase B Leucine aminopeptidase |

TABLE 21

Angiotensin converting enzyme inhibitor

| No. | Name | Structural formula | Molecular weight | Protease to be inhibited |
|-----|------|--------------------|------------------|--------------------------|
| 1 | Captopril | 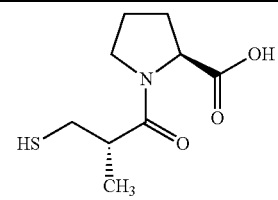 | 217.29 | Formation of angiotensin II is inhibited |

TABLE 21-continued

Angiotensin converting enzyme inhibitor

| No. | Name | Structural formula | Molecular weight | Protease to be inhibited |
|---|---|---|---|---|
| 2 | Fenoldopam monohydrobromide | [structure with Cl, HO groups, bicyclic amine·HBr, phenol] | 386.67 | |
| 3 | Angiotensin Converting Enzyme Inhibitor | [pyroglutamate]-Trp-Pro-Arg-Pro-Gln-Ile-Pro-Pro-OH | 1101.26 | |

TABLE 22

Bromelain inhibitor

| No. | Name | Structural formula | Molecular weight | Protease to be inhibited |
|---|---|---|---|---|
| 1 | E-64 | [epoxysuccinyl-leucyl-agmatine structure] | 357.41 | Cathepsin B<br>Ficin<br>Papain<br>Bromelain |
| 2 | N-Ethylmaleimide | [N-ethyl maleimide structure] | 125.13 | Calpine<br>Ficin |
| 3 | N-p-Tosyl-L-phenilalanine chloromethyl ketone | [TPCK structure] | 351.85 | Papain<br>Chymotrypsin<br>Ficin<br>Bromelain |
| 4 | Sodium iodoacetate | [ICH$_2$COONa] | 207.93 | Carboxypeptidase P<br>Bromelain<br>Ficin<br>Cathepsin |

TABLE 23

| | | Calpain inhibitor | | |
|---|---|---|---|---|
| No. | Name | Structural formula | Molecular weight | Protease to be inhibited |
| 1 | E-64c | | 314.38 | |
| 2 | E-64d | | 342.43 | |
| 3 | Z-Leu-Leu-Leu-fluoromethyl ketone | | 507.64 | |
| 4 | N-Ethylmaleimide | | 125.13 | Ficin<br>Calpine |
| 5 | Antipain dihydrochloride from microbial source | •2HCl | 677.62 | Calpine<br>Papain<br>Trypsin<br>Cathepsin A<br>Cathepsin B<br>Cathepsin D<br>Plasmin<br>Chymotrypsin<br>Pepsin<br>Granzyme B<br>Thrombin |
| 6 | 4-Chloromercuribenzoic acid | | 357.16 | Calpine<br>Carboxypeptidase<br>Clostripain |

TABLE 23-continued

Calpain inhibitor

| No. | Name | Structural formula | Molecular weight | Protease to be inhibited |
|---|---|---|---|---|
| 7 | Leupeptin | (structure shown) | 426.55 | Plasmin<br>Trypsin<br>Papain<br>Calpine<br>Cathepsin B<br>Thrombin<br>Kallikrein<br>Endoproteinase<br>Chymotrypsin<br>Proteasome (β2) |

TABLE 24

Calpain I inhibitor

| No. | Name | Structural formula | Molecular weight | Protease to be inhibited |
|---|---|---|---|---|
| 1 | Calpain Inhibitor I (ALLN, Ac-LLnL-CHO, MG-101) | (structure shown) | 383.53 | Cathepsin B<br>Cathepsin L<br>Calpine<br>Proteasome |
| 2 | Calpain Inhibitor II | (structure shown) | 401.56 | Cathepsin B<br>Calpine<br>Proteasome |

TABLE 25

Calpain II inhibitor

| No. | Name | Structural formula | Molecular weight | Protease to be inhibited |
|---|---|---|---|---|
| 1 | E-64c | (structure shown) | 314.38 | |

TABLE 25-continued

| | | Calpain II inhibitor | | |
|---|---|---|---|---|
| No. | Name | Structural formula | Molecular weight | Protease to be inhibited |
| 2 | Calpain Inhibitor I (ALLN, Ac-LLnL-CHO, MG-101) | | 383.53 | Cathepsin B Cathepsin L Calpine Proteasome |
| 3 | Calpain Inhibitor II | | 401.56 | Cathepsin B Calpine Proteasome |
| 4 | N-Ethylmaleimide | | 125.13 | Ficin Calpine |
| 5 | Antipain dihydrochloride from microbial source | •2HCl | 677.62 | Calpine Papain Trypsin Cathepsin A Cathepsin B Cathepsin D Plasmin Chymotrypsin Pepsin Granzyme B Thrombin |
| 6 | 4-Chloromercuribenzoic acid | | 357.16 | Calpine Carboxypeptidase Clostripain |

TABLE 25-continued

| | | Calpain II inhibitor | | |
|---|---|---|---|---|
| No. | Name | Structural formula | Molecular weight | Protease to be inhibited |
| 7 | Leupeptin | (structure shown) | 426.55 | Plasmin<br>Trypsin<br>Papain<br>Calpine<br>Cathepsin B<br>Thrombin<br>Kallikrein<br>Endoproteinase<br>Chymotrypsin<br>Proteasome (β2) |

TABLE 26

| | | Carboxypeptidase A/B inhibitor | | |
|---|---|---|---|---|
| No. | Name | Structural formula | Molecular weight | Protease to be inhibited |
| 1 | Ethylene glycol-bis(2-aminoethyl ether)-N,N,N',N'-tetraacetic acid | (structure shown) | 380.35 | Carboxypeptidase A<br>Carboxypeptidase B |
| 2 | EDTA disodium salt | (structure shown)<br>R = H or Na (2:2) | 372.24 | Carboxypeptidase A<br>Carboxypeptidase B<br>Dispase<br>Collagenase |
| 3 | Pentetic acid (DETAPAC, DTPA) | (structure shown) | 393.35 | Carboxypeptidase A<br>Carboxypeptidase B |
| 4 | 1,10-Phenanthroline monohydrate | (structure shown) ·H₂O | 198.22 | Carboxypeptidase A<br>Carboxypeptidase B<br>Dispase<br>Leucine aminopeptidase<br>Thermolysin |

TABLE 27

Carboxypeptidase P inhibitor

| No. | Name | Structural formula | Molecular weight | Protease to be inhibited |
|---|---|---|---|---|
| 1 | Diisopropylfluorophosphate | 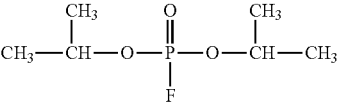 | 184.15 | Carboxypeptidase Chymotrypsin Complement Elastase Endoproteinase Kallikrein Plasmin Thrombin Pronase Proteinase |
| 2 | 4-Chloromercuribenzoic acid | 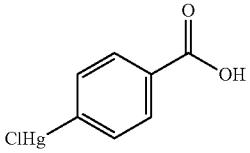 | 357.16 | Calpine Carboxypeptidase Clostripain |
| 3 | Diethyl pyrocarbonate (DEP) | 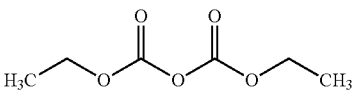 | 162.14 | |
| 4 | Sodium iodoacetate | 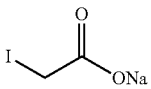 | 207.93 | Carboxypeptidase P Bromelain Ficin Cathepsin |

TABLE 28

Carboxypeptidase Y inhibitor

| No. | Name | Structural formula | Molecular weight | Protease to be inhibited |
|---|---|---|---|---|
| 1 | Diisopropylfluorophosphate | 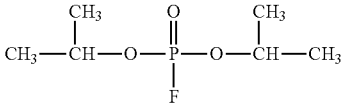 | 184.15 | Carboxypeptidase Chymotrypsin Complement Elastase Endoproteinase Kallikrein Plasmin Thrombin Pronase Proteinase |
| 2 | Phenylmethanesulfonyl fluoride | 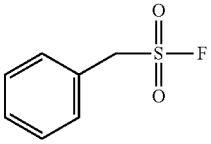 [SMILES: O=S(=O)(F)Cc1ccccc1] | 174.19 | Thrombin Elastase Plasmin Proteinase |

TABLE 29

Cathepsin B inhibitor

| No. | Name | Structural formula | Molecular weight | Protease to be inhibited |
|---|---|---|---|---|
| 1 | CA-074 | 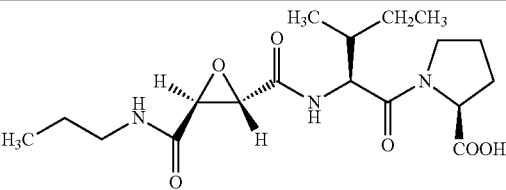 [SMILES: CCCNC(=O)[C@H]1O[C@@H]1C(=O)N[C@H](C(=O)N1CCC[C@H]1C(=O)O)C(C)CC] | 383.44 | |

TABLE 29-continued

| | | Cathepsin B inhibitor | | |
|---|---|---|---|---|
| No. | Name | Structural formula | Molecular weight | Protease to be inhibited |
| 2 | CA-074 methyl ester | | 397.47 | |
| 3 | E-64 | | 357.41 | Cathepsin B<br>Ficin<br>Papain<br>Bromelain |
| 4 | Z-Phe-Phe-fluoromethyl ketone (Z-FF-FMK) | | 462.51 | |
| 5 | Antipain dihydrochloride from microbial source | | 677.62 | Calpine<br>Papain<br>Trypsin<br>Cathepsin A<br>Cathepsin B<br>Cathepsin D<br>Plasmin<br>Chymotrypsin<br>Pepsin |

TABLE 30

Cathepsin B inhibitor

| No. | Name | Structural formula | Molecular weight | Protease to be inhibited |
|---|---|---|---|---|
| 6 | Calpain Inhibitor I (ALLN, Ac-LLnL-CHO, MG-101) | [structure] | 383.53 | Cathepsin B<br>Cathepsin L<br>Calpine<br>Proteasome |
| 7 | Calpain Inhibitor II | [structure] | 401.56 | Cathepsin B<br>Calpine<br>Proteasome |
| 8 | Chymostatin | [structure]<br>Chymostation A X = Leu<br>Chymostation B X = Val<br>Chymostation C X = Ile | A: MW = 607.7<br>B: MW = 593.7<br>C: MW = 607.7 | A: Chymotrypsin Papain<br>B: Chymotrypsin-like serine proteinase<br>C: Cathepsin A, B, C, B, H, L |
| 9 | Leupeptin | [structure] | 426.55 | Plasmin<br>Trypsin<br>Papain<br>Calpine<br>Cathepsin B<br>Thrombin<br>Kallikrein<br>Endoproteinase<br>Chymotrypsin<br>Proteasome (β2) |

TABLE 31

Cathepsin C inhibitor

| No. | Name | Structural formula | Molecular weight | Protease to be inhibited |
|---|---|---|---|---|
| 1 | Sodium iodoacetate | [structure] | 207.93 | Carboxypeptidase P<br>Bromelain<br>Ficin<br>Cathepsin |

TABLE 32

| | | Cathepsin D inhibitor | | |
|---|---|---|---|---|
| No. | Name | Structural formula | Molecular weight | Protease to be inhibited |
| 1 | Antipain dihydrochloride from microbial source | 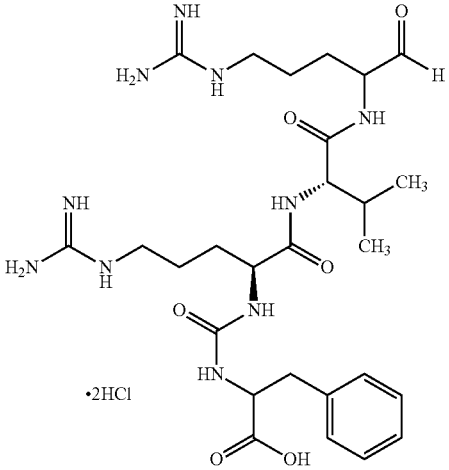 [SMILES: CC(C)[C@H](NC(=O)[C@H](CCCNC(=N)N)NC(=O)NC(Cc1ccccc1)C(=O)O)C(=O)NC(C=O)CCCNC(=N)N] | 677.62 | Calpine<br>Papain<br>Trypsin<br>Cathepsin A<br>Cathepsin B<br>Cathepsin D<br>Plasmin<br>Chymotrypsin<br>Pepsin<br>Granzyme B<br>Thrombin |
| 2 | Chymostatin | 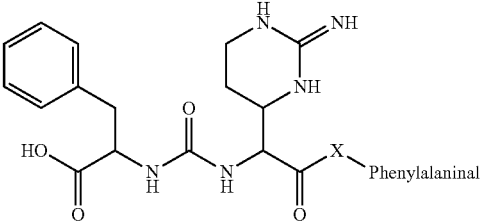  Chymostation A X = Leu<br>Chymostation B X = Val<br>Chymostation C X = Ile | A: MW = 607.7<br>B: MW = 593.7<br>C: MW = 607.7 | Chymotrypsin<br>Papain<br>Chymotrypsin-like serine proteinase<br>Cathepsin A, B, C, B, H, L<br>Proteasome ($\beta$5) |
| 3 | Pepstatin A | 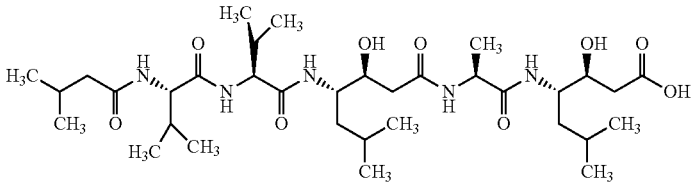 [SMILES: CC(C)CC(=O)N[C@H](C(=O)N[C@H](C(=O)N[C@@H](CC(C)C)[C@@H](O)CC(=O)N[C@@H](C)C(=O)N[C@@H](CC(C)C)[C@@H](O)CC(=O)O)C(C)C)C(C)C] | 685.89 | Pepsin<br>Cathepsin |

TABLE 33

| | | Cathepsin L inhibitor | | |
|---|---|---|---|---|
| No. | Name | Structural formula | Molecular weight | Protease to be inhibited |
| 1 | Z-Phe-Phe-fluoromethyl ketone (Z-FF-FMK) | 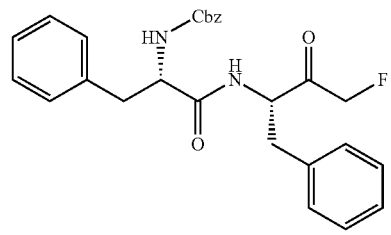 [SMILES: O=C(N[C@@H](Cc1ccccc1)C(=O)N[C@@H](Cc1ccccc1)C(=O)CF)OCc1ccccc1] | 462.51 | |

TABLE 33-continued

Cathepsin L inhibitor

| No. | Name | Structural formula | Molecular weight | Protease to be inhibited |
|---|---|---|---|---|
| 2 | Calpain Inhibitor I (ALLN, Ac-LLnL-CHO, MG-101) | | 383.53 | Cathepsin B<br>Cathepsin L<br>Calpine<br>Proteasome |

TABLE 34

Chymotrypsin inhibitor

| No. | Name | Structural formula | Molecular weight | Protease to be inhibited |
|---|---|---|---|---|
| 1 | Diisopropyl-fluorophosphate | | 184.15 | Carboxypeptidase<br>Chymotrypsin<br>Complement<br>Elastase<br>Endoproteinase<br>Kallikrein<br>Plasmin<br>Thrombin<br>Pronase<br>Proteinase |
| 2 | 4-(2-Aminoethyl) benzenesulfonyl fluoride hydrochloride (AEBSF) | | 239.69 | Plasmin<br>Trypsin<br>Chymotrypsin |
| 3 | 6-Aminocaproic acid | | 131.17 | |
| 4 | Chymostatin | Chymostation A X = Leu<br>Chymostation B X = Val<br>Chymostation C X = Ile | A: MW = 607.7<br>B: MW = 593.7<br>C: MW = 607.7 | Chymotrypsin<br>Papain<br>Chymotrypsin-like serine proteinase<br>Cathepsin A, B, C, B, H, L<br>Proteasome (β5) |

TABLE 35

| | | Chymotrypsin inhibitor | | |
|---|---|---|---|---|
| No. | Name | Structural formula | Molecular weight | Protease to be inhibited |
| 1 | N-p-Tosyl-L-phenylalanine chloromethyl ketone | | 351.85 | Papain Chymotrypsin Ficin Bromelain |
| 2 | Bromoenol lactone | | 317.18 | |
| 3 | Gabexate mesylate | | 417.48 | |
| 4 | Leupeptin | | 426.55 | Plasmin Trypsin Papain Calpine Cathepsin B Thrombin Kallikrein Endoproteinase Chymotrypsin Proteasome (β2) |

TABLE 36

| | | Clostripain inhibitor | | |
|---|---|---|---|---|
| No. | Name | Structural formula | Molecular weight | Protease to be inhibited |
| 1 | 4-Chloromercuribenzoic acid | | 357.16 | Calpine Carboxypeptidase Clostripain |

TABLE 36-continued

| | | Clostripain inhibitor | | |
|---|---|---|---|---|
| No. | Name | Structural formula | Molecular weight | Protease to be inhibited |
| 2 | Nα-Tosyl-L-lysine chloromethyl ketone hydrochloride | | 369.31 | |

TABLE 37

| | | Collagenase inhibitor | | |
|---|---|---|---|---|
| No. | Name | Structural formula | Molecular weight | Protease to be inhibited |
| 1 | EDTA disodium salt | R = H or Na (2:2), ·2H$_2$O | 372.24 | Carboxypeptidase A<br>Carboxypeptidase B<br>Dispase<br>Collagenase |
| 2 | Dichloromethylene diphosphonic acid disodium salt (DMDP) | | 288.86 | |

TABLE 38

| | | Complement C1r/C1s inhibitor | | |
|---|---|---|---|---|
| No. | Name | Structural formula | Molecular weight | Protease to be inhibited |
| 1 | Diisopropyl-fluorophosphate | | 184.15 | Carboxypeptidase<br>Chymotrypsin<br>Complement<br>Elastase<br>Endoproteinase<br>Kallikrein<br>Plasmin<br>Thrombin<br>Pronase<br>Proteinase |

TABLE 39

Complement factor D/B inhibitor

| No. | Name | Structural formula | Molecular weight | Protease to be inhibited |
|---|---|---|---|---|
| 1 | Diisopropyl-fluorophosphate | 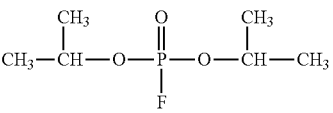 | 184.15 | Carboxypeptidase Chymotrypsin Complement Elastase Endoproteinase Kallikrein Plasmin Thrombin Pronase Proteinase |

TABLE 40

Dipeptidyl peptidase II inhibitor

| No. | Name | Structural formula | Molecular weight | Protease to be inhibited |
|---|---|---|---|---|
| 1 | Puromycin | 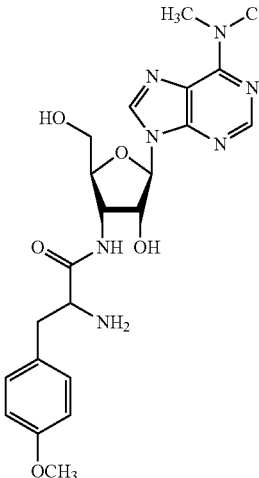 | 471.51 | Dipeptidyl peptidase II Cytosol alanyl aminopeptidase |

TABLE 41

Dipeptidyl peptidase III inhibitor

| No. | Name | Structural formula | Molecular weight | Protease to be inhibited |
|---|---|---|---|---|
| 1 | Opiorphin | 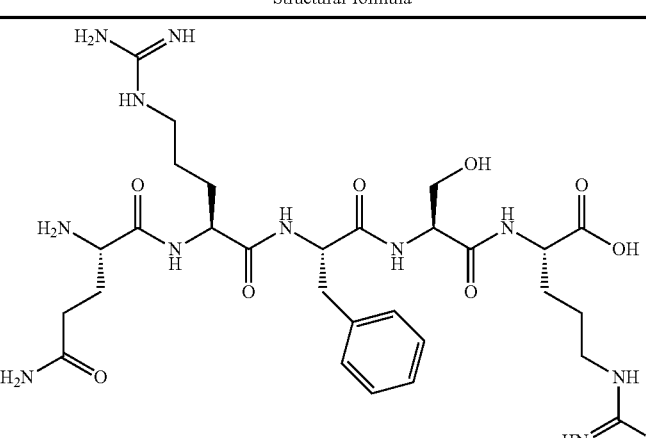 | 692.77 | Enkephalinase Neprilysin Dipeptidyl peptidase III Cytosol alanyl aminopeptidase |

TABLE 42

Dipeptidyl peptidase IV inhibitor

| No. | Name | Structural formula | Molecular weight | Protease to be inhibited |
|---|---|---|---|---|
| 1 | Ile-Pro-Ile | (structure shown) | 341.45 | Dipeptidyl peptidase IV |

TABLE 43

Dispase inhibitor

| No. | Name | Structural formula | Molecular weight | Protease to be inhibited |
|---|---|---|---|---|
| 1 | EDTA disodium salt | (structure shown) R = H or Na (2:2) · 2H$_2$O | 372.24 | Carboxypeptidase A, Carboxypeptidase B, Dispase, Collagenase |
| 2 | 1,10-Phenanthroline monohydrate | (structure shown) · H$_2$O | 198.22 | Carboxypeptidase A, Carboxypeptidase B, Dispase, Leucine aminopeptidase, Thermolysin |

TABLE 44

Elastase (granulocyte) inhibitor

| No. | Name | Structural formula | Molecular weight | Protease to be inhibited |
|---|---|---|---|---|
| 1 | N-(Methoxysuccinyl)-Ala-Ala-Pro-Val-chloromethyl ketone | H$_3$CO—(structure)—Ala-Ala-Pro-Val—Cl | 502.99 | |

TABLE 45

| | | Elastase (leukocyte) inhibitor | | |
|---|---|---|---|---|
| No. | Name | Structural formula | Molecular weight | Protease to be inhibited |
| 1 | Diisopropylfluorophosphate | (CH₃)₂CH—O—P(=O)(F)—O—CH(CH₃)₂ | 184.15 | Carboxypeptidase Chymotrypsin Complement Elastase Endoproteinase Kallikrein Plasmin Thrombin Pronase Proteinase |
| 2 | 3,4-Dichloroisocoumarin | (3,4-dichloroisocoumarin structure) | 215.03 | Thrombin Papain Plasmin |
| 3 | Phenylmethanesulfonyl fluoride | PhCH₂—S(=O)₂—F | 174.19 | Thrombin Elastase Plasmin Proteinase |

TABLE 46

| | | Elastase (pancreas) inhibitor | | |
|---|---|---|---|---|
| No. | Name | Structural formula | Molecular weight | Protease to be inhibited |
| 1 | Diisopropylfluorophosphate | (CH₃)₂CH—O—P(=O)(F)—O—CH(CH₃)₂ | 184.15 | Carboxypeptidase Chymotrypsin Complement Elastase Endoproteinase Kallikrein Plasmin Thrombin Pronase Proteinase |
| 2 | 3,4-Dichloroisocoumarin | (3,4-dichloroisocoumarin structure) | 215.03 | Thrombin Papain Plasmin |

TABLE 47

Endoproteinase Arg-C inhibitor

| No. | Name | Structural formula | Molecular weight | Protease to be inhibited |
|---|---|---|---|---|
| 1 | Diisopropylfluorophosphate | CH₃—CH(CH₃)—O—P(=O)(F)—O—CH(CH₃)—CH₃ | 184.15 | Carboxypeptidase Chymotrypsin Complement Elastase Endoproteinase Kallikrein Plasmin Thrombin Pronase Proteinase |
| 2 | 3,4-Dichloroisocoumarin | (3,4-dichloroisocoumarin structure) | 215.03 | Thrombin Papain Plasmin |

TABLE 48

Endoproteinase Glu-C inhibitor

| No. | Name | Structural formula | Molecular weight | Protease to be inhibited |
|---|---|---|---|---|
| 1 | Diisopropylfluorophosphate | CH₃—CH(CH₃)—O—P(=O)(F)—O—CH(CH₃)—CH₃ | 184.15 | Carboxypeptidase Chymotrypsin Complement Elastase Endoproteinase Kallikrein Plasmin Thrombin Pronase Proteinase |

TABLE 49

Endoproteinase Lys-C inhibitor

| No. | Name | Structural formula | Molecular weight | Protease to be inhibited |
|---|---|---|---|---|
| 1 | Diisopropylfluorophosphate | CH₃—CH(CH₃)—O—P(=O)(F)—O—CH(CH₃)—CH₃ | 184.15 | Carboxypeptidase Chymotrypsin Complement Elastase Endoproteinase Kallikrein Plasmin Thrombin Pronase Proteinase |
| 2 | 3,4-Dichloroisocoumarin | 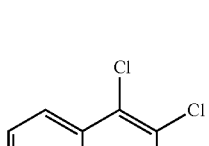 | 215.03 | Thrombin Papain Plasmin |

TABLE 49-continued

| | | Endoproteinase Lys-C inhibitor | | |
|---|---|---|---|---|
| No. | Name | Structural formula | Molecular weight | Protease to be inhibited |
| 3 | Leupeptin | 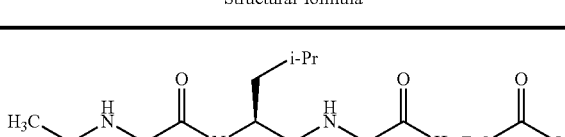 | 426.55 | Plasmin<br>Trypsin<br>Papain<br>Calpine<br>Cathepsin B<br>Thrombin<br>Kallikrein<br>Endoproteinase<br>Chymotrypsin<br>Proteasome (β2) |

TABLE 50

| | | Ficin inhibitor | | |
|---|---|---|---|---|
| No. | Name | Structural formula | Molecular weight | Protease to be inhibited |
| 1 | E-64 | | 357.41 | Cathepsin B<br>Ficin<br>Papain<br>Bromelain |
| 2 | N-Ethylmaleimide | | 125.13 | Calpine<br>Ficin |
| 3 | N-p-Tosyl-L-phenilalanine chloromethyl ketone | | 351.85 | Papain<br>Chymotrypsin<br>Ficin<br>Bromelain |
| 4 | Sodium iodoacetate | | 207.93 | Carboxypeptidase P<br>Bromelain<br>Ficin<br>Cathepsin |

TABLE 50-continued

| | | Ficin inhibitor | | |
|---|---|---|---|---|
| No. | Name | Structural formula | Molecular weight | Protease to be inhibited |
| 5 | Nα-Tosyl-L-lysine chloromethyl ketone hydrochloride | | 369.31 | |

TABLE 51

| | | Granzyme B inhibitor | | |
|---|---|---|---|---|
| No. | Name | Structural formula | Molecular weight | Protease to be inhibited |
| 1 | Antipain dihydrochloride from microbial source | | 677.62 | Calpine<br>Papain<br>Trypsin<br>Cathepsin A<br>Cathepsin B<br>Cathepsin D<br>Plasmin<br>Chymotrypsin<br>Pepsin<br>Granzyme B<br>Thrombin |
| 2 | 3,4-Dichloroisocoumarin | | 215.03 | Thrombin<br>Papain<br>Plasmin |

TABLE 52

Kallikrein (tissue) inhibitor

| No. | Name | Structural formula | Molecular weight | Protease to be inhibited |
|---|---|---|---|---|
| 1 | Diisopropylfluorophosphate | 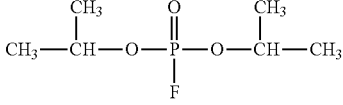 | 184.15 | Carboxypeptidase<br>Chymotrypsin<br>Complement<br>Elastase<br>Endoproteinase<br>Kallikrein<br>Plasmin<br>Thrombin<br>Pronase<br>Proteinase |
| 2 | 3,4-Dichloroisocoumarin | 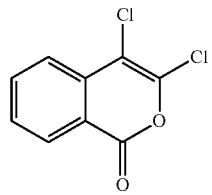 [SMILES: O=c1oc(Cl)c(Cl)c2ccccc12] | 215.03 | Thrombin<br>Papain<br>Plasmin |
| 3 | Leupeptin | 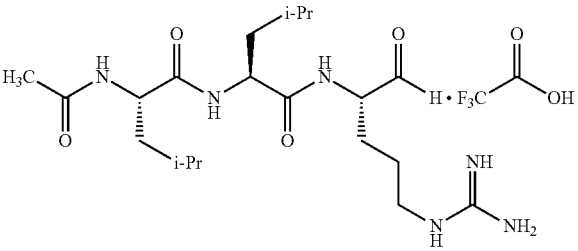 | 426.55 | Plasmin<br>Trypsin<br>Papain<br>Calpine<br>Cathepsin B<br>Thrombin<br>Kallikrein<br>Endoproteinase<br>Chymotrypsin<br>Proteasome (β2) |

TABLE 53

Kallikrein (plasma) inhibitor

| No. | Name | Structural formula | Molecular weight | Protease to be inhibited |
|---|---|---|---|---|
| 1 | Gabexate mesylate | 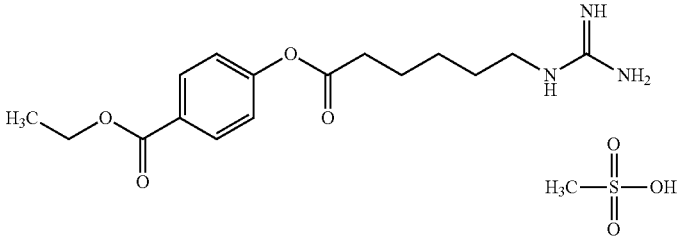 | 417.48 | |

TABLE 54

Leucine aminopeptidase inhibitor

| No. | Name | Structural formula | Molecular weight | Protease to be inhibited |
|---|---|---|---|---|
| 1 | Actinonin | | 385.5 | |
| 2 | Bestatin hydrochloride | | 344.83 | Aminopeptidase B |

TABLE 55

Leucine aminopeptidase (cytosol) inhibitor

| No. | Name | Structural formula | Molecular weight | Protease to be inhibited |
|---|---|---|---|---|
| 1 | Actinonin | | 385.5 | |
| 2 | Amastatin hydrochloride hydrate | | 511.01 (anhydrous basis) | |

TABLE 55-continued

Leucine aminopeptidase (cytosol) inhibitor

| No. | Name | Structural formula | Molecular weight | Protease to be inhibited |
|---|---|---|---|---|
| 3 | Ethylene glycol-bis(2-aminoethylether)-N,N,N',N'-tetraacetic acid | | 380.35 | |
| 4 | Ethylenediaminetetraacetic acid disodium salt dihydrate | R = H or Na (2:2) | 372.24 | |

TABLE 56

Leucine aminopeptidase (cytosol) inhibitor (Continued)

| No. | Name | Structural formula | Molecular weight | Protease to be inhibited |
|---|---|---|---|---|
| 5 | Diethylenetriaminepentaacetic acid | | 393.35 | |
| 6 | 3,4-Dichloroisocoumarin | | 215.03 | Thrombin Papain Plasmin |
| 7 | 1,10-Phenanthroline monohydrate | | 198.22 | Carboxypeptidase A Carboxypeptidase B Dispase Leucine aminopeptidase Thermolysin |

TABLE 56-continued

Leucine aminopeptidase (cytosol) inhibitor (Continued)

| No. | Name | Structural formula | Molecular weight | Protease to be inhibited |
|-----|------|--------------------|------------------|--------------------------|
| 8 | Bestatin hydrochloride | 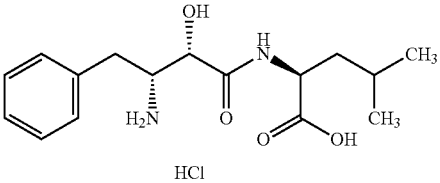 [SMILES: CC(C)C[C@H](NC(=O)[C@@H](O)[C@H](N)Cc1ccccc1)C(=O)O ; Cl] | 344.83 | Aminopeptidase B |

TABLE 57

Leucine aminopeptidase (microsome) inhibitor

| No. | Name | Structural formula | Molecular weight | Protease to be inhibited |
|-----|------|--------------------|------------------|--------------------------|
| 1 | Actinonin | 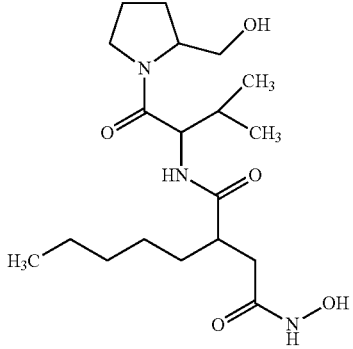 [SMILES: CCCCCC(CC(=O)NO)C(=O)NC(C(=O)N1CCCC1CO)C(C)C] | 385.5 | |
| 2 | Amastatin hydrochloride hydrate | 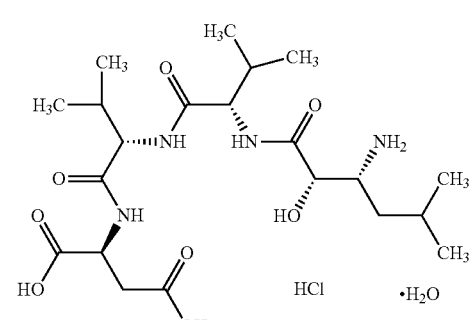 | 511.01 (anhydrous basis) | |
| 3 | Bestatin hydrochloride | 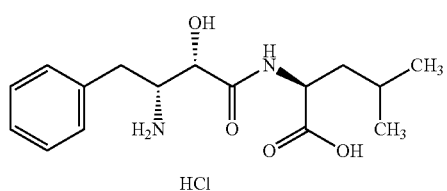 [SMILES: CC(C)C[C@H](NC(=O)[C@@H](O)[C@H](N)Cc1ccccc1)C(=O)O ; Cl] | 344.83 | Aminopeptidase B |

TABLE 58

Matrix aminopeptidase inhibitor

| No. | Name | Structural formula | Molecular weight | Protease to be inhibited |
|---|---|---|---|---|
| 1 | GM6001 | | 388.46 | |

TABLE 59

Metalloprotease inhibitor

| No. | Name | Structural formula | Molecular weight | Protease to be inhibited |
|---|---|---|---|---|
| 1 | Epiamastatin hydrochloride | | 474.55 | |

TABLE 60

Papain inhibitor

| No. | Name | Structural formula | Molecular weight | Protease to be inhibited |
|---|---|---|---|---|
| 1 | E-64 | | 357.41 | |

TABLE 60-continued

Papain inhibitor

| No. | Name | Structural formula | Molecular weight | Protease to be inhibited |
|---|---|---|---|---|
| 2 | Gly-Gly-Tyr-Arg | | 451.48 | |
| 3 | Antipain dihydrochloride from microbial source | | 677.62 | Calpine<br>Papain<br>Trypsin<br>Cathepsin A<br>Cathepsin B<br>Cathepsin D<br>Plasmin<br>Chymotrypsin<br>Pepsin<br>Granzyme B<br>Thrombin |
| 4 | Ebselen | | 274.18 | |

TABLE 61

Papain inhibitor

| No. | Name | Structural formula | Molecular weight | Protease to be inhibited |
|---|---|---|---|---|
| 5 | Chymostatin | 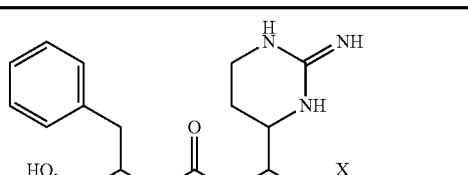<br>Chymostatin A X = Leu<br>Chymostatin B X = Val<br>Chymostatin C X = Ile | A: MW = 607.7<br>B: MW = 593.7<br>C: MW = 607.7 | Chymotrypsin<br>Papain<br>Chymotrypsin-like serine proteinase<br>Cathespin A, B, C, B, H, L<br>Proteasome (β5) |

TABLE 61-continued

Papain inhibitor

| No. | Name | Structural formula | Molecular weight | Protease to be inhibited |
|-----|------|--------------------|------------------|--------------------------|
| 6 | Cystamine dihydrochloride | $H_2N\text{-}CH_2CH_2\text{-}S\text{-}S\text{-}CH_2CH_2\text{-}NH_2 \cdot 2HCl$ | 225.2 | |
| 7 | 3,4-Dichloro-isocoumarin | (structure) | 215.03 | Thrombin<br>Papain<br>Plasmin |
| 8 | N-p-Tosyl-L-phenilalanine chloromethyl ketone | (structure) | 351.85 | Papain<br>Chymotrypsin<br>Ficin<br>Bromelain |
| 9 | Leupeptin | (structure) | 426.55 | Plasmin<br>Trypsin<br>Papain<br>Calpine<br>Cathepsin B<br>Thrombin<br>Kallikrein<br>Endoproteinase<br>Chymotrypsin<br>Proteasome ($\beta$2) |

TABLE 62

Pepsin inhibitor

| No. | Name | Structural formula | Molecular weight | Protease to be inhibited |
|-----|------|--------------------|------------------|--------------------------|
| 1 | Pepstatin A | (structure) | 685.89 | Cathepsin D |

TABLE 63

Pronase E inhibitor

| No. | Name | Structural formula | Molecular weight | Protease to be inhibited |
|-----|------|--------------------|------------------|--------------------------|
| 1 | Diisopropylfluorophosphate | (structure) | 184.15 | Carboxypeptidase<br>Chymotrypsin<br>Complement<br>Elastase<br>Endoproteinase<br>Kallikrein<br>Plasmin<br>Thrombin<br>Pronase<br>Proteinase |

TABLE 63-continued

Pronase E inhibitor

| No. | Name | Structural formula | Molecular weight | Protease to be inhibited |
|---|---|---|---|---|
| 2 | Elastatinal | | 512.56 | |
| 3 | 4-(2-Aminoethyl)benzenesulfonyl fluoride hydrochloride (AEBSF) | | 239.69 | Plasmin<br>Trypsin<br>Chymotrypsin |
| 4 | 6-Aminocaproic acid | | 131.17 | |
| 5 | Antipain dihydrochloride from microbial source | | 677.62 | Calpine<br>Papain<br>Trypsin<br>Cathepsin A<br>Cathepsin B<br>Cathepsin D<br>Plasmin<br>Chymotrypsin<br>Pepsin<br>Granzyme B<br>Thrombin |

TABLE 64

Plasmin inhibitor

| No. | Name | Structural formula | Molecular weight | Protease to be inhibited |
|---|---|---|---|---|
| 6 | 3,4-Dichloro-isocoumarin | 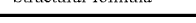 | 215.03 | Thrombin<br>Papain<br>Plasmin |

TABLE 64-continued

| | | Plasmin inhibitor | | |
|---|---|---|---|---|
| No. | Name | Structural formula | Molecular weight | Protease to be inhibited |
| 7 | Phenylmeth-anesulfonyl fluoride | | 174.19 | Thrombin<br>Elastase<br>Plasmin<br>Proteinase |
| 8 | Gabexate mesylate | | 417.48 | |
| 9 | Leupeptin | | 426.55 | Plasmin<br>Trypsin<br>Papain<br>Calpine<br>Cathepsin B<br>Thrombin<br>Kallikrein<br>Endoproteinase<br>Chymotrypsin<br>Proteasome (β2) |

TABLE 65

| | | Thrombin inhibitor | | |
|---|---|---|---|---|
| No. | Name | Structural formula | Molecular weight | Protease to be inhibited |
| 1 | Diisopro-pylfluorophos-phate | | 184.15 | Carboxypeptidase<br>Chymotrypsin<br>Complement<br>Elastase<br>Endoproteinase<br>Kallikrein<br>Plasmin<br>Thrombin<br>Pronase<br>Proteinase |
| 2 | Nα-Tosyl-L-lysine chloromethyl ketone hydrochloride | | 369.31 | |

TABLE 65-continued

Thrombin inhibitor

| No. | Name | Structural formula | Molecular weight | Protease to be inhibited |
|-----|------|-------------------|------------------|--------------------------|
| 3 | 4-(2-Aminoethyl)benzenesulfonyl fluoride hydrochloride (AEBSF) | | 239.69 | |
| 4 | Antipain dihydrochloride from microbial source | | 677.62 | Calpine<br>Papain<br>Trypsin<br>Cathepsin A<br>Cathepsin B<br>Cathepsin D<br>Plasmin<br>Chymotrypsin<br>Pepsin |

TABLE 66

Thrombin inhibitor

| No. | Name | Structural formula | Molecular weight | Protease to be inhibited |
|-----|------|-------------------|------------------|--------------------------|
| 5 | 3,4-Dichloro-isocoumarin | | 215.03 | Thrombin<br>Papain<br>Plasmin |
| 6 | Phenylmethanesulfonyl fluoride | | 174.19 | Thrombin<br>Elastase<br>Plasmin<br>Proteinase |
| 7 | Gabexate mesylate | | 417.48 | |

TABLE 66-continued

Thrombin inhibitor

| No. | Name | Structural formula | Molecular weight | Protease to be inhibited |
|---|---|---|---|---|
| 8 | Leupeptin | (structure shown) • F₃C-COOH | 426.55 | Plasmin<br>Trypsin<br>Papain<br>Calpine<br>Cathepsin B<br>Thrombin<br>Kallikrein<br>Endoproteinase<br>Chymotrypsin<br>Proteasome (β2) |

TABLE 67

Thermolysin inhibitor

| No. | Name | Structural formula | Molecular weight | Protease to be inhibited |
|---|---|---|---|---|
| 1 | Ethylene glycol-bis(2-aminoethyl ether)-N,N,N',N'-tetraacetic acid | (structure shown) | 380.35 | |
| 2 | Ethylenediaminetetraacetic acid disodium salt dihydrate | (structure shown) •2H₂O<br>R = H or Na (2:2) | 372.24 | Carboxypeptidase A<br>Carboxypeptidase B<br>Dispase<br>Collagenase |
| 3 | Diethylenetriaminepentaacetic acid | (structure shown) | 393.35 | |
| 4 | 1,10-Phenanthroline monohydrate | (structure shown) •H2O | 198.22 | Carboxypeptidase A<br>Carboxypeptidase B<br>Dispase<br>Leucine aminopeptidase<br>Thermolysin |

TABLE 67-continued

Thermolysin inhibitor

| No. | Name | Structural formula | Molecular weight | Protease to be inhibited |
|---|---|---|---|---|
| 5 | Phosphoramidon disodium salt | 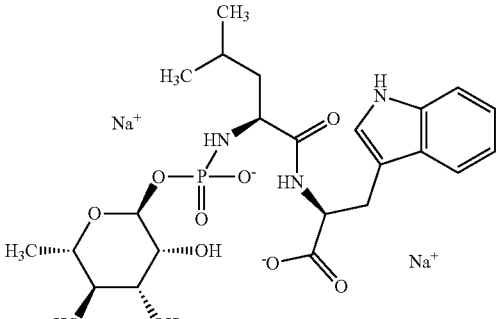 | 587.47 | |

TABLE 68

Trypsin inhibitor

| No. | Name | Structural formula | Molecular weight | Protease to be inhibited |
|---|---|---|---|---|
| 1 | 4-(2-Aminoethyl)benzenesulfonyl fluoride hydrochloride | 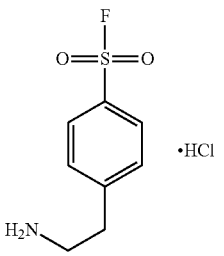 [SMILES: NCCc1ccc(S(=O)(=O)F)cc1 ; Cl] | 239.69 | Plasmin<br>Trypsin<br>Chymotrypsin |
| 2 | Antipain dihydrochloride from microbial source | 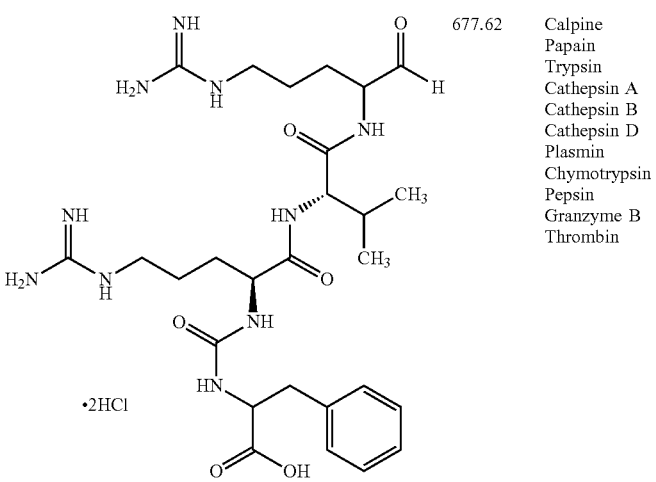 | 677.62 | Calpine<br>Papain<br>Trypsin<br>Cathepsin A<br>Cathepsin B<br>Cathepsin D<br>Plasmin<br>Chymotrypsin<br>Pepsin<br>Granzyme B<br>Thrombin |
| 3 | Boldine | 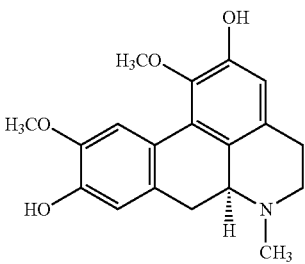 [SMILES: COc1cc2c(cc1O)C[C@H]1c3c(cc(O)c(OC)c3-2)CCN1C] | 327.37 | |

TABLE 69

| | | Pronase E inhibitor | | |
|---|---|---|---|---|
| No. | Name | Structural formula | Molecular weight | Protease to be inhibited |
| 1 | EDTA disodium salt | 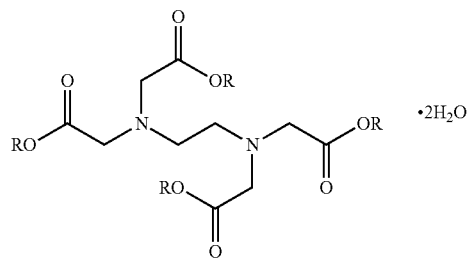 R = H or Na (2:2) ·2H$_2$O | 372.24 | Carboxypeptidase A Carboxypeptidase B Dispose Collagenase |
| 2 | Diisopropylfluorophosphate | 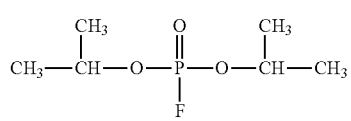 | 184.15 | Carboxypeptidase Chymotrypsin Complement Elastase Endoproteinase Kallikrein Plasmin Thrombin Pronase Proteinase |

TABLE 70

| | | Procaspase 3 inhibitor | | |
|---|---|---|---|---|
| No. | Name | Structural formula | Molecular weight | Protease to be inhibited |
| 1 | N-Acetyl-Glu-Ser-Met-Asp-al (Ac-ESMD-CHO) | 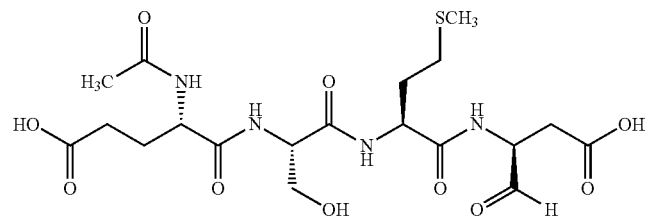 [SMILES: CSCC[C@H](NC(=O)[C@H](CO)NC(=O)[C@H](CCC(=O)O)NC(C)=O)C(=O)N[C@H](C=O)CC(=O)O] | 506.53 | |
| 2 | N-Acetyl-Ile-Glu-Thr-Asp-al (Ac-IETD-CHO) | 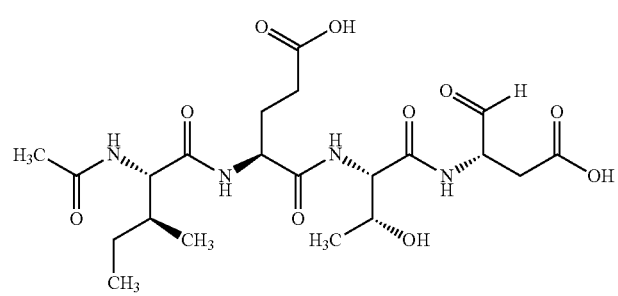 [SMILES: CC[C@H](C)[C@H](NC(C)=O)C(=O)N[C@@H](CCC(=O)O)C(=O)N[C@H](C(=O)N[C@H](C=O)CC(=O)O)[C@@H](C)O] | 502.52 | |

TABLE 71

Proteinase K inhibitor

| No. | Name | Structural formula | Molecular weight | Protease to be inhibited |
|---|---|---|---|---|
| 1 | Phenylmethanesulfonyl fluoride | | 174.19 | Thrombin<br>Elastase<br>Plasmin<br>Proteinase |
| 2 | Diisopropylfluorophosphate | | 184.15 | Carboxypeptidase<br>Chymotrypsin<br>Complement<br>Elastase<br>Endoproteinase<br>Kallikrein<br>Plasmin<br>Thrombin<br>Pronase<br>Proteinase |

TABLE 72

Renin inhibitor

| No. | Name | Structural formula | Molecular weight | Protease to be inhibited |
|---|---|---|---|---|
| 1 | Pepstatin A | | 685.89 | Cathepsin D |

TABLE 73

Caspase inhibitor

| No. | Name | Structural formula | Molecular weight | Protease to be inhibited |
|---|---|---|---|---|
| 1 | Boc-Asp(OMe)-fluoromethyl ketone (Boc-D-FMK) | | 263.26 | |
| 2 | Z-Ala-Glu(OMe)-Val-Asp(OMe)-fluoromethyl ketone (Z-AEVD-FMK) | | 610.63 | |

TABLE 74

Caspase 1 inhibitor

| No. | Name | Structural formula | Molecular weight | Protease to be inhibited |
|---|---|---|---|---|
| 1 | N-Acetyl-Trp-Glu-His-Asp-al (Ac-WEHD-CHO) | | 611.6 | |

TABLE 75

Caspase 2 inhibitor

| No. | Name | Structural formula | Molecular weight | Protease to be inhibited |
|---|---|---|---|---|
| 1 | N-Acetyl-Val-Asp-Val-Ala-Asp-CHO (Ac-VDVAD-CHO) | | 543.52 | |
| 2 | Z-Val-Asp(O-Me)-Val-Ala-Asp(O-Me)fluoromethyl ketone (Z-VDVAD-FMK) | | 695.73 | |

TABLE 76

Caspase 3 inhibitor

| No. | Name | Structural formula | Molecular weight | Protease to be inhibited |
|---|---|---|---|---|
| 1 | N-Acetyl-Glu-Ser-Met-Asp-al (Ac-ESMD-CHO) | | 506.53 | |

TABLE 76-continued

Caspase 3 inhibitor

| No. | Name | Structural formula | Molecular weight | Protease to be inhibited |
|---|---|---|---|---|
| 2 | Z-Asp(OMe)-Gln-Met-Asp(OMe) fluoromethyl ketone | | 685.72 | |
| 3 | N-Acetyl-Asp-Glu-Val-Asp-al (Ac-DEVD-CHO) | | 502.47 | |
| 4 | N-Acetyl-Ile-Glu-Thr-Asp-al (Ac-IETD-CHO) | | 502.52 | |

TABLE 77

Caspase 5 inhibitor

| No. | Name | Structural formula | Molecular weight | Protease to be inhibited |
|---|---|---|---|---|
| 1 | N-Acetyl-Trp-Glu-His-Asp-al (Ac-WEHD-CHO) | | 611.6 | |

TABLE 78

Caspase 6 inhibitor

| No. | Name | Structural formula | Molecular weight | Protease to be inhibited |
|---|---|---|---|---|
| 1 | N-Acetyl-Val-Glu-Ile-Asp-al | | 500.54 | |
| 2 | Z-Asp(OMe)-Gln-Met-Asp(OMe) fluoromethyl ketone | | 685.72 | |
| 3 | Z-Val-Glu(O-Me)-Ile-Asp(O-Me)fluoro-methyl ketone | | 652.71 | |

TABLE 79

Caspase 7 inhibitor

| No. | Name | Structural formula | Molecular weight | Protease to be inhibited |
|---|---|---|---|---|
| 1 | Z-Asp(O-Me)-Glu(O-Me)-Val-Asp(O-Me)fluoeo-methyl ketone (Z-DEVD-FMK) | | 668.66 | |

TABLE 80

Caspase 8 inhibitor

| No. | Name | Structural formula | Molecular weight | Protease to be inhibited |
|-----|------|--------------------|------------------|--------------------------|
| 1 | Z-Ile-Glu(O-Me)-Thr-Asp(O-Me)fluoromethyl ketone (Z-IETD-FMK) | | 654.68 | |
| 2 | Z-Leu-Glu(OMe)-Thr-Asp(OMe)-fluoromethyl ketone (Z-LETD-FMK) | | 655.69 | |
| 3 | N-Acetyl-Ile-Glu-Thr-Asp-al (Ac-IETD-CHO) | | 502.52 | |

TABLE 81

Caspase 9 inhibitor

| No. | Name | Structural formula | Molecular weight | Protease to be inhibited |
|-----|------|--------------------|------------------|--------------------------|
| 1 | Z-Leu-Glu(O-Me)-His-Asp(O-Me)fluoromethyl ketone (Z-LE(OMe)HD(OMe)-FMK, Z-LEHD-FMK) | | 690.72 | |

TABLE 82

Caspase 13 inhibitor

| No. | Name | Structural formula | Molecular weight | Protease to be inhibited |
|---|---|---|---|---|
| 1 | Z-Leu-Glu(OMe)-Glu(OMe)-Asp(OMe)-fluoromethyl ketone (Z-LEED-FMK) | 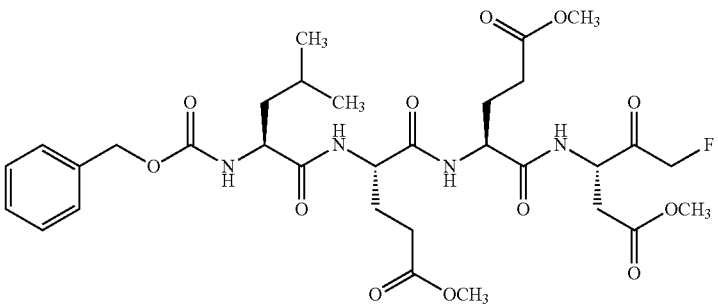 [SMILES: COC(=O)CC[C@H](NC(=O)[C@H](CCC(=O)OC)NC(=O)[C@H](CC(C)C)NC(=O)OCc1ccccc1)C(=O)N[C@@H](CC(=O)OC)C(=O)CF] | 696.72 | |

TABLE 83

Cytosol alanyl aminopeptidase inhibitor

| No. | Name | Structural formula | Molecular weight | Protease to be inhibited |
|---|---|---|---|---|
| 1 | Puromycin | 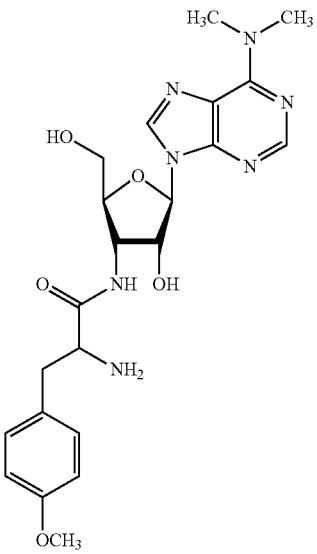 | 471.51 | Dipeptidyl peptidase II<br>Cytosol alanyl aminopeptidase |
| 2 | Opiorphin | 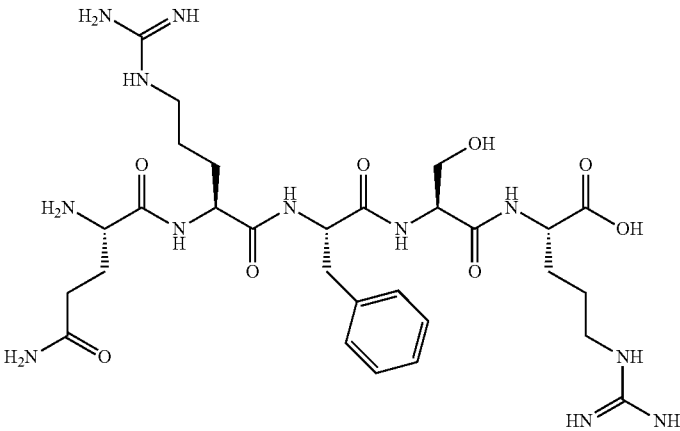 | 692.77 | Enkephalinase<br>Neprilysin<br>Dipeptidyl peptidase III<br>Cytosol alanyl aminopeptidase |

TABLE 84

Enkephalinase inhibitor

| No. | Name | Structural formula | Molecular weight | Protease to be inhibited |
|---|---|---|---|---|
| 1 | Opiorphin | (structure) | 692.77 | Enkephalinase<br>Neprilysin<br>Dipeptidyl peptidase III<br>Cytosol alanyl aminopeptidase |

TABLE 85

Neprilysin inhibitor

| No. | Name | Structural formula | Molecular weight | Protease to be inhibited |
|---|---|---|---|---|
| 1 | Opiorphin | (structure) | 692.77 | Enkephalinase<br>Neprilysin<br>Dipeptidyl peptidase III<br>Cytosol alanyl aminopeptidase |

It is noted that in the above descriptions, proteasome inhibitors and protease inhibitors other than the proteasome inhibitors are separately discussed for convenience, but a compound is also known which can inhibit the activities of both a proteasome and a protease other than proteasomes. Therefore, a protein-degradation inducing tag having an affinity with both a proteasome and a protease other than proteasomes can be obtained when such a compound is used.

Examples of the compound which can inhibit the activities of both a proteasome and a protease other than proteasomes are shown in the following table 86. However, the compound which can inhibit the activities of both a proteasome and a protease other than proteasomes shall not be limited to these examples.

TABLE 86

| No. | Name | Structural formula | Molecular weight | Protease to be inhibited |
|---|---|---|---|---|
| 1 | Calpain Inhibitor I (ALLN, Ac-LLnL-CHO, MG-101) | | 383.53 | Proteasome Cathepsin B Cathepsin L Calpine |
| 2 | Calpain Inhibitor II | | 401.56 | Proteasome Cathepsin B Calpine |
| 3 | Leupeptin | | 426.55 | Plasmin Trypsin Papain Calpine Cathepsin B Thrombin Kallikrein Endoproteinase Chymotrypsin Proteasome ($\beta$2) |
| 4 | Chymostatin | Chymostatin A X = Leu<br>Chymostatin B X = Val<br>Chymostatin C X = Ile | A: MW = 607.7<br>B: MW = 593.7<br>C: MW = 607.7 | Proteasome ($\beta$5) Chymotrypsin Papain Chymotrypsin-like serine proteinase Cathepsin A, B, C, B, H, L |
| 5 | clasto-Lactacystin $\beta$-lactone | | 213.23 | tripeptidyl peptidase II chlamydial protease-like activity factor |

In another embodiment, a proteasome activator can be used as a protein-degradation inducing tag. A proteasome activator is a compound having an affinity with a proteasome (a protease complex) without inhibiting degradation of a protein by the proteasome, and can be used as a protein-degradation inducing tag.

Examples of the proteasome activator are shown in the following Tables 87 to 89. However, the proteasome activator which can be used for producing a protein-degradation inducing tag shall not be limited to these examples.

TABLE 87
20S proteasome activator
| No. | Generic name/ Product name | Structural formula | Molecular weight |
|---|---|---|---|
| 1 | Oleuropein | 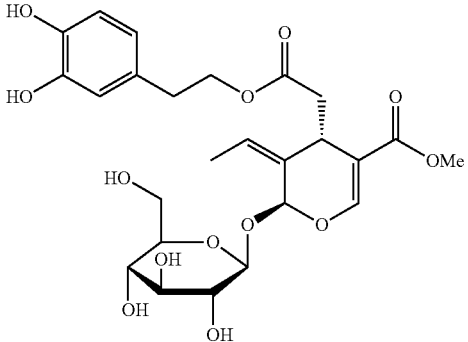 | 540.51 |
| 2 | Betulinic acid | 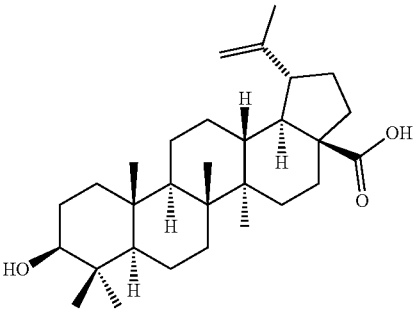 | 456.70 |
TABLE 88
19S/11S (PA28) proteasome activator
| No. | Generic name/ Product name | Structural formula | Molecular weight |
|---|---|---|---|
| 1 | IU1 (Usp 14 inhibitor) | 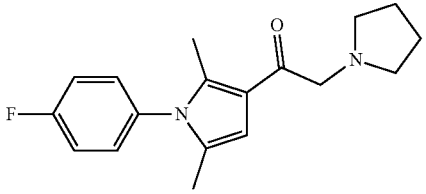 [SMILES: Cc1cc(C(=O)CN2CCCC2)c(C)n1-c1ccc(F)cc1] | 300.38 |
| 2 | b-AP-15 (Usp 14 and Uch-L5 inhibitor) | 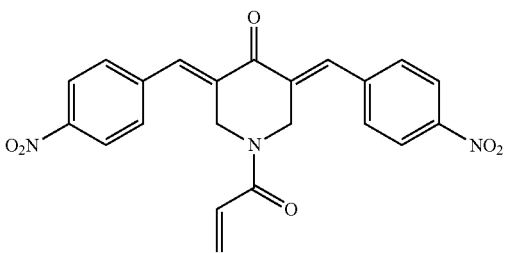 [SMILES: C=CC(=O)N1C/C(=C\c2ccc([N+](=O)[O-])cc2)C(=O)/C(=C/c2ccc([N+](=O)[O-])cc2)C1] | 419.39 |

TABLE 88-continued

19S/11S (PA28) proteasome activator

| No. | Generic name/ Product name | Structural formula | Molecular weight |
|---|---|---|---|
| 3 | 17-AAG | | 585.7 |
| 4 | PU3 | | 371.44 |
| 5 | PU-H71 | | 512.37 |
| 6 | NVP-AUY922 | | 493.60 |

TABLE 89

19S/11S (PA28) proteasome activator (Continued)

| No. | Generic name/ Product name | Structural formula | Molecular weight |
|---|---|---|---|
| 7 | SNX-5422 | | 521.54 |
| 8 | HBX 19, 818 | | 407.94 |
| 9 | LS1 | | 518.53 |
| 10 | LDN91946 | | 314.32 |
| 11 | P005091 | | 348.21 |
| 12 | P0040429 | | 484.38 |

Among the protein-degradation inducing tags as mentioned above, in particular, the protein-degradation inducing tag having an affinity with a 26S proteasome is preferable. The intracellular proteasome is generally present in a state of the 26S proteasome in which two 19S proteasomes are bonded to a 20S proteasome. Therefore, use of the protein-degradation inducing tag having an affinity with the 26S proteasome can lead the intracellular p53 protein or p53 complex to degradation more efficiently.

(Form of Conjugate of p53 Affinity Molecule and Protein-Degradation Inducing Tag)

There is no particular limitation for the form of a conjugate of the p53 affinity molecule and the protein-degradation inducing tag as long as the affinity of the p53 affinity molecule with the p53 protein or the p53 complex and the affinity of the protein-degradation inducing tag with the protease are maintained. It is noted that when both the p53 affinity molecule and the protein-degradation inducing tag are proteins, the both proteins can be fused to each other to synthesize a fusion protein, but such fusion proteins are not included in the "conjugate".

The p53 degradation inducing molecule may have, for example, a structure in which at least one p53 affinity molecule is linked to at least one protein-degradation inducing tag. The p53 degradation inducing molecule may have a structure in which one p53 affinity molecule is linked to one protein-degradation inducing tag, or may have a structure in which one p53 affinity molecule is linked to a plurality of protein-degradation inducing tags, or may have a structure in which a plurality of p53 affinity molecules are linked to one protein-degradation inducing tag, or may have a structure in which a plurality of p53 affinity molecules are linked to a plurality of protein-degradation inducing tags. In a certain embodiment, the p53 degradation inducing molecule has a structure in which one p53 affinity molecule is linked to one protein-degradation inducing tag.

A position in the p53 affinity molecule at which the protein-degradation inducing tag is linked to the p53 affinity molecule is not particularly limited as long as the affinity with the p53 protein or the p53 complex is maintained. Meanwhile, a position in the protein-degradation inducing tag at which the p53 affinity molecule is linked to the protein-degradation inducing tag is not particularly limited as long as the affinity with the protease is maintained. For example, when the protein-degradation inducing tag has, as described above, a structure in which the active site of a protease inhibitor (for example, a proteasome inhibitor) is replaced with another structural moiety, the protein-degradation inducing tag can be linked to the p53 affinity molecule at this replaced another structural moiety. Specifically, when the active site of the protease inhibitor is replaced with a carboxy group, the protein-degradation inducing tag can be linked to the p53 affinity molecule via a carboxy group.

It is noted that the p53 affinity molecule and the protein-degradation inducing tag may have a structure in which they can be linked to each other. When it is difficult to directly link the p53 affinity molecule to the protein-degradation inducing tag, it is considered that a structure capable of linking them to each other is introduced into at least one of the p53 affinity molecule and the protein-degradation inducing tag. For example, as the p53 affinity molecule, a well-known molecule having an affinity with p53 protein or p53 complex can be used, but it is assumed to be difficult to directly link this well-known molecule to the protein-degradation inducing tag. In such a case, a structure that can be linked to the protein-degradation inducing tag may be introduced into the well-known molecule, and used as the p53 affinity molecule.

<Pharmaceutical Composition>

The pharmaceutical composition of the present disclosure includes the p53 degradation inducing molecule of the present disclosure. As described above, the p53 degradation inducing molecule of the present disclosure can lead a p53 protein or a p53 complex to degradation (knockdown) by a protease (for example, a proteasome), without ubiquitination of the p53 protein or the p53 complex (in other words, in a ubiquitin-independent manner). Therefore, the pharmaceutical composition including p53 degradation inducing molecule according to the present disclosure can be used for preventing or treating p53 protein-mediated diseases or conditions. The present disclosure can also provide a method for preventing or treating p53 protein-mediated diseases or conditions. The method includes administering the pharmaceutical composition including the p53 degradation inducing molecule.

It is noted that it is difficult to design a drug targeting a complex, but the pharmaceutical composition of the present disclosure is very useful since it can degrade the p53 complex as a target.

The p53 protein-mediated diseases or conditions are not particularly limited as long as the preventive effect or therapeutic effect can be expected by the degradation of the p53 protein or the p53 complex. Examples of the p53 protein-mediated diseases or conditions are shown in Table 90. However, the p53 protein-mediated diseases or conditions shall not be limited to these examples.

TABLE 90

| | Disease or condition | References |
| --- | --- | --- |
| Cancer (Mutant-type p53 protein) | Li-Fraumeni syndrome | *Molecular Diagnosis & Therapy* vol. 17, pp. 31-47 (2013) |
| | Ovarian cancer | *Cold Spring Harbor Perspectives in Biology* vol. 2, a001008 (2010) |
| | Colorectal cancer | |
| | Esophageal cancer | |
| | Head and neck cancer | |
| | Pharyngeal cancer | |
| | Lung cancer | |
| | Skin cancer | |
| | Pancreatic cancer | |
| | Gastric cancer | |
| | Liver cancer | |
| | Cerebral tumor | |
| | Bladder cancer | |
| | Breast cancer | |
| | Uterine cancer | |
| | Soft tissue cancer | |
| | Prostate cancer | |
| | Osteosarcoma | |
| | Cervical cancer | |

TABLE 90-continued

| Disease or condition | | References |
|---|---|---|
| Senescence | Cellular senescence | Nature vol. 437, pp. 564-568 (2005) |
| | | Nature vol. 16, pp. 718-735 (2017) |
| | Fat senescence | Nature Medicine vol. 15, pp. 1082-1088 (2009) |
| Neurological disease (Neuronal cell death) | Alzheimer's disease (AD) | Biochemical and Biophysical Research Communications vol. 17, pp. 418-421 (1997) |
| | | The FASEB Journal vol. 19, pp. 255-257 (2005) |
| | | The Journal of Neuroscience, vol. 26, pp. 6377-6385 (2006) |
| | Parkinson's disease (PD) | The Journal of Biological Chemistry vol. 277, pp. 50980-58984 (2002) |
| | | Journal of Neurochemistry, vol. 100, pp. 1626-1635 (2007) |
| | | Nature Cell Biology vol. 11, pp. 1370-1375 (2009) |
| | Amyotrophic lateral sclerosis (ALS) | Neurobiology of Disease vol. 7, pp. 613-622 (2000) |
| | Angelman syndrome | Neuron vol. 21, pp. 799-811 (1998) |
| | Cerebral stroke | Cell vol. 149, pp. 1536-1548 (2012) |
| Other diseases or conditions | Diabetes | Nature Medicine vol. 15, pp. 996-997 (2009) |
| | Cardiac dysfunction | Nature vol. 446, pp. 444-448 (2007) |

In a certain embodiment, the pharmaceutical composition of the present disclosure is used for prevention or treatment of cellular senescence, fat senescence, neurological diseases (neuronal cell death), diabetes, cardiac dysfunction, and the like.

It is conventionally known that cell proliferation is suppressed and cellular senescence occurs due to telomere shortening or DNA damage. On the other hand, it has been reported that by deleting a p53 gene in a mouse model having a progeroid syndrome (Zmpste24 protease deficient mice), amelioration of senility characteristics was found in a β-galactosidase assay and the like, and extension of life was observed (Nature, 2005, 437, 564-568). It is assumed that with the pharmaceutical composition of the present disclosure, when a p53 protein or a p53 complex is degraded, prevention or amelioration of cellular senescence, and the extension of life can be achieved.

It is noted that the cellular senescence is also known to cause a variety of diseases such as myocardial infarction, atherosclerosis, and chronic obstructive pulmonary disease (Nature, 2017, 16, 718-735). According to the pharmaceutical composition of the present disclosure, it is assumed that degradation of the p53 protein or the p53 complex enables the prevention or treatment of diseases or conditions related to cellular senescence.

Furthermore, it has been reported that in neurological diseases such as Alzheimer's disease (AD), Parkinson's disease (PD), amyotrophic lateral sclerosis (ALS), and Angelman syndrome, high expression of p53 proteins is a major factor of inducing neuronal cell death (Biochemical and Biophysical Research Communications, 1997, 17, 418-21; The FASEB Journal, 2005, 19, 255-257; The Journal of Neuroscience, 2006, 26, 6377-6385; The Journal of Biological Chemistry, 2002, 277, 50980-58984; Journal of Neurochemistry, 2007, 100, 1626-1635; Nature Cell Biology, 2009, 11, 1370-1375; Neurobiology of Disease, 2000, 7, 613-622; Neuron, 1998, 21, 799-811). Furthermore, in ischemic disorders such as cerebral stroke, oxidative stress after reperfusion causes accumulation of the p53 protein in the mitochondrial matrix, and the p53 protein forms a complex with cyclophilin D, leading to the opening of the mitochondrial permeability transition pore and the induction of neuronal cell death (Cell, 2012, 149, 1536-1548). According to the pharmaceutical composition of the present disclosure, it is assumed that degradation of the p53 protein or the p53 complex enables the prevention or treatment of neurological diseases (neuronal cell death).

During the decompensated phase of heart failure (period during which symptoms progress), DNA damage, telomere shortening, and hypoxia activate the p53 gene. When the p53 gene is activated, HIF-1 (transcription factor important to induce angiogenesis factor) activity and the expression of the angiogenesis factor are deteriorated, and the heart failure is induced. On the other hand, in p53 knockout mice, in a cardiac compression added model produced by transverse aortic stenosis (TAC), there is a report that the number of blood vessels is increased, and a cardiac function can be kept (Nature, 2007, 446, 444-448). According to the pharmaceutical composition of the present disclosure, similarly, it is assumed that degradation of the p53 protein or the p53 complex enables the prevention or treatment of cardiac dysfunction.

Adipose tissue of telomerase-deficient mice shows senescence of fat (β-galactosidase positive), activation of the p53 gene, and increased production of bad adipokines (TNFα and the like). An increase in the levels of bad adipokines causes insulin resistance and makes it difficult to reduce blood glucose, leading to diabetes. On the other hand, it has been reported that deletion of the p53 gene in adipose tissue decreased the production of the bad adipokines and insulin resistance was ameliorated (Nature Medicine, 2009, 15, 996-997; Nature Medicine, 2009, 15, 1082-1088). According to the pharmaceutical composition of the present disclosure, similarly, it is assumed that degradation of the p53 protein or the p53 complex enables the prevention or treatment of diabetes.

Furthermore, mice deficient in MDM2 exhibit fetal lethality, but are known to be rescued by deletion of the p53 gene. For example, double-knockout mice without the p53 gene and the MDM2 gene are normally generated (Nature, 1995, 378, 203-206; Nature, 1995, 378, 206-208). It is assumed that the maternal administration of the pharmaceutical compositions of the present disclosure can avoid fetal lethality in MDM2-deficient fetuses by degrading the p53 protein or the p53 complex.

Preferable examples of the pharmaceutical composition of the present disclosure to be used for these applications include pharmaceutical compositions including a p53 degradation inducing molecule that is a conjugate of a p53 affinity molecule having an affinity with a wild-type (normal-type) p53 protein or a wild-type (normal-type) p53 complex and a protein-degradation inducing tag.

In another embodiment, the pharmaceutical composition of the present disclosure is used for prevention or treatment of cancer.

Conventionally, cancers in which the p53 protein is mutated are known to be resistant to chemotherapy and radiation therapy. Furthermore, in many cancers, mutants of p53 protein are known. Since the p53 gene is a tumor suppressor gene, so far, drugs for activating the wild-type p53 gene have been designed. However, when the p53 gene is mutated, p53 gene which should be a tumor suppressor gene becomes an advantage for cancerization. Therefore, degradation of the mutant p53 protein can be expected to contribute to a next-generation treatment of cancers. Furthermore, at the time of radiation therapy of cancers, the therapeutic effect is known to be improved by recovering the function of the wild-type p53 protein. It is also expected that the combination of radiation therapy and treatment using the pharmaceutical composition of the present disclosure will improve the efficacy of radiation therapy in cancers having a mutant p53 protein.

The pharmaceutical composition of the present disclosure to be used for these applications is preferably a pharmaceutical composition including a p53 degradation inducing molecule that is a conjugate of a p53 affinity molecule having an affinity with a mutant p53 protein or a mutant p53 complex and a protein-degradation inducing tag. It is noted that as the p53 affinity molecule, a molecule having higher affinity with the mutant p53 protein or the mutant p53 complex as compared with the affinity with the wild-type p53 protein or a wild-type p53 complex may be used.

The pharmaceutical composition may include a component other than the p53 degradation inducing molecule. For example, the pharmaceutical composition may include an organic or inorganic carrier which is conventionally used as a formulation material. The above carrier is formulated as an excipient, a lubricant, a binder, a disintegrating agent, and the like, in a solid preparation, and as a solvent, a solubilizing agent, a suspending agent, an isotonizing agent, a buffer agent, and the like, in a liquid preparation. Further, the pharmaceutical composition may include a formulation additive such as an antiseptic agent, an anti-oxidative agent, a coloring agent, a sweetening agent, and the like.

There is no particular limitation for the dosage form of the pharmaceutical composition. Examples of the dosage form of the pharmaceutical composition include oral preparations such as tablet, capsule, granule, powder, trochiscus, syrup, emulsion, suspension, and film preparations; parenteral preparations such injectable preparations, infusion preparations, external preparations, suppository, pellets, transnasal preparations, pulmonary preparations (inhalation), and eye drops; and the like.

The dose of the pharmaceutical composition is appropriately determined depending on the subject, route of administration, target disease, symptoms, and the like.

EXAMPLES

Below, the present invention will be described specifically with reference to Examples, but the present invention shall not be limited to these Examples. In the following Examples and Reference Examples, room temperature indicates temperatures in a range of 20° C. to 30° C.

Abbreviations of compounds used in the following Examples and Reference Examples are as follows.
H-Gly-OtBu.HCl: L-Glycine t-butyl ester hydrochloride
DMF: N,N-Dimethylformamide
DIPEA: N,N-Diisopropylethylamine
PyBOP: 1H-Benzotriazol-1-yloxy-tri(pyrrolidino)phosphonium hexafluorophosphate
TFA: Trifluoroacetic acid
H-Leu-OtBu.HCl: L-Leucine t-butyl ester hydrochloride
D-MEM: Dulbecco's modified eagle's medium
DMSO: Dimethyl sulfoxide
PBS: Phosphate buffered saline
EDTA: Ethylenediamine tetraacetic acid
SDS: Sodium dodecyl sulfate
PAGE: Polyacrylamide gel ectrophoresis
BPB: Bromophenol blue
PVDF: Polyvinylidene difluoride
TBS: Tris buffered saline
GAPDH: Glyceraldehyde 3-phosphate dehydrogenase
PMSF: Phenylmethylsulfonyl fluoride
DTT: Dithiothreitol
DEPC: Diethylpyrocarbonate
SA-β-gal: Senescence-associated beta-galactosidase
FITC: Fluorescein isothiocyanate
ec: *Escherichia coli*
DHFR: Dihydrofolate reductase
TMP: Trimethoprim
DMT-MM: 4-(4,6-Dimethoxy-1,3,5-triazin-2-yl)-4-methylmorpholinium chloride n-hydrate
AMC: 7-Amino-4-methylcoumarin
HA: Hemagglutinin
GFP: Green fluorescent protein
DsRed: *Discosoma* sp. red fluorescent protein
FBS: Fetal bovine serum Example 1

In Example 1, a p53 affinity molecule and a protein-degradation inducing tag were linked to each other to synthesize TIBC-CANDDY_MLN as a p53 degradation inducing molecule.

TIBC-NH$_2$ represented by the following formula was used as the p53 affinity molecule. TIBC-NH$_2$ is a compound obtained by adding H$_2$N—(CH$_2$)$_6$—COOH to TIBC represented by the following formula. TIBC has an affinity with a p53/MDM2 complex.

TIBC-NH₂

As the protein-degradation inducing tag, a compound (CANDDY_MLN) in which active sites of MLN9708 and MLN2238 as the proteasome inhibitors (a boronic acid ester moiety or a boronyl group) were replaced with a carboxy group was used.

The method of synthesizing TIBC-CANDDY_MLN is described in detail as follows.

(Synthesis of CANDDY_MLN)

CANDDY_MLN was synthesized according to the following synthesis scheme.

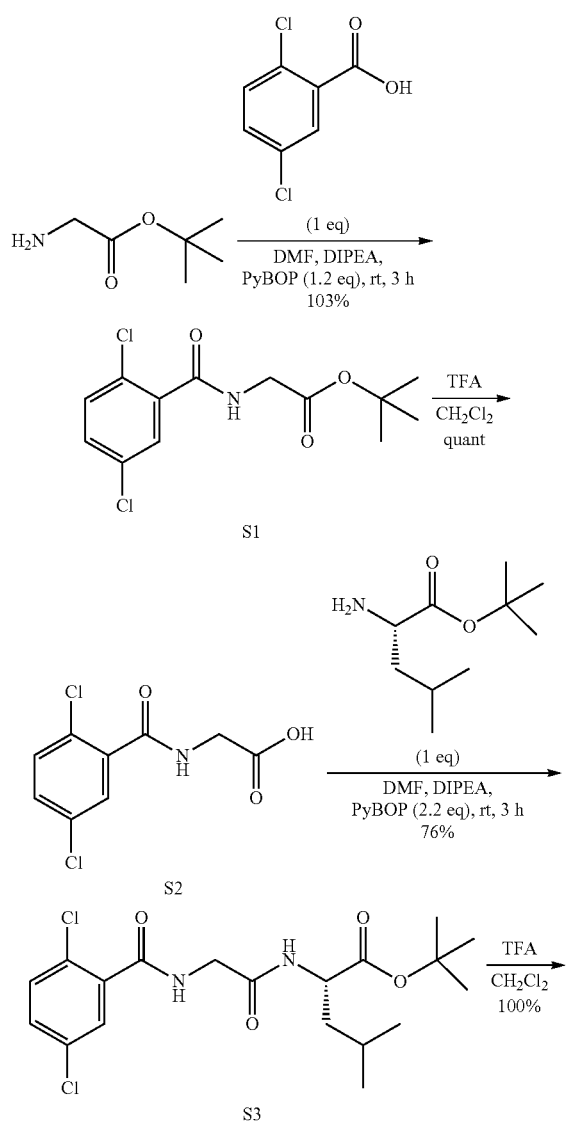

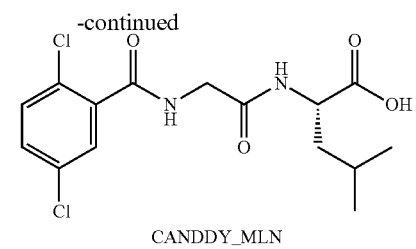

CANDDY_MLN

First, H-Gly-OtBu.HCl (286.8 mg, 1.69 mmol, 1 eq) was charged into a side-arm eggplant flask, and purged with nitrogen. Under nitrogen gas stream, 10 mL of dehydrate DMF and 5 mL of DIPEA were added, and stirred at room temperature. In 1 mL of dehydrate DMF and 1 mL of DIPEA, 2,5-dichlorobenzoic acid (309.3 mg, 1.62 mmol, 1 eq) was dissolved, which was then added to the reaction solution, and the resultant solution was stirred at room temperature for 20 minutes. PyBOP (1.02 g, 1.96 mmol, 1.2 eq) was dissolved in 1 mL of dehydrate DMF, then added to the reaction solution, and stirred at room temperature for 3 hours. The reaction solution was diluted with water and aqueous sodium hydrogen carbonate, and extracted twice with ethyl acetate/hexane (=4/1). After being dried over anhydrous sodium sulfate, the solvent was evaporated under reduced pressure. Separation and purification treatment was performed by silica gel chromatography (hexane/chloroform=1/1 to 0/1, gradient) to obtain a compound S1 (531.0 mg, 1.75 mmol, 103%).

Next, the compound S1 (212.4 mg, 0.70 mmol) was charged into an eggplant flask, and 5 mL of dichloromethane was then added. This was stirred at room temperature for 5 minutes, then 5 mL of TFA was added thereto, and the resultant solution was stirred at room temperature for one hour. After evaporating the solvent under reduced pressure, vacuum drying was performed to obtain a compound S2 (190.7 mg, quant.).

Next, the compound S2 (190.7 mg, 0.77 mmol, 1 eq) and H-Leu-OtBu.HCl (175.8 mg, 0.79 mmol, 1 eq) were charged into a side-arm eggplant flask, and purged with nitrogen. Under nitrogen gas stream, 5 mL of dehydrate DMF and 5 mL of DIPEA were added, and stirred at room temperature for 20 minutes. PyBOP (886.7 mg, 1.70 mmol, 2.2 eq) was dissolved in 1.5 mL of dehydrate DMF, then the resultant solution was added to the reaction solution and stirred at room temperature for 3 hours. The reaction solution was diluted with water and aqueous sodium hydrogen carbonate, and extracted twice with ethyl acetate/hexane (=4/1). After being dried over anhydrous sodium sulfate, the solvent was evaporated under reduced pressure. Separation and purification treatment was performed by silica gel chromatography (hexane/chloroform=1/1 to 0/1, gradient) to obtain a compound S3 (244.2 mg, 0.58 mmol, 76%).

Next, the compound S3 (240.8 mg, 0.58 mmol) was charged into an eggplant flask, and 5 mL of dichloromethane was added. This was stirred at room temperature for 5 minutes, and then 5 mL of TFA was added, and stirred at room temperature for 1 hour. After evaporating the solvent under reduced pressure, vacuum drying was performed to obtain CANDDY_MLN (214.7 mg, 0.59 mmol, 100%).

(Synthesis of TIBC-CANDDY_MLN)

TIBC-CANDDY_MLN was synthesized according to the following synthesis scheme.

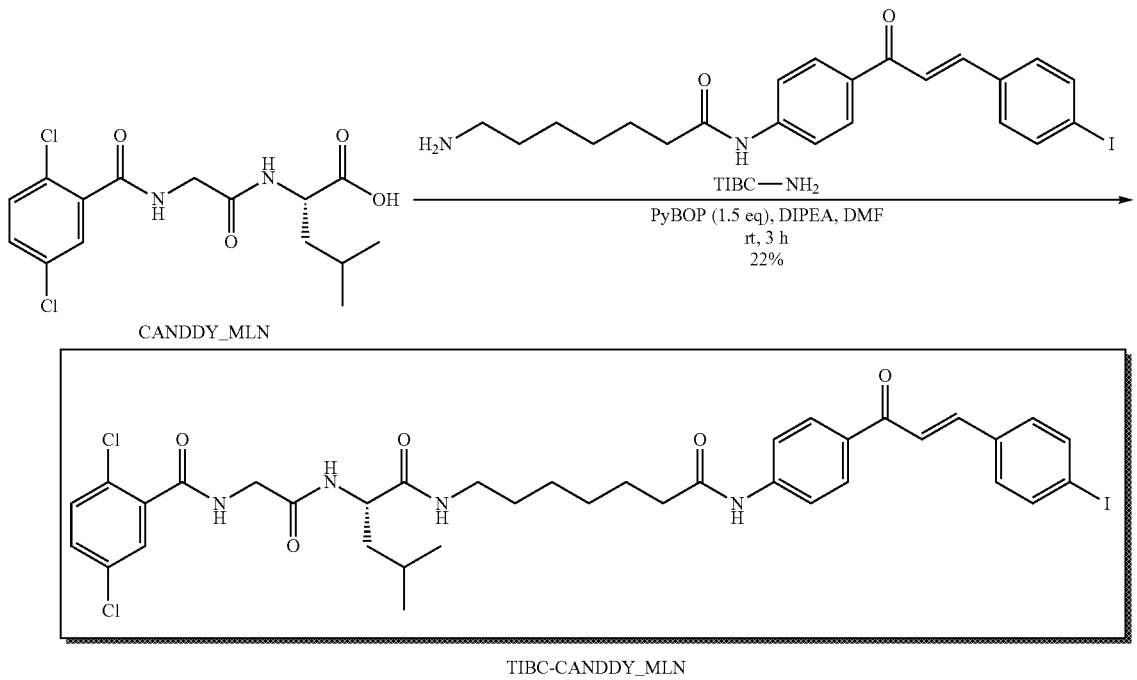

CANDDY_MLN (21.7 mg, 0.06 mmol, 1 eq) and separately synthesized TIBC-NH$_2$ (29.3 mg, 0.06 mmol, 1 eq) were charged into an eggplant flask, and 5 mL of dehydrate DMF was then added. After being stirred at room temperature for 5 minutes, 5 mL of DIPEA was then added to neutralize the solution. After the resultant solution was stirred at room temperature for 20 minutes, PyBOP (46.8 mg, 0.09 mmol, 1.5 eq) was directly added to a reaction solution, and the reaction solution was stirred at room temperature for 16 hours. Under cooling, a saturated sodium hydrogen carbonate aqueous solution was added, an organic layer was separated, and then a water layer was extracted with ethyl acetate. Organic layers were collected, and dried over anhydrous sodium sulfate. After the solvent was evaporated under reduced pressure, a separation refining process using silica gel chromatography (chloroform/methanol=20/1 to 4/1, gradient) was performed to obtain TIBC-CANDDY_MLN (10.8 mg, 0.013 mmol, 22%, isolated yield). The obtained TIBC-CANDDY_MLN was further purified by preparative thin layer chromatography (chloroform/methanol=10/1). The physical property data of TIBC-CANDDY_MLN are shown as follows. HRMS-FAB (m/z): [M+H]$^+$ calcd for $C_{37}H_{42}C_{12}N_4O_5I$, 819.1577; found, 819.1577.

Example 2

In Example 2, degradation (knockdown) of an endogenous wild-type p53 protein and MDM2 protein in HCT116 cells (human large intestinal cancer cells) to which TIBC-CANDDY_MLN had been added was evaluated by Western blot analysis.

(Cell Seeding)

HCT116 cells were seeded in a 24-well plate at a cell density of $8 \times 10^4$ cells/well, and then cultured under conditions of 37° C. and 5 vol % $CO_2$ for 16 hours.

(Addition of TIBC-CANDDY_MLN or TIBC to HCT116 Cells)

After 16 hours from cell seeding, TIBC-CANDDY_MLN or TIBC was added to HCT116 cells as follows. As a medium, a serum-free medium (37° C.) in which 1 mass % L-glutamine solution (Sigma-Aldrich) was added to D-MEM (high D-glucose, phenol red, sodium pyruvate (Wako Pure Chemical Industries, Ltd.)) was used. It is noted that the L-glutamine solution was added immediately before use. A DMSO solution containing TIBC-CANDDY_MLN or TIBC was mixed with the medium so that the concentration of DMSO was 1 vol %, and added to each well at 500 µL/well, and cultured under conditions of 37° C. and 5 vol % $CO_2$. As a control, DMSO was used.

(Evaluation of degradation (knockdown) of endogenous wild-type p53 protein and MDM2 protein through TIBC-CANDDY_MLN (Western blot analysis))

The medium was removed 48 hours after addition of TIBC-CANDDY_MLN or TIBC, and then PBS was added to wash the cells. After removing PBS, a mixed solution of a cell lysis buffer (CelLytic™ M, Sigma) and a protease inhibitor (cOmplete™ Mini, EDTA-free, Roche) was added to each well at 27 µL/well. After being allowed to stand at 4° C. for 15 minutes, cells were detached with a pipette tip on ice. A cell solution was collected in a 1.5 mL tube, and flash frozen in liquid nitrogen, and then thawed on ice. After thawing, the solution was centrifuged (at 13800 rpm×20 minutes, 4° C.), and the supernatant (cell extract) was collected.

The cell extract collected was subjected to Western blot analysis. An SDS-PAGE gel was prepared using TGX™ FastCast™ Acrylamide Kit, 12% (Bio-Rad). Electrophoresis samples were prepared in a 6×SDS-PAGE sample buffer (62.5 mM Tris-HCl pH 6.8, 2% SDS, 5% 2-mercaptoethanol, 10% glycerol, 0.25% BPB), and placed on a heat block at 95° C. for 4 minutes. Electrophoresis was performed at 160 V for 65 minutes (electrophoresis buffer; 195 mM glycine, 25 mM Tris).

After electrophoresis, proteins were transferred to a PVDF membrane (Immobion™-P, Millipore) under conditions of 100 V and 2 hours using a tank-type blotting device and a transfer buffer (25 mM Tris-HCl, 195 mM glycine, 0.01% SDS, 15% methanol). The membrane after transfer was shaken and blocked at room temperature for 30 minutes in 5% skim milk/TBS-T (100 mM Tris-HCl, 150 mM NaCl, 0.1% Tween-20, pH 7.6). After blocking, a primary antibody reaction was performed in 5% skim milk/TBS-T. As the primary antibody, an anti-p53 antibody (DO-1, SantaCruz, diluted 1500 times), an anti-MDM2 antibody (SMP14, SantaCruz, diluted 500 times), and an anti-GAPDH antibody (6C5, SantaCruz, diluted 20000 times) were used. The membrane was shaken at 4° C. overnight, and then washed with TBS-T for 5 minutes. It is noted that washing was performed three times. After the primary antibody reaction, a secondary antibody reaction was performed in 2% skim milk/TBS-T. As the secondary antibody, anti-mouse IgG (H+L) antibody (A90-116P-33, Bethyl, diluted 20000 times) was used. The membrane was shaken at room temperature for 45 minutes, and then washed with TBS-T for 5 minutes. It is noted that washing was performed three times. Further, the membrane was washed with TBS (100 mM Tris-HCl, 150 mM NaCl, pH 7.6) for 5 minutes. Subsequently, the membrane was treated with a chemiluminescence reagent Immobilon™ Western (Millipore), and then chemiluminescence was detected using a lumino image analyzer LAS-3000 (FUJIFILM Corporation).

The results of the Western blot analysis are shown in FIG. 1. As shown in FIG. 1, when TIBC-CANDDY_MLN was added, the amount of the endogenous wild-type p53 protein and MDM2 protein was reduced. On the other hand, when TIBC was added, the amount of the endogenous wild-type p53 protein and MDM2 protein was not reduced.

Example 3

In Example 3, degradation (knockdown) of an endogenous wild-type p53 protein in HeLa cells (human cervical cancer cells) to which TIBC-CANDDY_MLN has been added was evaluated by Western blot analysis. At the same time, a rescue of degradation of the p53 protein by a proteasome inhibitor (MLN2238) was evaluated.
(Cell Seeding)
HeLa cells were seeded in a 24-well plate at a cell density of $4 \times 10^4$ cells/well, and then cultured under conditions of 37° C. and 5 vol % $CO_2$ for 16 hours.
(Addition of TIBC-CANDDY_MLN to HeLa Cells)
After 16 hours from cell seeding, TIBC-CANDDY_MLN was added to HeLa cells as follows. As a medium, a serum-free medium (37° C.) in which 1 mass % L-glutamine solution (Sigma-Aldrich) was added to D-MEM (high D-glucose, phenol red, sodium pyruvate (Wako Pure Chemical Industries, Ltd.)) was used. It is noted that the L-glutamine solution was added immediately before use. A DMSO solution containing TIBC-CANDDY_MLN was mixed with the medium so that the concentration of DMSO was 1 vol %, and added to each well at 500 μL/well, and cultured under conditions of 37° C. and 5 vol % $CO_2$. As a control, DMSO was used. Furthermore, in addition to an experiment group in which a DMSO solution containing TIBC-CANDDY_MLN had been added, an experiment group in which a DMSO solution containing both TIBC-CANDDY_MLN and MLN2238, or MLN2238 had been added was prepared.
(Evaluation of Degradation (Knockdown) of Endogenous Wild-Type p53 Protein Through TIBC-CANDDY_MLN (Western Blot Analysis))

The medium was removed 24 hours after addition of TIBC-CANDDY_MLN or MLN2238, and then PBS was added to wash the cells. After removing PBS, a mixed solution of a cell lysis buffer (CelLytic™ M, Sigma) and a protease inhibitor (cOmplete™ Mini, EDTA-free, Roche) was added to each well at 27 μL/well. After being allowed to stand at 4° C. for 15 minutes, cells were detached with a pipette tip on ice. A cell solution was collected in a 1.5-mL tube, and flash frozen in liquid nitrogen, and then thawed on ice. After thawing three times, the solution was centrifuged (at 13800 rpm×20 minutes, 4° C.), and the supernatant (cell extract) was collected.

The cell extract collected was subjected to Western blot analysis. An SDS-PAGE gel was prepared using TGX™ FastCast™ Acrylamide Kit, 12% (Bio-Rad). Electrophoresis samples were prepared in a 6×SDS-PAGE sample buffer (62.5 mM Tris-HCl pH 6.8, 2% SDS, 5% 2-mercaptoethanol, 10% glycerol, 0.25% BPB), and placed on a heat block at 95° C. for 4 minutes. Electrophoresis was performed at 160 V for 65 minutes (electrophoresis buffer; 195 mM glycine, 25 mM Tris).

After electrophoresis, proteins were transferred to a PVDF membrane (Immobion™-P, Millipore) under conditions of 100 V and 2 hours using a tank-type blotting device and a transfer buffer (25 mM Tris-HCl, 195 mM glycine, 0.01% SDS, 15% methanol). The membrane after transfer was shaken and blocked at room temperature for 30 minutes in 5% skim milk/TBS-T (100 mM Tris-HCl, 150 mM NaCl, 0.1% Tween-20, pH 7.6). After blocking, a primary antibody reaction was carried out in 5% skim milk/TBS-T. As the primary antibody, an anti-p53 antibody (DO-1, SantaCruz, diluted 1000 times), and an anti-GAPDH antibody (6C5, SantaCruz, diluted 10000 times) were used. The membrane was shaken at 4° C. overnight, and then washed with TBS-T for 5 minutes. It is noted that washing was performed three times. After the primary antibody reaction, a secondary antibody reaction was performed in 2% skim milk/TBS-T. As the secondary antibody, an anti-mouse IgG (H+L) antibody (A90-116P-33, Bethyl, diluted 10000 times was used. The membrane was shaken at room temperature for 30 minutes, and then washed with TBS-T for 5 minutes. It is noted that washing was performed three times. Further, the membrane was washed with TBS (100 mM Tris-HCl, 150 mM NaCl, pH 7.6) for 5 minutes. Subsequently, the membrane was treated with a chemiluminescence reagent Immobilon™ Western (Millipore), and then chemiluminescence was detected using a lumino image analyzer LAS-3000 (FUJIFILM Corporation).

Figure 2:
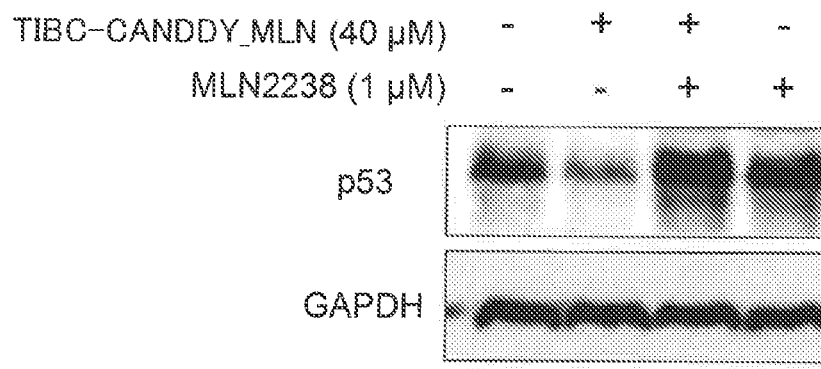
FIG. 2 shows the results of evaluation by Western blot analysis of degradation (knockdown) of an endogenous wild-type p53 protein in HeLa cells to which TIBC-CANDDY_MLN was added.

The results of the Western blot analysis are shown in FIG. 2. As shown in FIG. 2, when TIBC-CANDDY_MLN was added, the amount of the endogenous wild-type p53 protein was reduced. Furthermore, when both TIBC-CANDDY_MLN and MLN2238 were added, the amount of the wild-type p53 protein was increased as compared with the control (DMSO). The results support that TIBC-CANDDY_MLN leads the wild-type p53 protein to the degradation by a proteasome.

Example 4

In Example 4, degradation (knockdown) of the endogenous wild-type p53 protein and MDM2 protein in mouse individuals in which TIBC-CANDDY_MLN had been administered was evaluated by Western blot analysis.
(Administration of TIBC-CANDDY_MLN to Mice)

TIBC-CANDDY_MLN was dissolved in DMSO immediately before administration, and then dissolved in corn oil (Code No. 25606-55, Nacalai Tesque) so that the concentration of DMSO was 10 vol %, and then a dose of 50 mg/kg body weight or 100 mg/kg body weight was administered intraperitoneally to C57BL/6J wild-type mice (7 to 8 weeks old, male) (CLEA Japan, Inc.) (n=3). As a control, an injection carrier (corn oil containing 10 vol % DMSO) was used. The mice were kept under an environment of ad libitum access to food and water. The mice were dissected under deep anesthesia by Somnopentyl (Kyoritsu Seiyaku Corporation) 48 hours after administration. Abdominal section was performed, and then the liver was extracted and flash frozen in liquid nitrogen. Tissue frozen in liquid nitrogen was stored in a deep freezer at −80° C.
(Western Blot Analysis of Mouse Tissue)

The frozen tissue (0.04 g) was triturated, and then 980 µL of 1×TKM tissue lysis buffer (50 mM triethanolamine (pH 7.8), 50 mM KCl, 5 mM $MgCl_2$, 0.25 M sucrose, 1 mM PMSF, protein inhibitors cocktail-EDTA free (Code No. 03969-21, Nacalai Tesque), 1 mM DTT, Recombinant RNase inhibitor 5 µl/mL (40 U/µl, Cat No. 2313A, Lot No. K8402DA, TAKARA Bio)) was added, and dissolved by rotation for 15 minutes (1 rpm, 25° C.). Then, the resultant product was subjected to centrifugation (at 3000 rpm×15 minutes, 4° C.), and the supernatants (tissue extract) was collected. The concentration of proteins in the tissue extract was quantified with a spectrophotometer with the tissue extract that had been diluted 20 times using DEPC-treated water.

The tissue extract collected was subjected to Western blot analysis. An SDS-PAGE gel was prepared using TGX™ FastCast™ Acrylamide Kit, 12% (Bio-Rad). Electrophoresis samples were prepared in a 6×SDS-PAGE sample buffer (62.5 mM Tris-HCl pH 6.8, 2% SDS, 5% 2-mercaptoethanol, 10% glycerol, 0.25% BPB), and placed on a heat block at 95° C. for 5 minutes. The electrophoresis samples prepared were applied at 50 µg/well for detecting GAPDH, and at 100 µg/well for other detection. Electrophoresis was performed at 160 V for 60 minutes (electrophoresis buffer; 195 mM glycine, 25 mM Tris).

After electrophoresis, proteins were transferred to a PVDF membrane (Immobion™-P, Millipore) under conditions of 100 V and 1.5 hours using a tank-type blotting device and a transfer buffer (25 mM Tris-HCl, 195 mM glycine, 0.01% SDS, 15% methanol). The membrane after transfer was shaken and blocked in 5% skim milk/TBS-T (100 mM Tris-HCl, 150 mM NaCl, 0.1% Tween-20, pH 7.6) at room temperature for 30 minutes. After blocking, a primary antibody reaction was performed in 5% skim milk/TBS-T. As the primary antibody, an anti-p53 antibody (MAB1355, R&D Systems, Inc., diluted 500 times), an anti-MDM2 antibody (sc-965, SantaCruz, diluted 500 times), and an anti-GAPDH antibody (sc-32233, SantaCruz, diluted 20000 times) were used. The membrane was shaken at room temperature for 60 minutes, and then the membrane was washed with TBS-T for 5 minutes. It is noted that washing was performed three times. After the primary antibody reaction, a secondary antibody reaction was performed in 1% skim milk/TBS-T. The membrane was shaken at room temperature for 30 minutes, and then the membrane was washed with TBS-T for 5 minutes. It is noted that washing was performed 3 times. Furthermore, the membrane was washed with TBS (100 mM Tris-HCl, 150 mM NaCl, pH 7.6) for 10 minutes. Subsequently, the membrane was treated with a chemiluminescence reagent Immobilon™ Western (Millipore), and then chemiluminescence was detected using a lumino image analyzer LAS-3000 (FUJIFILM Corporation). Detected bands were quantified with an image processing software ImageJ (NIH).

Figure 3:
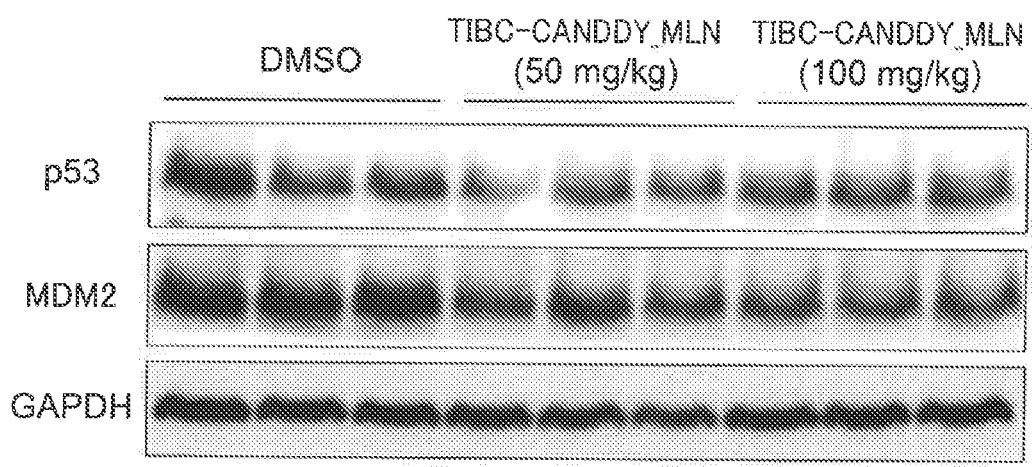
FIG. 3 shows the results of evaluation by Western blot analysis of degradation (knockdown) of a wild-type p53 protein and an MDM2 protein in a liver where TIBC-CANDDY_MLN was administered to a mouse individual.

The results of the Western blot analysis are shown in FIG. 3. As shown in FIG. 3, when TIBC-CANDDY_MLN was administered to mice in an amount of 50 mg/kg body weight or 100 mg/kg body weight, the amount of endogenous wild-type p53 protein and MDM2 protein was reduced in the liver 48 hours after the administration.

Example 5

In Example 5, an anti-aging action in a senescence-associated acidic β-galactosidase (SA-β-gal) inducing TIG3 cells (human embryonic fibroblast) in which TIBC-CANDDY_MLN had been added was evaluated by FACS analysis.
(Cell Seeding)

TIG3 cells as normal cells were seeded in a 24-well plate at a cell density of $8×10^4$ cells/well, and then cultured under conditions of 37° C. and 5 vol % $CO_2$ for 16 hours.
(Induction of SA-β-Gal by Addition of Doxorubicin to TIG3 Cells)

After 16 hours from cell seeding, doxorubicin was added to each well at 150 nM/well to induce cellular senescence. As a medium, a serum-free medium (37° C.) in which 1 mass % L-glutamine solution (Sigma-Aldrich) was added to D-MEM (high D-glucose, phenol red, sodium pyruvate (Wako Pure Chemical Industries, Ltd.)) was used. It is noted that the L-glutamine solution was added immediately before use. After the addition of doxorubicin, culture was performed under conditions of 37° C. and 5 vol % $CO_2$ for 24 hours.
(Addition of TIBC-CANDDY_MLN to Senescence-Induced TIG3 Cells)

After 24 hours from induction of senescence, TIBC-CANDDY_MLN was added to TIG3 cells as follows. As a medium, a serum-free medium (37° C.) in which 1 mass % L-glutamine solution (Sigma-Aldrich) was added to D-MEM (high D-glucose, phenol red, sodium pyruvate (Wako Pure Chemical Industries, Ltd.)) was used. It is noted that the L-glutamine solution was added immediately before use. A DMSO solution containing TIBC-CANDDY_MLN was mixed with the medium so that the concentration of DMSO was 1 vol %, and added to each well at 500 µL/well, and cultured under conditions of 37° C. and 5 vol % $CO_2$ for 48 hours. As a control, DMSO was used.
(Evaluation of Senescence Suppressing Action by TIBC-CANDDY_MLN (Facs Analysis))

For quantification of SA-β-gal as a senescence marker, a commercially available kit (Cellular Senescence Detection Kit-SPiDER-βGal (DOJINDO LABORATORIES)) was used.

After 48 hours from the addition of TIBC-CANDDY_MLN, the medium was removed, and 1 mL of D-MEM (high D-glucose, phenol red, sodium pyruvate) (Wako Pure Chemical Industries, Ltd.) was added to wash the cells. Bafilomycin A1 working solution included in the kit was added to each well at 200 µL/well, and then culture was performed under conditions of 37° C. and 5 vol % $CO_2$ for 1 hour. Next, SPiDER-βGal working solution included in the kit was added to each well at 200 µL/well, and then culture was performed under conditions of 37° C. and 5 vol % $CO_2$ for 30 minutes. After the solution was removed, 1 mL of D-MEM (high D-glucose, phenol red, sodium pyruvate) (Wako Pure Chemical Industries, Ltd.) was added to wash the cells. The medium was removed, and then trypsin (0.25 w/v % trypsin-1 mmol/L EDTA.4 Na Solution with Phenol Red) (Wako Pure Chemical Industries, Ltd.) at 37° C. was added to each well at 200 µL/well, and cultured under conditions of 37° C. and 5 vol % $CO_2$ for 1 minute. After culturing, a medium where 10 mass % FBS and 1 mass % PenStrep (100 U/mL sodium penicillin G and 100 μg/mL The method of synthesizing TMP-CANDDY_DMT is described in detail as the following synthesis scheme.

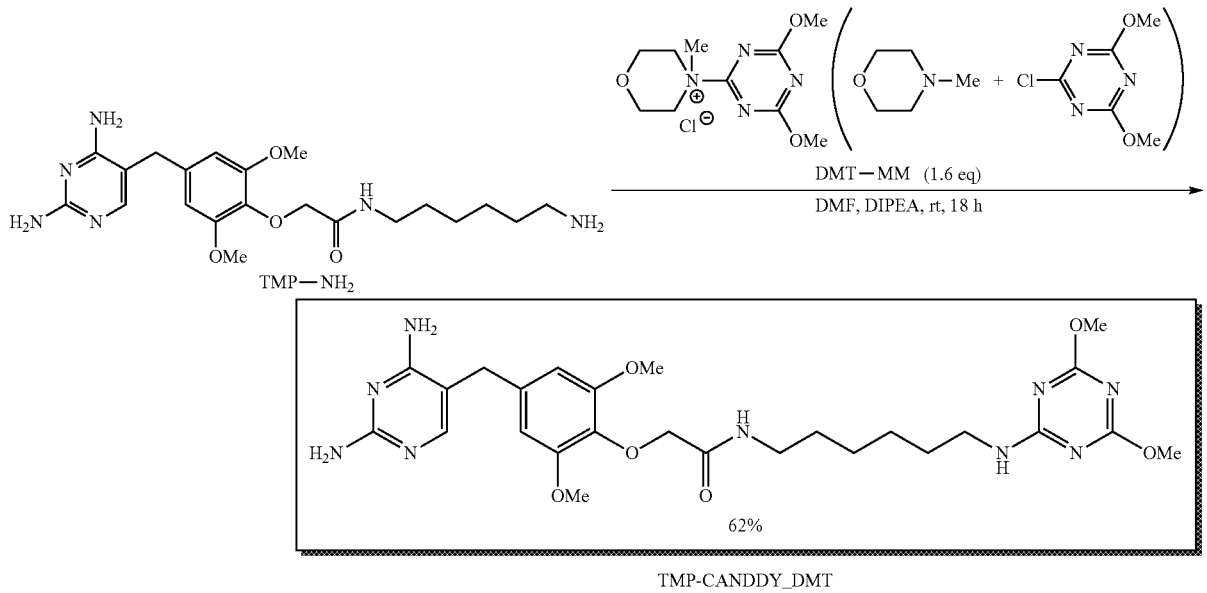

streptomycin sulfate) (Wako Pure Chemical Industries, Ltd.) were added to D-MEM (low D-glucose, L-glutamine, phenol red) (Wako Pure Chemical Industries, Ltd.) was added to each well at 300 μL/well, and suspended, and then a cell solution was collected in a 15-mL tube.

A BD FACSCanto™ II (BD Biosciences) was used for flow cytometry to detect SA-β-gal labeled with FITC. Immediately before the FACS analysis, the cell solution was passed through a mesh having a pore diameter of 32 μm, and transferred to a FACS tube. A histogram of the FITC strength was created by an analysis software FlowJo™ (TOMY Digital Biology Co., Ltd.), and the senescence suppressing action by TIBC-CANDDY_MLN was evaluated from a shift in the histogram.

Figure 4:
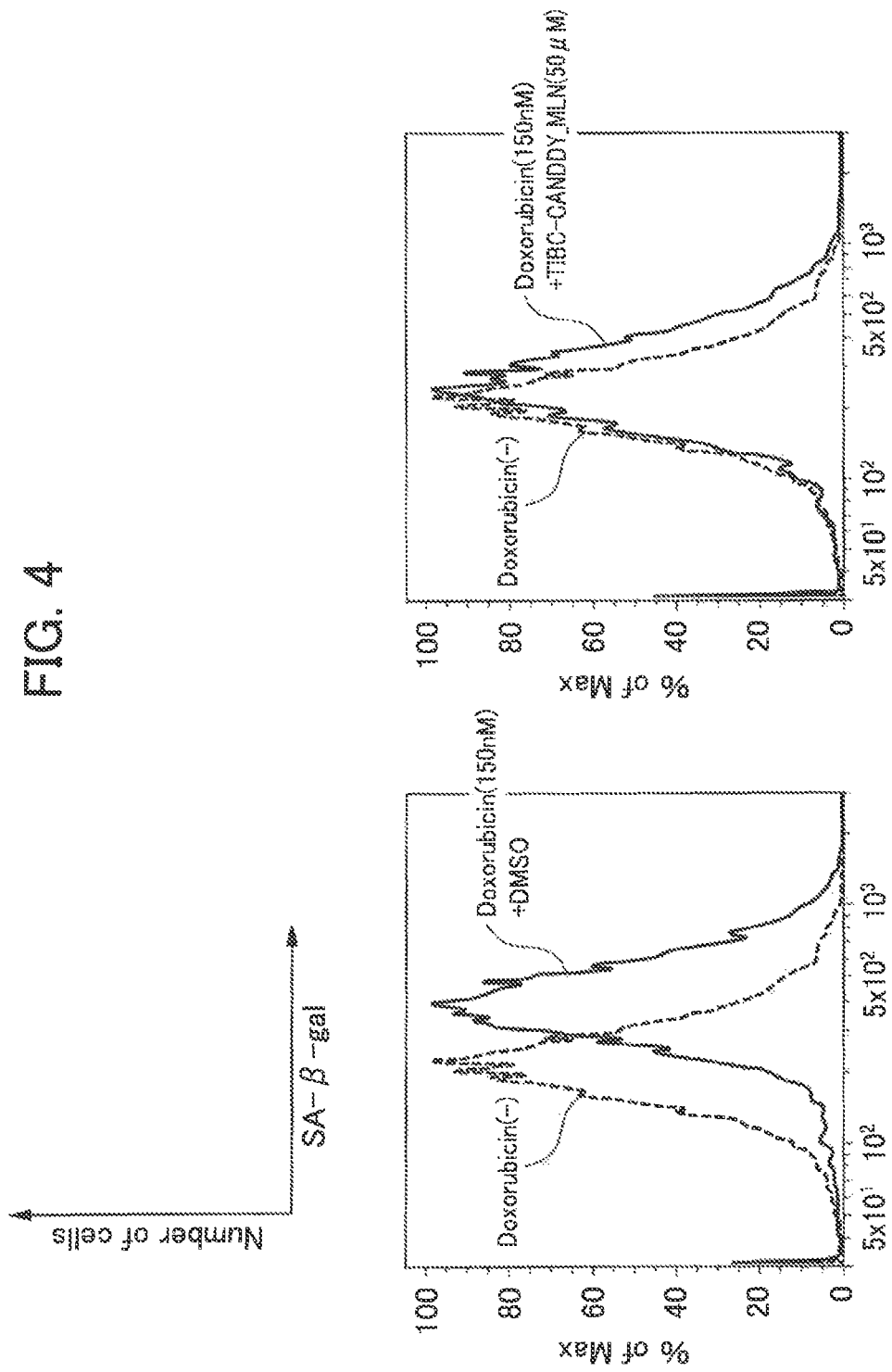
FIG. 4 shows the results of evaluation by FACS (Fluorescence Activated Cell Sorting) analysis of an anti-aging action in a senescence-associated acidic β-galactosidase (SA-β-gal) inducing TIG3 cells to which TIBC-CANDDY_MLN was added.

The results of the FACS analysis are shown in FIG. 4. As shown in FIG. 4, when doxorubicin (150 nM) was added, a shift to SA-β-gal (senescence marker) positive was observed as compared with the case where doxorubicin was not added. On the other hand, when TIBC-CANDDY_MLN (50 μM) was added after addition of doxorubicin (150 nM), a shift to SA-β-gal (senescence marker) positive was hardly observed. From these results, a cellular senescence suppressing action (about 80%) by TIBC-CANDDY_MLN was recognized.

Reference Example 1

In Reference Example 1, a protein affinity molecule and a protein-degradation inducing tag were linked to each other to synthesize TMP-CANDDY_DMT as a protein-degradation inducing molecule.

As the protein affinity molecule, a TMP derivative (TMP-$NH_2$) was used. The TMP derivative was obtained by introducing a functional group including an amino group into TMP that is a dihydrofolate reductase inhibitor to be bonded to an ecDHFR protein. Furthermore, as the protein-degradation inducing tag, a compound (DMT) in which $R^1$ and $R^2$ in the aforementioned formula (I) are each a methoxy group was used. DMT is a compound which is not derived from a proteasome inhibitor, but has an affinity with a proteasome.

TMP-$NH_2$ (Long, M. J. et al., Chem. Biol., 2012, 19 (5), 629-637) (31.7 mg, 0.073 mmol) was charged into an eggplant flask, and 0.3 mL of dehydrate DMF was added. After the resultant solution was stirred at room temperature for 10 minutes, 0.1 mL of DIPEA was added, and stirred at room temperature for 10 minutes. DMT-MM (33.6 mg, 0.12 mmol, 1.6 eq, Wako Pure Chemical Industries, Ltd.) was directly added to the reaction solution, and stirred at room temperature for 18 hours. The reaction solution was diluted with water and aqueous sodium hydrogen carbonate, and extracted with chloroform for five times. After being dried over anhydrous sodium sulfate, the solvent was evaporated under reduced pressure. Separation and purification treatment was performed by silica gel chromatography (chloroform/methanol=92/8) to obtain TMP-CANDDY_DMT (25.8 mg, 0.045 mmol, 62%, isolated yield).

Reference Example 2

In Reference Example 2, the proteasome inhibitory activity of TMP-CANDDY_DMT and the affinity of TMP-CANDDY_DMT with a proteasome were evaluated. As a positive control, MG-132 as a proteasome inhibitor was used.

For evaluation, 20S Proteasome StressXpress™ Assay Kit Gold (Bioscience) was used. AMC was measured by using Multi-Detection Microplate Reader (Synergy HT, BIO-TEK). The AMC was produced by cleaving the C-terminus of an AMC-binding proteasome fluorescence substrate specific to β subunits of a 20S proteasome, including β5 (chymotrypsin-like activity), β2 (trypsin-like activity), and β1 (caspase-like activity). The measuring wavelengths were 360 nm for excitation light (Ex.), and 460 nm for fluorescence (Em.).

Figure 5A:
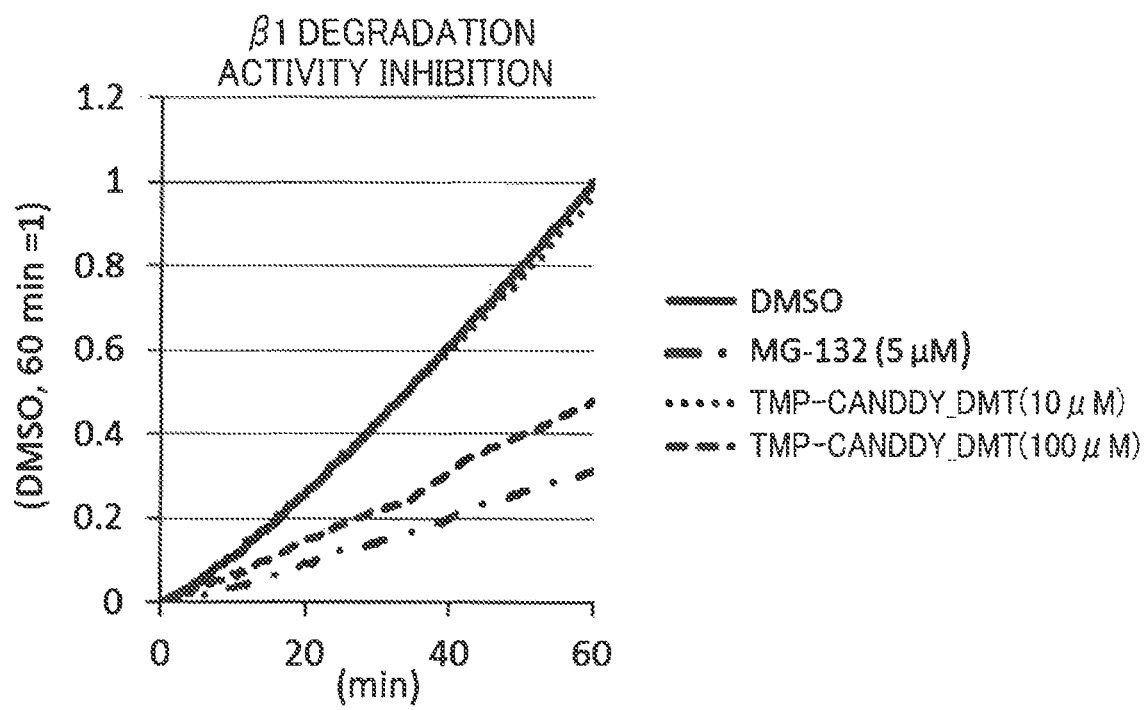
FIG. 5A shows inhibitory activity of TMP-CANDDY_DMT and MG-132 with respect to a catalytic subunit β1 of a proteasome.
Figure 5B:
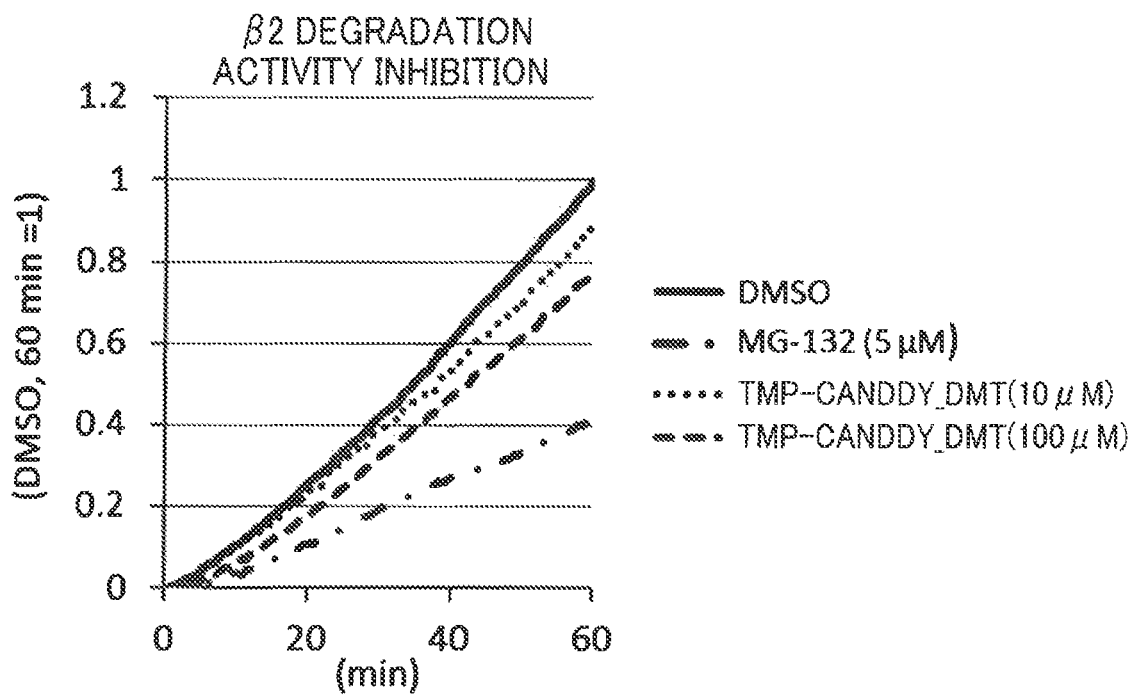
FIG. 5B shows inhibitory activity of TMP-CANDDY_DMT and MG-132 with respect to a catalytic subunit β2 of the proteasome.

FIGS. 5A to 5C show the proteasome activities against β1 (caspase-like activity), β2 (trypsin-like activity), and β5 (chymotrypsin-like activity), respectively. As can be seen in FIGS. 5A to 5C, TMP-CANDDY_DMT was found to have a significantly lower proteasome inhibitory activity as compared with MG-132. Moreover, the inhibitory activity of TMP-CANDDY_DMT was increased in a concentration dependent manner against any of β1, β2, and β5, suggesting that TMP-CANDDY_DMT has a moderate affinity with a proteasome. That is, it was evaluated that DMT has an affinity with a proteasome, and does not inhibit degradation.

Reference Example 3

In Reference Example 3, degradation (knockdown) of a forcibly expressed ecDHFR protein in HeLa cells through TMP-CANDDY_DMT was evaluated by FACS analysis.
(Preparation of Plasmid)
A plasmid (pMIR-DsRed-IRES-ecDHFR-HA-GFP) expressing an ecDHFR protein was amplified in *E. coli*, and then purified with Miniprep Kit (QIAGEN).
(Introduction of Plasmid into HeLa Cells and Cell Seeding)
A plasmid was introduced into HeLa cells to transiently overexpress an ecDHFR protein as a target protein (specifically, a fusion protein of an ecDHFR protein and GFP through a HA tag) or a DsRed protein for comparison in the cells.

ScreenFectA (Wako Pure Chemical Industries, Ltd.) as a transfection reagent was used to introduce the plasmid into HeLa cells by a routine procedure. HeLa cells into which the plasmid had been introduced were seeded in a 24-well plate at a cell density of $6 \times 10^4$ cells/well, and then cultured under conditions of 37° C. and 5 vol % $CO_2$ for 40 hours.
(Addition of TMP-CANDDY_DMT to HeLa Cells)
Culture was performed for 40 hours after introduction of the plasmid, and then TMP-CANDDY_DMT was added to HeLa cells as follows. As a medium, a serum-free medium (37° C.) in which 1 mass % L-glutamine solution (Sigma-Aldrich) was added to D-MEM (high D-glucose, phenol red, sodium pyruvate) (Wako Pure Chemical Industries, Ltd.) was used, and 297 µL of the medium was added to each well. It is noted that the L-glutamine solution was added immediately before use. A DMSO solution containing TMP-CANDDY_DMT was added to each well at 3 µL/well, and cultured under conditions of 37° C. and 5 vol % $CO_2$. As a control, a TMP-containing DMSO solution or DMSO was used.
(Evaluation of Degradation (Knockdown) of ecDHFR Protein Through TMP-CANDDY_DMT (FACS Analysis))
The medium was removed 24 hours after addition of TMP-CANDDY_DMT, and then PBS was added to wash the cells. After removing PBS, trypsin (0.25 w/v % trypsin-1 mmol/L EDTA.4 Na solution with phenol red) (Wako Pure Chemical Industries, Ltd.) at 37° C. was added to each well at 300 µL/well, and cultured under conditions of 37° C. and 5 vol % $CO_2$ for 1 minute. After culturing, a medium, in which 10 mass % FBS and 1 mass % PenStrep (100 U/mL sodium penicillin G and 100 µg/mL streptomycin sulfate) (Wako Pure Chemical Industries, Ltd.) had been added to D-MEM (low D-glucose, L-glutamine, phenol red) (Wako Pure Chemical Industries, Ltd.), was added to each well at 500 µL/well, and suspended, and then a cell solution was collected in a 15 mL tube.

The cell solution collected was centrifuged (at 1000 rpm×5 minutes, 4° C.), and the supernatant was removed, and then suspended in 2 mL of PBS (37° C.). The cell solution after suspension was centrifuged (at 1000 rpm×5 minutes, 4° C.), and the supernatant was removed, and then 500 µL of an FACS buffer (1 mass % FBS/PBS) at 4° C. was added, and allowed to stand on ice.

A BD FACSCanto™ II (BD Biosciences) was used for flow cytometry, and the expression levels of GFP and the DsRed protein in the cells were quantified. The cell solution was passed through a mesh with a pore size of 32 µm, and transferred to an FACS tube immediately before FACS analysis. The GFP/DsRed ratio per cell was computed using an analysis software FlowJo™ (TOMY Digital Biology Co., Ltd.), and the degradation (knockdown) of the ecDHFR protein by TMP-CANDDY_DMT was determined from a shift in a graph.

Figure 6:
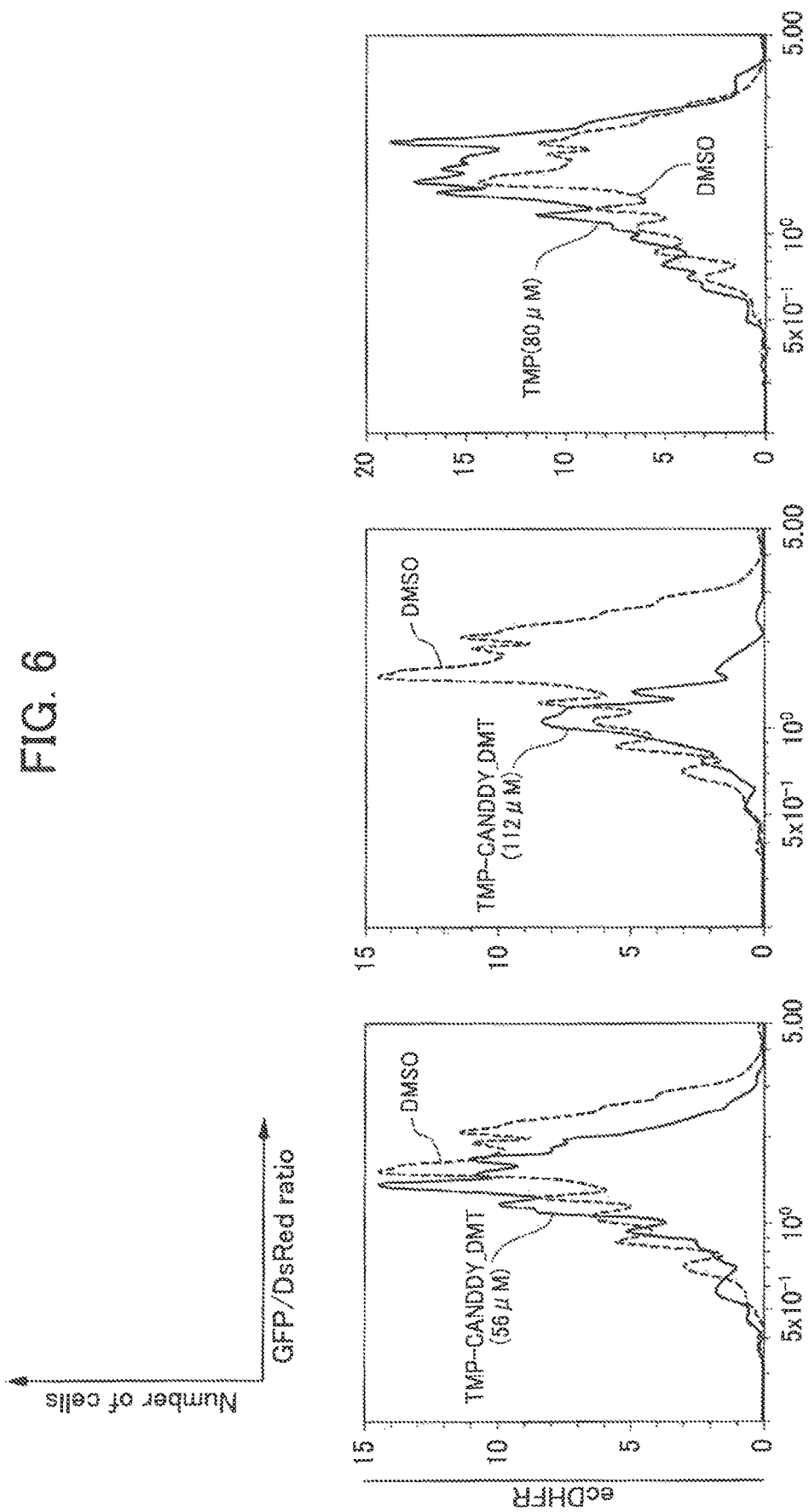
FIG. 6 shows the results of evaluation by FACS analysis of degradation (knockdown) of an ecDHFR protein forcibly expressed in HeLa cells through TMP-CANDDY_DMT.

The results of the FACS analysis are shown in FIG. 6. As shown in FIG. 6, when TMP-CANDDY_DMT was added, the graph is shifted toward the left in a concentration-dependent manner, demonstrating that degradation of the ecDHFR protein was induced by TMP-CANDDY_DMT. On the other hand, when TMP was added, the graph is overlapped to that of the control (DMSO), demonstrating that the ecDHFR protein was not degraded.

Reference Example 4

In Reference Example 4, degradation (knockdown) of a forcibly expressed ecDHFR protein in HeLa cells through TMP-CANDDY_DMT was evaluated by Western blot analysis.
(Preparation of Plasmid)
A plasmid expressing ecDHFR protein was produced, as in Reference Example 3.
(Introduction of Plasmid into HeLa Cells and Cell Seeding)
As in Reference Example 3, the plasmid was introduced into HeLa cells to transiently overexpress an ecDHFR protein or a DsRed protein for comparison in the cells. HeLa cells into which the plasmid had been introduced were seeded in a 24-well plate at a cell density of $4 \times 10^4$ cells/well, and then cultured under conditions of 37° C. and 5 vol % $CO_2$ for 40 hours.
(Addition of TMP-CANDDY_DMT to HeLa Cells)
Culture was performed for 40 hours after introduction of the plasmid, and then TMP-CANDDY_DMT was added to HeLa cells as follows. As a medium, a serum-free medium (37° C.) in which 1 mass % L-glutamine solution (Sigma-Aldrich) was added to D-MEM (high D-glucose, phenol red, sodium pyruvate) (Wako Pure Chemical Industries, Ltd.) was used. It is noted that the L-glutamine solution was added immediately before use. A DMSO solution containing TMP-CANDDY_DMT was mixed with the medium so that the concentration of DMSO was 1 vol %, and added to each well at 300 µL/well, and cultured under conditions of 37° C. and 5 vol % $CO_2$. Furthermore, in addition to an experiment group in which a DMSO solution containing TMP-CANDDY_DMT had been added, an experiment group in which a DMSO solution containing both TMP-CANDDY_DMT and bortezomib had been added was prepared. Cycloheximide as a protein synthesis inhibitor was added to the medium so as to give a concentration of 50 µg/mL 12 hours after addition of TMP-CANDDY_DMT. It is noted that as a control, a TMP-containing DMSO solution or DMSO was used.
(Evaluation of Degradation (Knockdown) of ecDHFR Protein Through TMP-CANDDY_DMT (Western Blot Analysis))
The medium was removed 24 hours after addition of TMP-CANDDY_DMT, and PBS was added to wash the cells. After removing PBS, a mixed solution of a cell lysis buffer (CelLytic™ M, Sigma) and a protease inhibitor (cOmplete™ Mini, EDTA-free, Roche) was added to each well at 55 µL/well. After being allowed to stand at 4° C. for 15 minutes, cells were detached with a pipette tip on ice. A cell solution was collected in a 1.5 mL tube, and flash frozen in liquid nitrogen, and then thawed on ice. After repeating this freeze-thaw cycle three times, the solution was centrifuged (at 13000 rpm×20 minutes, 4° C.), and the supernatant (cell extract) was collected.

The cell extract collected was subjected to Western blot analysis. An SDS-PAGE gel was prepared using TGX™

FastCast™ Acrylamide Kit, 12% (Bio-Rad). Electrophoresis samples were prepared in a 6×SDS-PAGE sample buffer (62.5 mM Tris-HCl pH 6.8, 2% SDS, 5% 2-mercaptoethanol, 10% glycerol, 0.25% BPB), and placed on a heat block at 95° C. for 4 minutes. Electrophoresis was performed at 150 V for 50 minutes (electrophoresis buffer; 195 mM glycine, 25 mM Tris).

After electrophoresis, proteins were transferred to a PVDF membrane (Immobion™-P, Millipore) under conditions of 100 V and 40 minutes using a tank-type blotting device and a transfer buffer (25 mM Tris-HCl, 195 mM glycine, 0.01% SDS, 15% methanol). The membrane after transfer was shaken and blocked at room temperature for 30 minutes in 5% skim milk/high-salt TBS-T (100 mM Tris-HCl, 500 mM NaCl, 0.2% Tween-20, pH 7.6). After blocking, the membrane was rinsed with high-salt TBS-T, and an antibody reaction was performed in 1% skim milk/high-salt TBS-T. As the antibody, anti-HA-peroxidase and high-affinity (3F10) rat monoclonal antibody (25 U/mL) (Roche) diluted 1000 times was used. The membrane was shaken at room temperature for 1 hour, and then washed with high-salt TBS-T for 5 minutes. It is noted that washing was performed three times. Further, the membrane was washed with High-Salt TBS (100 mM Tris-HCl, 500 mM NaCl, pH 7.6) for 5 minutes. Subsequently, the membrane was treated with a chemiluminescence reagent Immobilon™ Western (Millipore), and then chemiluminescence was detected using a lumino image analyzer LAS-3000 (FUJIFILM Corporation).

Next, a reaction for detecting GAPDH as a control was performed using the same membrane. The membrane was washed with TBS-T (100 mM Tris-HCl, 150 mM NaCl, 0.1% Tween-20, pH 7.6), and blocked by shaking at room temperature for 30 minutes in 5% skim milk/TBS-T. After blocking, a primary antibody reaction was performed in 5% skim milk/TBS-T. As the primary antibody, an anti-GAPDH antibody (6C5, SantaCruz, diluted 20000 times) was used. The membrane was shaken at room temperature for 60 minutes, and then washed with TBS-T for 5 minutes. It is noted that washing was performed three times. After the primary antibody reaction, a secondary antibody reaction was performed in 2% skim milk/TBS-T. As the secondary antibody, anti-mouse IgG (H+L) antibody (A90-116P-33, Bethyl) diluted 20000 times was used. The membrane was shaken at room temperature for 30 minutes, and then washed with TBS-T for 5 minutes. It is noted that washing was performed three times. Further, the membrane was washed with TBS (100 mM Tris-HCl, 150 mM NaCl, pH 7.6) for 5 minutes. Subsequently, the membrane was treated with a chemiluminescence reagent Immobilon™ Western (Millipore), and then chemiluminescence was detected using a lumino image analyzer LAS-3000 (FUJIFILM Corporation). Detected bands were quantified with an image processing software ImageJ (NIH).

Figure 7A:
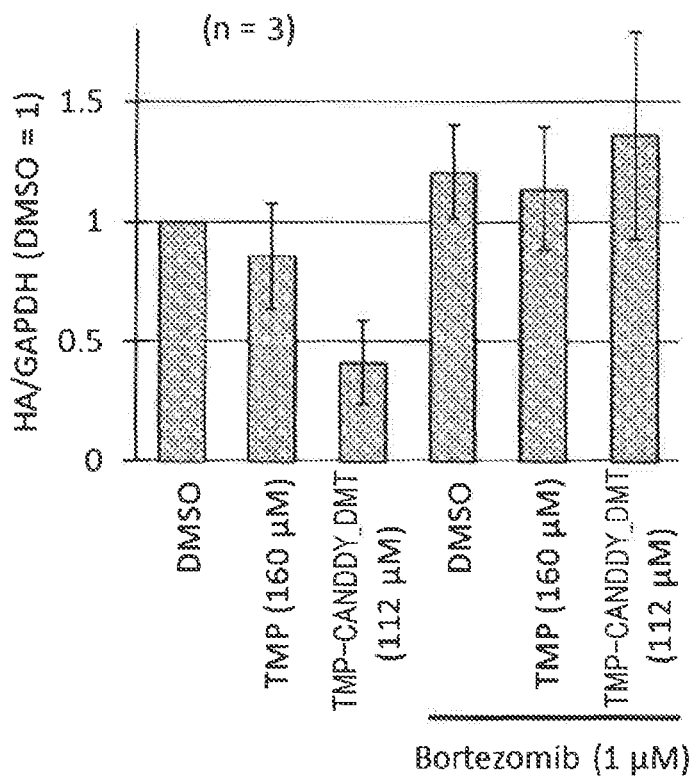
FIG. 7A shows the results of evaluation by Western blot analysis of degradation (knockdown) of an ecDHFR protein forcibly expressed in HeLa cells through TMP-CANDDY_DMT.
Figure 7B:
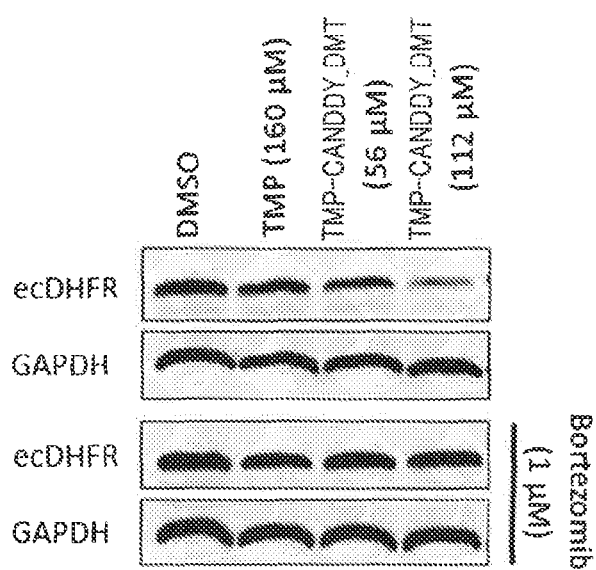
FIG. 7B shows the results of evaluation by Western blot analysis of degradation (knockdown) of an ecDHFR protein forcibly expressed in HeLa cells through TMP-CANDDY_DMT.

The results of the Western blot analysis are shown in FIGS. 7A and 7B. As shown in FIGS. 7A and 7B, when TMP-CANDDY_DMT was added, the amount of the ecDHFR protein was reduced, but when TMP was added, the amount of the ecDHFR protein was not reduced. Furthermore, when both TMP-CANDDY_DMT and bortezomib were added, as compared with the addition of TMP-CANDDY_DMT, degradation of the ecDHFR protein was inhibited. This result supports that TMP-CANDDY_DMT leads the ecDHFR protein to the degradation by a proteasome.

Reference Example 5

In Reference Example 5, a protein affinity molecule and a protein-degradation inducing tag were linked to each other to synthesize TMP-CANDDY_ALLN as a protein-degradation inducing molecule.

As the protein affinity molecule, as in Reference Example 1, TMP-NH₂ was used. Furthermore, as the protein-degradation inducing tag, a compound (CANDDY_ALLN) in which an active site (formyl group) of ALLN as a proteasome inhibitor was substituted with a carboxy group was used.

The method of synthesizing TMP-CANDDY_ALLN is described in detail as the following synthesis scheme.

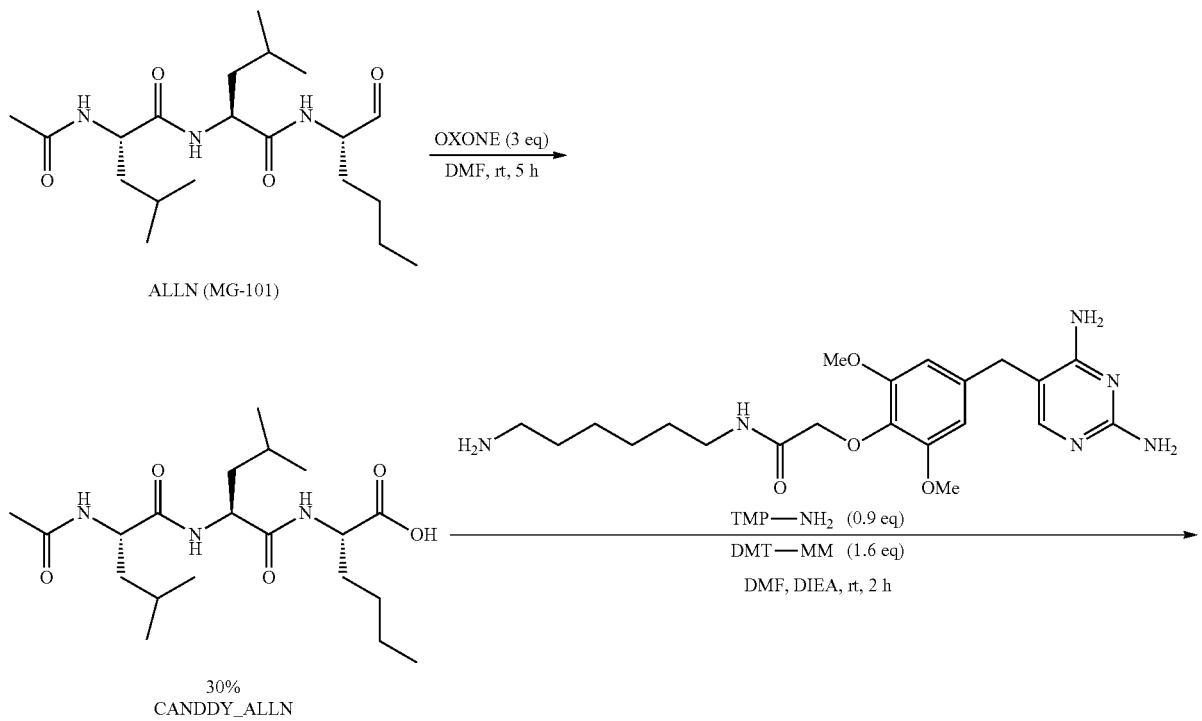

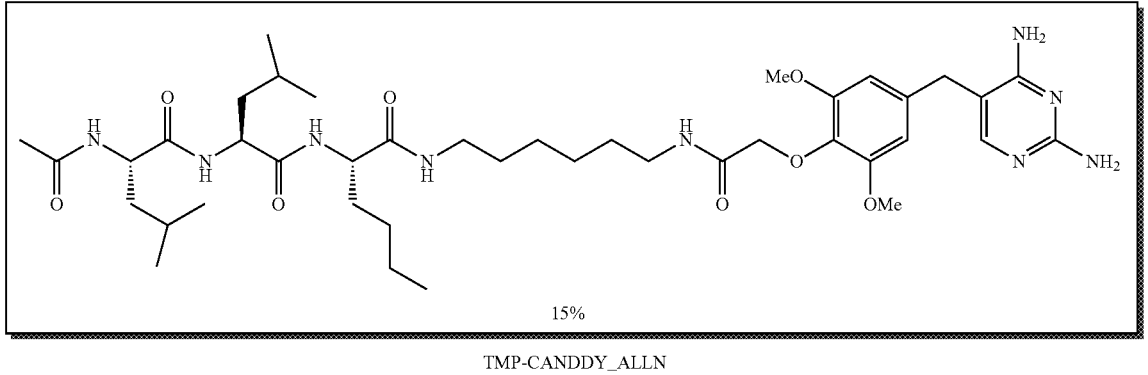

TMP-CANDDY_ALLN (Synthesis of CANDDY_ALLN)

ALLN (87.2 mg, 0.23 mmol, 1 eq, Code No. 07036-24, Nacalai Tesque, Inc.) was charged into an eggplant flask, and 2 mL of dehydrate DMF was added. After the resultant solution was stirred at room temperature for 5 minutes, Oxone (212.1 mg, 0.69 mmol, 3 eq, Code No. 228036, Sigma-Aldrich) was directly added to a reaction solution, and the reaction solution was stirred at room temperature for 5 hours. The reaction solution was diluted with water, and extracted with chloroform three times. After being dried over anhydrous sodium sulfate, the solvent was evaporated under reduced pressure. Separation and purification treatment was performed by silica gel chromatography (Code No. 30511-35, Nacalai Tesque, Inc.) (chloroform/methanol=20/1 to 10/1, gradient) to obtain CANDDY_ALLN (27.0 mg, 0.068 mmol, 30%).

(Synthesis of TMP-CANDDY_ALLN)

CANDDY_ALLN (26.8 mg, 0.067 mmol, 1 eq) and separately synthesized TMP-NH$_2$ (Long, M. J. et al., Chem. Biol., 2012, 19(5), 629-637) (26.0 mg, 0.060 mmol, 0.9 eq) were charged into an eggplant flask, and 2 mL of dehydrate DMF was added. After the resultant solution was stirred at room temperature for 5 minutes, 0.1 mL of DIPEA was added to neutralize the solution. The obtained product was stirred for 5 minutes at room temperature, then DMT-MM (30.0 mg, 0.11 mmol, 1.6 eq, Code No. 329-53751, Wako Pure Chemical Industries, Ltd.) was directly added to a reaction solution, and stirred at room temperature for 2 hours. Under cooling conditions, 10 mL of 10 mass % brine/0.1 N aqueous hydrochloric acid was added, and extracted with ethyl acetate three times. This was washed with 0.5 N aqueous hydrochloric acid and then brine, and then dried over anhydrous sodium sulfate. After evaporating the solvent under reduced pressure, separation and purification treatment was performed by silica gel chromatography (Code No. 30511-35, Nacalai Tesque, Inc.) (chloroform/methanol=10/1) to obtain TMP-CANDDY_ALLN (8.2 mg, 0.010 mmol, 15%, isolated yield).

Reference Example 6

In Reference Example 6, as in Reference Example 2, a proteasome inhibitory activity of TMP-CANDDY_ALLN and an affinity of TMP-CANDDY_ALLN with a proteasome were evaluated.

FIGS. 8A to 8C show the proteasome activities against β1 (caspase-like activity), β2 (trypsin-like activity), and β5 (chymotrypsin-like activity), respectively. As can be seen in FIGS. 8A to 8C, it was demonstrated that with respect to the activities of β2 and β5, in TMP-CANDDY_ALLN, as compared with single use of ALLN, the inhibitory activity was weakened, and the inhibitory activity of ALLN was inactivated. It was reported that β1 was not inhibited by ALLN (Kaiser, M. et al., Chem. Bio. Chem., 2004, 5, 1256-1266). The result was consistent with this report. Further, the inhibitory activity of TMP-CANDDY_ALLN was found to be increased against any of β1, β2, and β5 in a concentration dependent manner, indicating that TMP-CANDDY_ALLN had an affinity with a proteasome.

Reference Example 7

In Reference Example 7, degradation (knockdown) of a forcibly expressed ecDHFR protein in HeLa cells through TMP-CANDDY_ALLN was evaluated by FACS analysis.

(Preparation of Plasmid)

A plasmid (pMIR-DsRed-IRES-ecDHFR-HA-GFP) expressing the ecDHFR protein was prepared, as in Reference Example 3.

(Introduction of Plasmid into HeLa Cells and Cell Seeding)

As in Reference Example 3, the plasmid was introduced into HeLa cells to transiently overexpress an ecDHFR protein or a DsRed protein for comparison in the cells. HeLa cells into which the plasmid had been introduced were seeded in a 24-well plate at a cell density of $4 \times 10^4$ cells/well, and then cultured under conditions of 37° C. and 5 vol % $CO_2$ for 40 hours.

(Addition of TMP-CANDDY_ALLN to HeLa Cells)

Culture was performed for 40 hours after introduction of the plasmid, and then TMP-CANDDY_ALLN was added to HeLa cells as follows. As a medium, a serum-free medium (37° C.) in which 1 mass % L-glutamine solution (Sigma-Aldrich) was added to D-MEM (high D-glucose, phenol red, sodium pyruvate) (Wako Pure Chemical Industries, Ltd.) was used, and added to each well at 300 µL/well. It is noted that the L-glutamine solution was added immediately before use. A DMSO solution containing TMP-CANDDY_ALLN was added to each well at 3 µL/well, and cultured under conditions of 37° C. and 5 vol % $CO_2$. As a control, a TMP-containing DMSO solution or DMSO was used.

(Evaluation of Degradation of Protein (Knockdown) of ecDHFR Protein Through TMP-CANDDY_ALLN (FACS Analysis))

The medium was removed 24 hours after addition of TMP-CANDDY_ALLN, and then PBS was added to wash the cells. After removing PBS, trypsin (0.25 w/v % Trypsin-1 mmol/L EDTA.4 Na solution with phenol red) (Wako Pure Chemical Industries, Ltd.) at 37° C. was added to each well at 200 μL/well, and cultured under conditions of 37° C. and 5 vol % CO$_2$ for 1 minute. After culturing, a medium, in which 10 mass % FBS and 1 mass % PenStrep (100 U/mL sodium penicillin G and 100 μg/mL streptomycin sulfate) (Wako Pure Chemical Industries, Ltd.) had been added, was added to each well at 300 μL/well, and suspended, and then a cell solution was collected in a 15-mL tube.

The cell solution collected was centrifuged (at 1000 rpm×5 minutes, 4° C.), and the supernatant was removed, and then suspended in 2 mL of PBS (37° C.). The cell solution after suspension was centrifuged (at 1000 rpm×5 minutes, 4° C.), and the supernatant was removed, and then 500 μL of an FACS buffer (1 mass % FBS/PBS) at 4° C. was added, and allowed to stand on ice.

A BD FACSCanto™ II (BD Biosciences) was used for flow cytometry, and the expression levels of the GFP and DsRed protein in the cells were quantified. The cell solution passed through a mesh with a pore size of 32 μm, and transferred to an FACS tube immediately before FACS analysis. The GFP/DsRed ratio per cell was computed using an analysis software FlowJo™ (TOMY Digital Biology Co., Ltd.), and the degradation (knockdown) of the ecDHFR protein by TMP-CANDDY_ALLN was determined from a shift in a graph.

Figure 9:
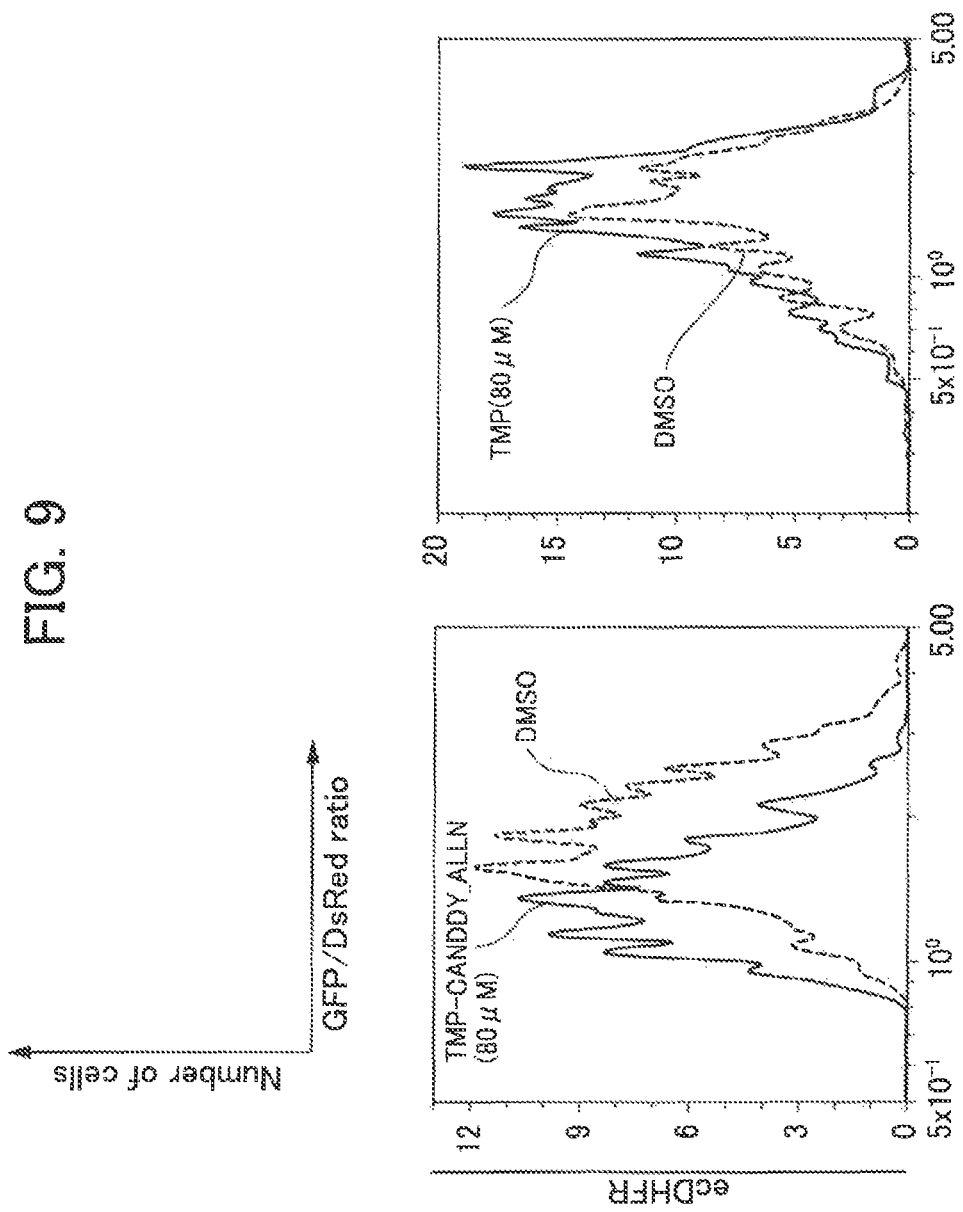
FIG. 9 shows the results of evaluation by FACS analysis of degradation (knockdown) of an ecDHFR protein forcibly expressed in HeLa cells through TMP-CANDDY_ALLN.

The results of the FACS analysis are shown in FIG. 9. As shown in FIG. 9, when TMP-CANDDY_ALLN was added, a graph is largely shifted toward the left as compared with the case where the control (DMSO) was added, demonstrating that degradation of the ecDHFR protein was induced by TMP-CANDDY_ALLN. On the other hand, when TMP was added, the graph is overlapped to that of the control (DMSO), demonstrating that the ecDHFR protein was not degraded.

The disclosure of Japanese Patent Application No. 2016-222681 filed on Nov. 15, 2016 is entirely incorporated herein by reference. All documents, patent applications, and technical standards cited herein are incorporated herein by reference to the same extent as if each of the documents, patent applications, and technical standards was specifically and individually indicated to be incorporated by reference.

The invention claimed is:

1. A p53 degradation inducing molecule, wherein the p53 degradation inducing molecule is a conjugate of a p53 affinity molecule that has an affinity with a p53 protein or a p53 complex, and a protein-degradation inducing tag that has an affinity with a 26S proteasome and does not inhibit degradation of a protein by the 26S proteasome, with the proviso that the conjugate excludes a fusion protein; and the p53 degradation inducing molecule is capable of inducing degradation of the p53 protein or the p53 complex.

2. The p53 degradation inducing molecule according to claim 1, wherein the p53 degradation inducing molecule is capable of inducing degradation of the p53 protein or the p53 complex in a ubiquitin-independent manner.

3. The p53 degradation inducing molecule according to claim 1, wherein the protein-degradation inducing tag has a structure represented by the following formula (I), or has a structure where a 26S proteasome inhibitory activity of a 26S proteasome inhibitor is inactivated, or has a structure of a proteasome activator:

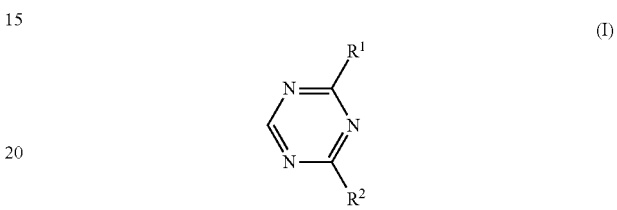

wherein in the formula (I), $R^1$ and $R^2$ each independently represent a hydrocarbon group having 1 to 20 carbon atoms, an alkoxy group having 1 to 20 carbon atoms, an aryloxy group having 6 to 20 carbon atoms, a hydroxy group, a carboxy group, an amino group, or a halogen group.

4. The p53 degradation inducing molecule according to claim 3, wherein the proteasome inhibitory activity is an inhibitory activity against at least one selected from a caspase-like activity, a trypsin-like activity, and a chymotrypsin-like activity.

5. A pharmaceutical composition comprising the p53 degradation inducing molecule according to claim 1.

6. The pharmaceutical composition according to claim 5, wherein the pharmaceutical composition is used for preventing or treating a p53 protein-mediated disease or condition.

7. The pharmaceutical composition according to claim 6, wherein the p53 protein-mediated disease or condition is a cancer, cellular senescence, a neurological disease, neuronal cell death, diabetes, or cardiac dysfunction.

8. The pharmaceutical composition according to claim 7, wherein the p53 protein-mediated disease or condition is cellular senescence.

9. The p53 degradation inducing molecule according to claim 1, wherein the p53 degradation inducing molecule is represented by the following formula:

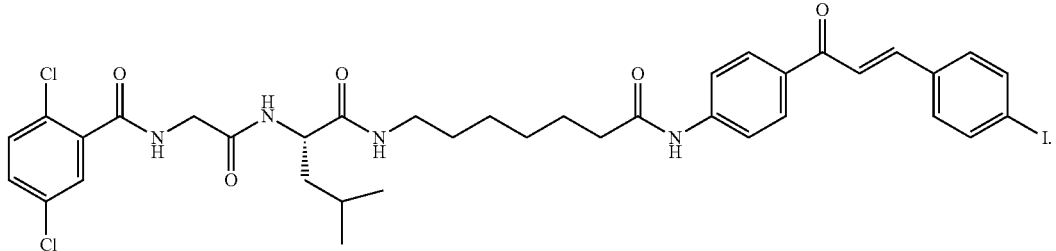 [SMILES: CC(C)C[C@H](NC(=O)CNC(=O)c1cc(Cl)ccc1Cl)C(=O)NCCCCCCC(=O)Nc1ccc(C(=O)/C=C/c2ccc(I)cc2)cc1]

* * * * *